United States Patent
Mehnert et al.

(10) Patent No.: US 10,953,125 B2
(45) Date of Patent: Mar. 23, 2021

(54) ARTICLES FORMED OF PULP BASE MATERIALS WITH MODULATED SCENT RELEASE

(71) Applicant: Enviroscent, Inc., Atlanta, GA (US)

(72) Inventors: Eric Mehnert, Lawrenceville, GA (US); Nicholas D. McKay, Atlanta, GA (US); Bao Trong Do, Decatur, GA (US)

(73) Assignee: ENVIROSCENT, INC., Atlanta, GA (US)

( * ) Notice: Subject to any disclaimer, the term of this patent is extended or adjusted under 35 U.S.C. 154(b) by 0 days.

(21) Appl. No.: 16/338,045

(22) PCT Filed: Sep. 29, 2017

(86) PCT No.: PCT/US2017/054245
§ 371 (c)(1),
(2) Date: Mar. 29, 2019

(87) PCT Pub. No.: WO2018/064449
PCT Pub. Date: Apr. 5, 2018

(65) Prior Publication Data
US 2019/0231919 A1    Aug. 1, 2019

Related U.S. Application Data

(60) Provisional application No. 62/402,906, filed on Sep. 30, 2016.

(51) Int. Cl.
*A61L 9/12* (2006.01)
*A61L 9/03* (2006.01)
(Continued)

(52) U.S. Cl.
CPC .............. *A61L 9/125* (2013.01); *A61K 9/007* (2013.01); *A61L 9/032* (2013.01); *A61L 9/035* (2013.01);
(Continued)

(58) Field of Classification Search
CPC .......... A61L 9/125; A61L 9/122; A61L 9/127; A61L 9/032; A61L 9/035; A61L 9/037;
(Continued)

(56) References Cited

U.S. PATENT DOCUMENTS

| | | |
|---|---|---|
| 324,853 A | 8/1885 | Laurier |
| 855,984 A | 6/1907 | Russell |

(Continued)

FOREIGN PATENT DOCUMENTS

| | | |
|---|---|---|
| CN | 1341357 | 3/2002 |
| CN | 102917878 | 1/2016 |

(Continued)

OTHER PUBLICATIONS

Machine Translation of JP 09-276384 (Year: 1997).*
(Continued)

*Primary Examiner* — Lessanework Seifu
(74) *Attorney, Agent, or Firm* — Kilpatrick Townsend & Stockton LLP

(57) ABSTRACT

Described are articles formed of a pulp base material comprising fibers, wherein pores are formed between the fibers. A volatile composition with at least one top note component and at least one base note component at least partially fills the pores of the pulp base material. A release rate of the at least one top note component is modulated by the pulp base material, and a release rate of the at least one base note component is enhanced by the pulp base material.

25 Claims, 80 Drawing Sheets

(51) Int. Cl.
    *A61K 9/00*     (2006.01)
    *A61M 15/08*     (2006.01)
    *A61L 9/04*     (2006.01)
    *A61M 11/04*     (2006.01)
    *A61M 21/00*     (2006.01)

(52) U.S. Cl.
    CPC .............. *A61L 9/037* (2013.01); *A61L 9/042* (2013.01); *A61L 9/122* (2013.01); *A61L 9/127* (2013.01); *A61M 15/08* (2013.01); *A61L 2209/12* (2013.01); *A61L 2209/133* (2013.01); *A61L 2209/15* (2013.01); *A61M 11/041* (2013.01); *A61M 2021/0016* (2013.01); *A61M 2205/02* (2013.01); *A61M 2205/59* (2013.01); *A61M 2207/00* (2013.01)

(58) Field of Classification Search
    CPC ................. A61L 9/042; A61L 2209/12; A61L 2209/133; A61L 2209/15
    See application file for complete search history.

(56) References Cited

U.S. PATENT DOCUMENTS

| | | |
|---|---|---|
| 934,502 A | 9/1909 | Canon |
| 1,777,820 A | 10/1930 | Anenberg |
| 1,878,401 A | 9/1932 | John |
| 1,988,141 A | 1/1935 | Schaller |
| 2,120,204 A | 6/1938 | Langhorst |
| 2,303,073 A | 11/1942 | Brown |
| 2,615,754 A | 10/1952 | Lindenberg |
| 2,626,833 A | 1/1953 | Valentine |
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,575,345 A | 4/1971 | Buck, Jr. |
| 3,634,564 A | 1/1972 | Okamoto et al. |
| 3,770,856 A | 11/1973 | Ueki et al. |
| 3,790,081 A | 2/1974 | Thornton et al. |
| 3,870,542 A | 3/1975 | Ida et al. |
| 3,954,928 A | 5/1976 | Omori et al. |
| 4,020,156 A | 4/1977 | Murray et al. |
| 4,081,384 A | 3/1978 | Pracht |
| 4,210,487 A | 7/1980 | Driscoll |
| 4,234,627 A | 11/1980 | Schilling |
| 4,384,589 A | 5/1983 | Morris |
| 4,753,389 A | 6/1988 | Davis |
| 4,802,626 A | 2/1989 | Forbes et al. |
| 5,103,654 A | 4/1992 | Gee et al. |
| 5,112,688 A | 5/1992 | Michael |
| 5,145,842 A | 9/1992 | Driedger et al. |
| 5,233,680 A | 8/1993 | Fussell |
| 5,372,303 A | 12/1994 | Paul |
| 5,395,047 A | 3/1995 | Pendergrass, Jr. |
| 5,437,410 A | 8/1995 | Babasade |
| 5,503,332 A | 4/1996 | Glenn |
| 5,544,812 A | 8/1996 | Torres |
| 5,578,563 A | 11/1996 | Trinh et al. |
| 5,710,406 A | 1/1998 | Garris et al. |
| 5,763,038 A | 6/1998 | Wood |
| 5,763,788 A | 6/1998 | Friedhoff et al. |
| 5,771,503 A | 6/1998 | Valimaa et al. |
| 5,832,648 A | 11/1998 | Malone |
| 5,940,921 A | 8/1999 | Wood et al. |
| 6,014,788 A | 1/2000 | Jaffri |
| 6,039,488 A | 3/2000 | Krawczyk et al. |
| 6,143,675 A | 11/2000 | Mccollam et al. |
| 6,158,668 A | 12/2000 | Burgeson |
| 6,168,088 B1 | 1/2001 | Mobley |
| 6,183,596 B1 | 2/2001 | Matsuda et al. |
| 6,194,375 B1 | 2/2001 | Ness et al. |
| 6,214,163 B1 | 4/2001 | Matsuda et al. |
| 6,248,703 B1 | 6/2001 | Finucane et al. |
| 6,261,483 B1 | 7/2001 | Frank et al. |
| 6,329,057 B1 | 12/2001 | Dungworth et al. |
| 6,575,383 B2 | 6/2003 | Dobler et al. |
| 6,668,482 B1 | 12/2003 | Ruffin et al. |
| 6,688,551 B1 | 2/2004 | He et al. |
| 6,803,033 B2 | 10/2004 | McGee et al. |
| 6,921,024 B2 | 7/2005 | Donnelly et al. |
| 6,954,963 B2 | 10/2005 | McKay |
| 7,235,261 B2 | 6/2007 | Smith et al. |
| 7,741,266 B2 | 6/2010 | Bell et al. |
| 8,919,662 B2 | 12/2014 | Sherwood |
| 9,132,204 B2 | 9/2015 | McKay et al. |
| 9,149,552 B1 | 10/2015 | Do et al. |
| 9,309,487 B2 | 4/2016 | Denutte et al. |
| 9,381,266 B2 | 7/2016 | Sherwood |
| 9,694,096 B2 | 7/2017 | McKay et al. |
| 9,694,097 B2 | 7/2017 | Do et al. |
| 10,286,098 B2 | 5/2019 | Sherwood |
| 10,647,868 B2 | 5/2020 | Do et al. |
| 2002/0136886 A1 | 9/2002 | He et al. |
| 2003/0024997 A1 | 2/2003 | Welch et al. |
| 2003/0211799 A1 | 11/2003 | Yao et al. |
| 2004/0001891 A1 | 1/2004 | Smith et al. |
| 2004/0197221 A1 | 10/2004 | Stanley, III |
| 2005/0204493 A1 | 9/2005 | Legus et al. |
| 2006/0147353 A1 | 7/2006 | Wang |
| 2006/0221614 A1 | 10/2006 | Van Dyn Hoven |
| 2007/0057086 A1 | 3/2007 | Van Kippersluis |
| 2007/0187524 A1 | 8/2007 | Sherwood |
| 2007/0224232 A1 | 9/2007 | Sherwood |
| 2008/0008860 A1 | 1/2008 | Murray et al. |
| 2008/0009616 A1 | 1/2008 | Frank et al. |
| 2008/0286143 A1 | 11/2008 | Grodsky |
| 2011/0148329 A1 | 6/2011 | Demarest et al. |
| 2011/0198409 A1 | 8/2011 | Gorman et al. |
| 2011/0256364 A1 | 10/2011 | Boyer et al. |
| 2011/0262377 A1 | 10/2011 | McKay et al. |
| 2015/0108242 A1 | 4/2015 | Sherwood |
| 2015/0136872 A1 | 5/2015 | Sherwood |
| 2015/0217016 A1 | 8/2015 | McKay et al. |
| 2015/0374869 A1 | 12/2015 | McKay et al. |
| 2016/0089468 A1 | 3/2016 | Do et al. |
| 2016/0136317 A9 | 5/2016 | Sherwood |
| 2016/0136318 A9 | 5/2016 | Sherwood |
| 2016/0279276 A1 | 9/2016 | Sherwood |
| 2016/0279277 A1 | 9/2016 | Sherwood |
| 2017/0266333 A1 | 9/2017 | McKay et al. |
| 2017/0296688 A1 | 10/2017 | Do et al. |
| 2018/0326109 A1 | 11/2018 | McKay et al. |
| 2019/0240366 A1 | 8/2019 | Sherwood |

FOREIGN PATENT DOCUMENTS

| | | |
|---|---|---|
| DE | 20110608 | 3/2002 |
| EP | 1190725 | 3/2002 |
| GB | 914421 | 1/1963 |
| GB | 1221488 | 2/1971 |
| GB | 1226448 | 3/1971 |
| GB | 1387265 | 3/1975 |
| JP | 49072551 | 6/1974 |
| JP | 53159844 | 12/1978 |
| JP | 59154255 | 10/1984 |
| JP | 6284845 | 10/1994 |
| JP | 8289925 | 11/1996 |
| JP | 9-276384 | * 10/1997 |
| JP | 2000093495 | 4/2000 |
| JP | 2000107274 | 4/2000 |
| JP | 2000312712 | 11/2000 |
| JP | 2001224675 | 8/2001 |
| JP | 2006333904 | 12/2006 |
| JP | 2007051398 | 3/2007 |
| JP | 2008127360 | 6/2008 |
| JP | 2011057570 | 3/2011 |
| KR | 2019940001095 | 2/1994 |
| KR | 1020070079756 | 8/2007 |
| KR | 1020100094762 | 8/2010 |
| KR | 101856793 | 5/2018 |
| WO | 9112029 | 8/1991 |
| WO | 9807405 | 2/1998 |
| WO | 9842818 | 10/1998 |

(56) References Cited

FOREIGN PATENT DOCUMENTS

| WO | 9847477    | 10/1998 |
|----|------------|---------|
| WO | 9847478    | 10/1998 |
| WO | 9943667    | 9/1999  |
| WO | 0072951    | 12/2000 |
| WO | 2004020566 | 3/2004  |
| WO | 2006002395 | 1/2006  |
| WO | 2006002395 | 8/2007  |
| WO | 2007135424 | 11/2007 |
| WO | 2009078038 | 6/2009  |
| WO | 2011123723 | 10/2011 |
| WO | 2013064501 | 5/2013  |
| WO | 2014039549 | 3/2014  |
| WO | 2016053802 | 4/2016  |
| WO | 2018064449 | 4/2018  |

OTHER PUBLICATIONS

International Application No. PCT/US2017/054245, International Preliminary Report on Patentability dated Apr. 11, 2019, 9 pages.
International Application No. PCT/US2017/054245, International Search Report and Written Opinion dated Dec. 12, 2017, 10 pages.
Application No. CN201780072853.8, Office Action, dated Jul. 23, 2020, 23 pages.
Application No. EP17857477.8, Extended European Search Report, dated Jul. 13, 2020, 15 pages.
EP17857477.8, "Partial Supplementary European Search Report", dated May 4, 2020, 13 pages.
Chinese Application No. 201780072853.8, Second Office Action dated Dec. 31, 2020, 11 pages.

\* cited by examiner

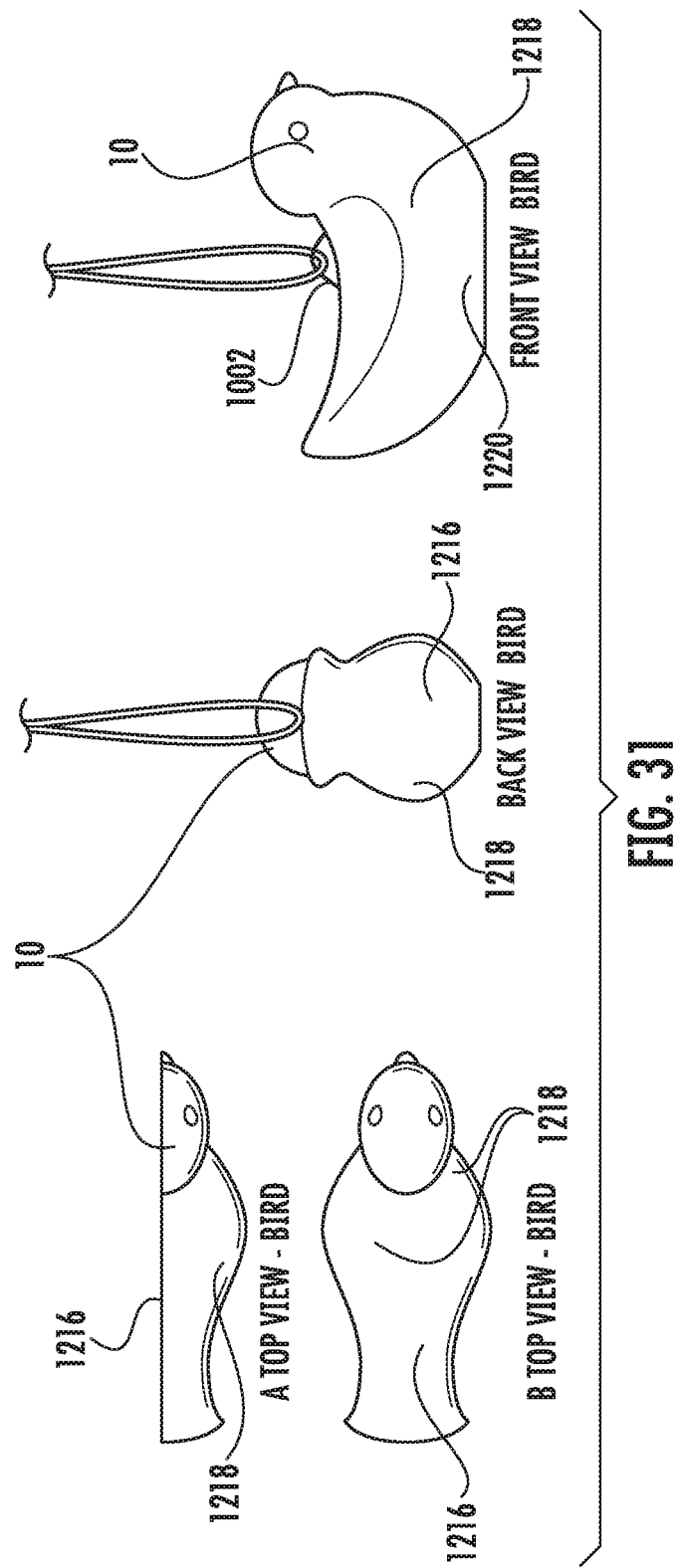

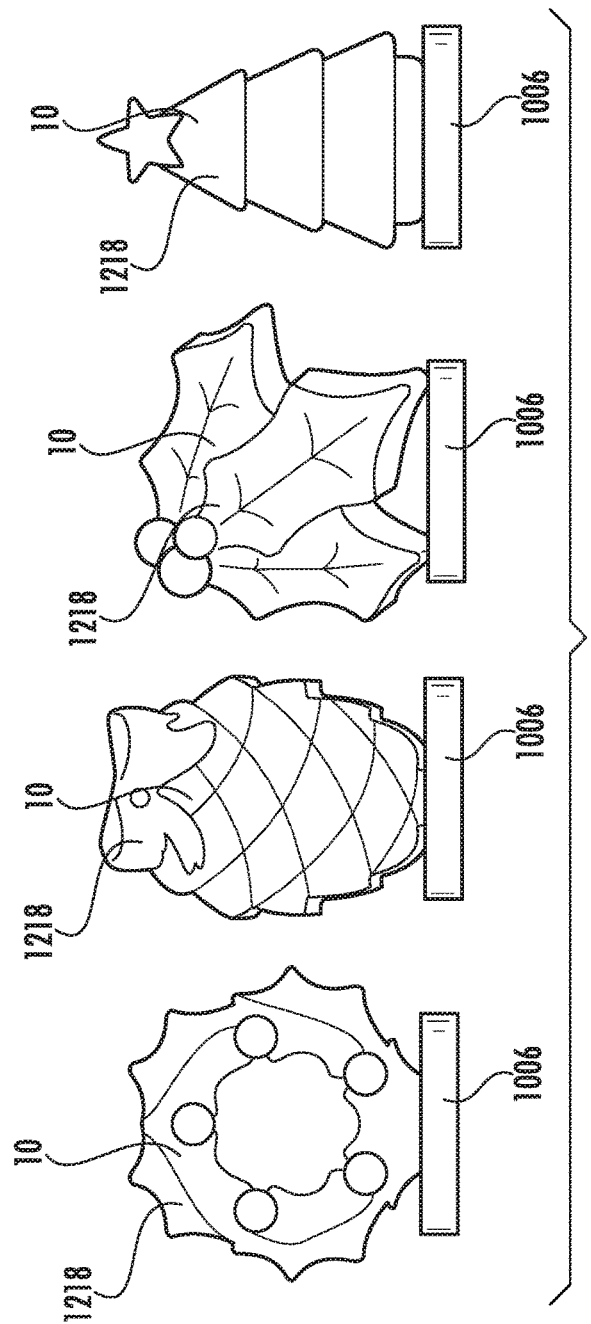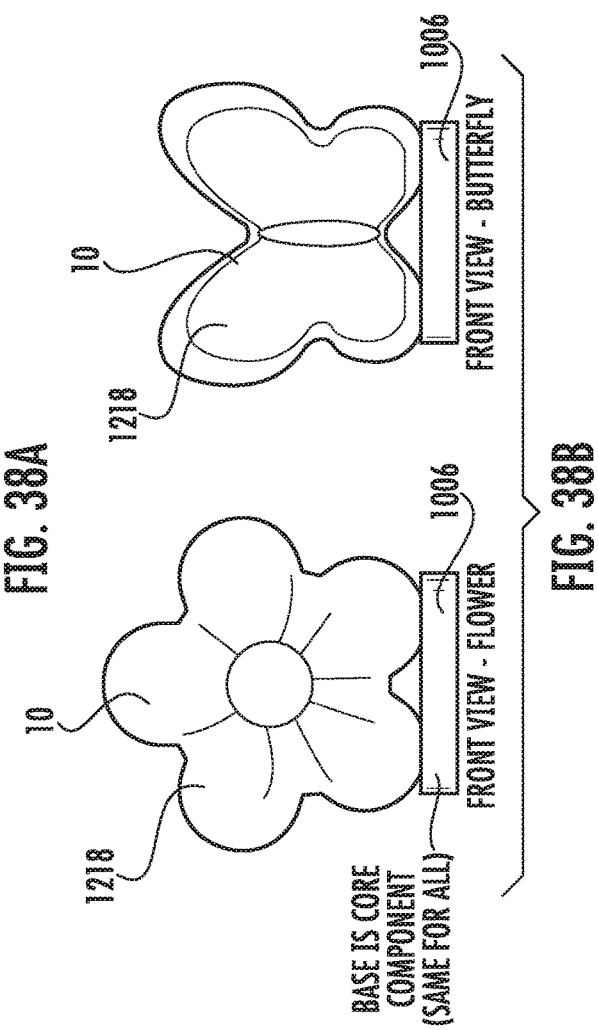

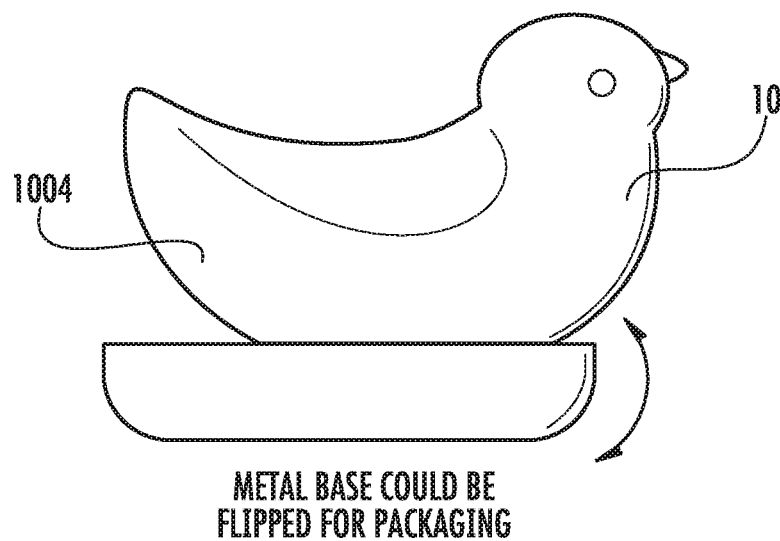
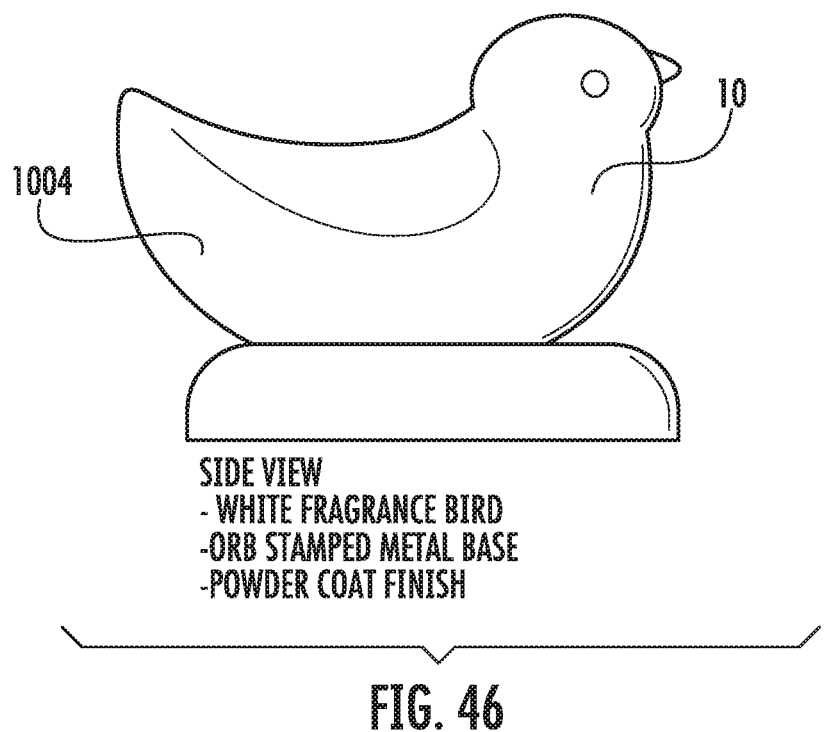
FIG. 46

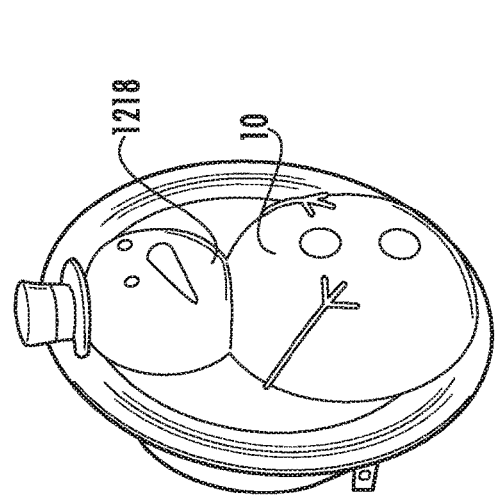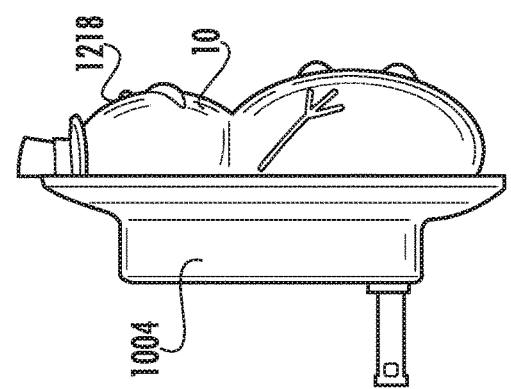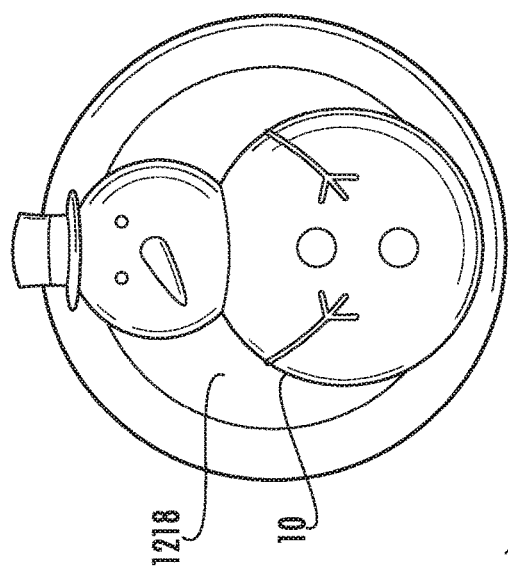
FIG. 54A
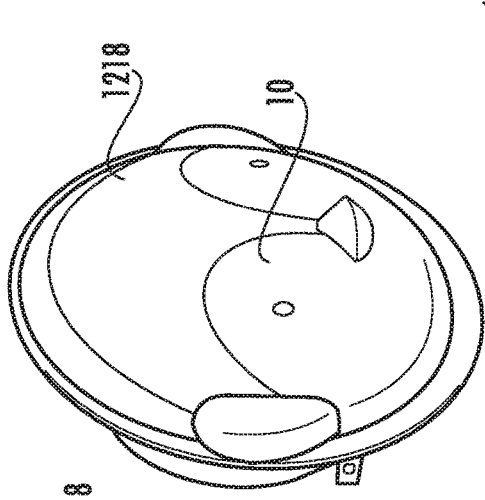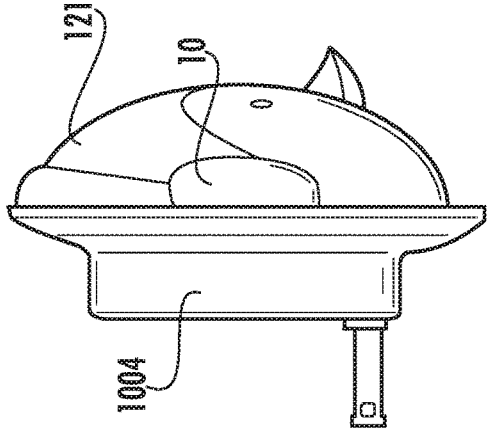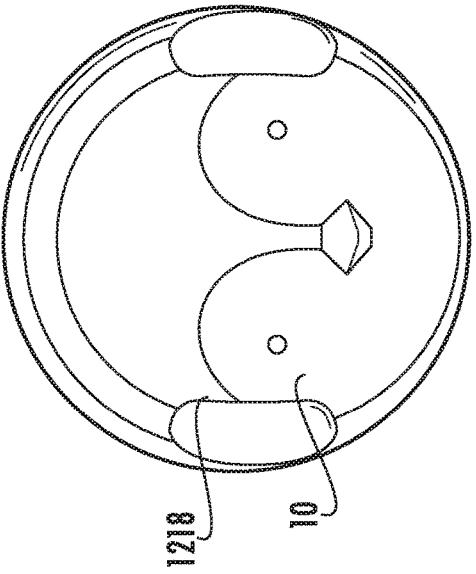
FIG. 54B

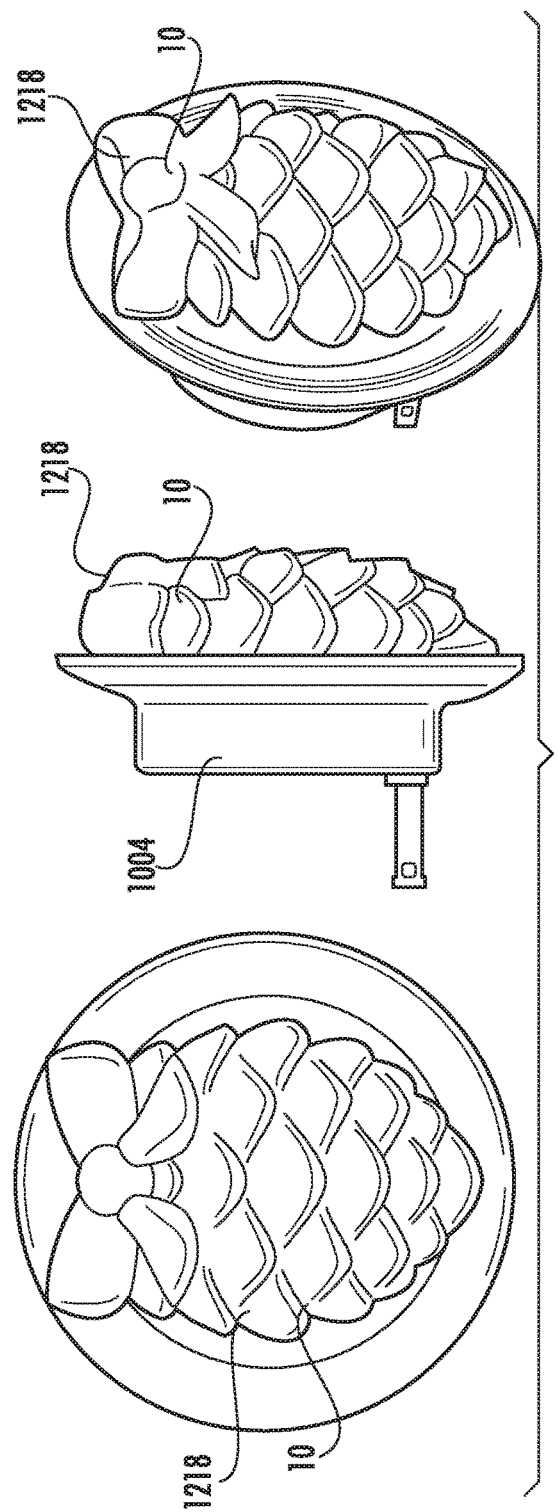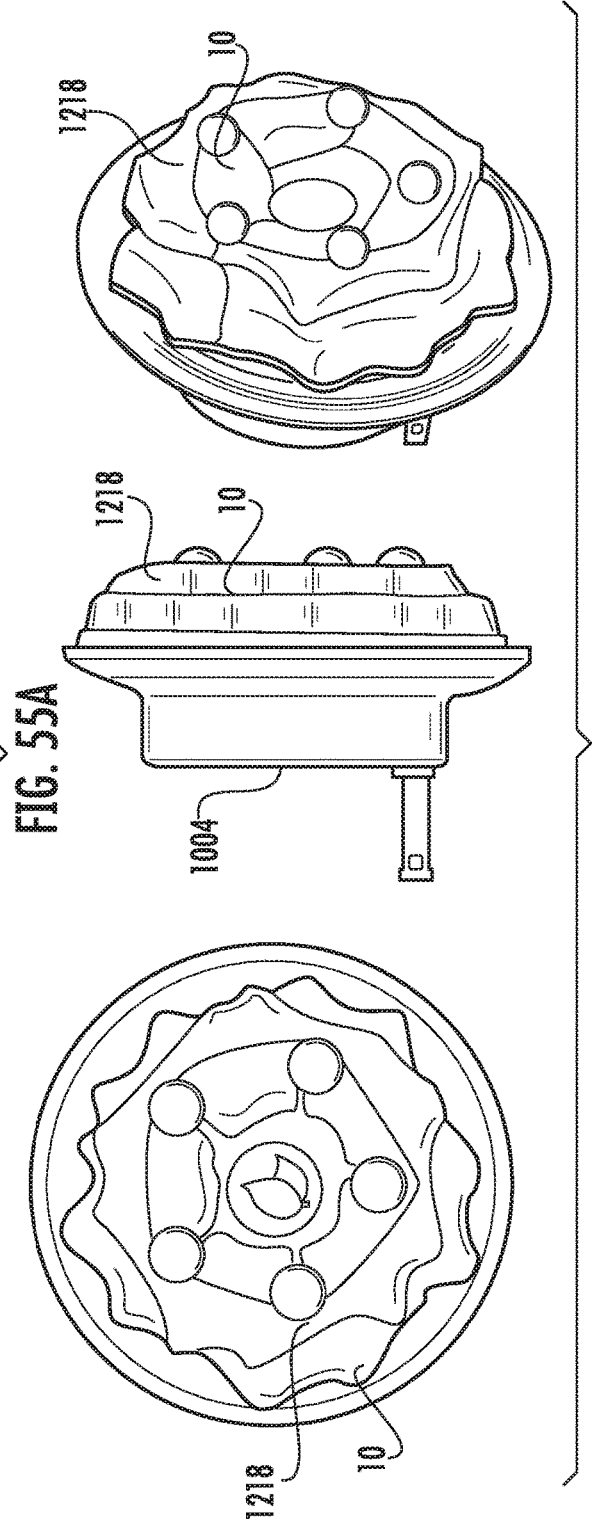
FIG. 55A
FIG. 55B

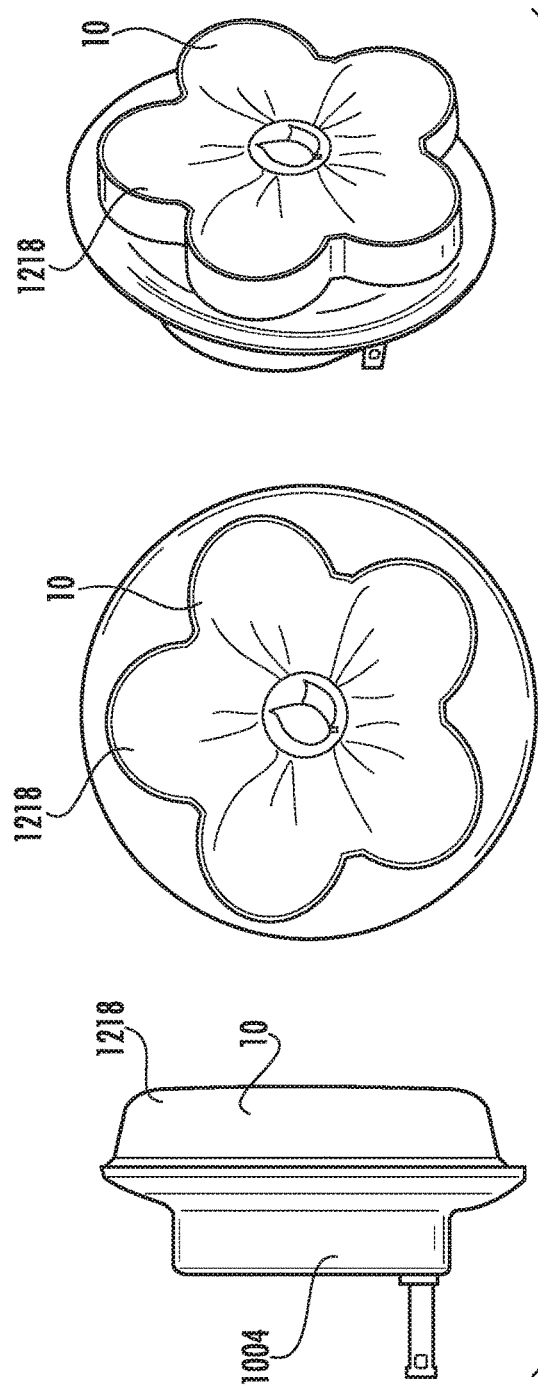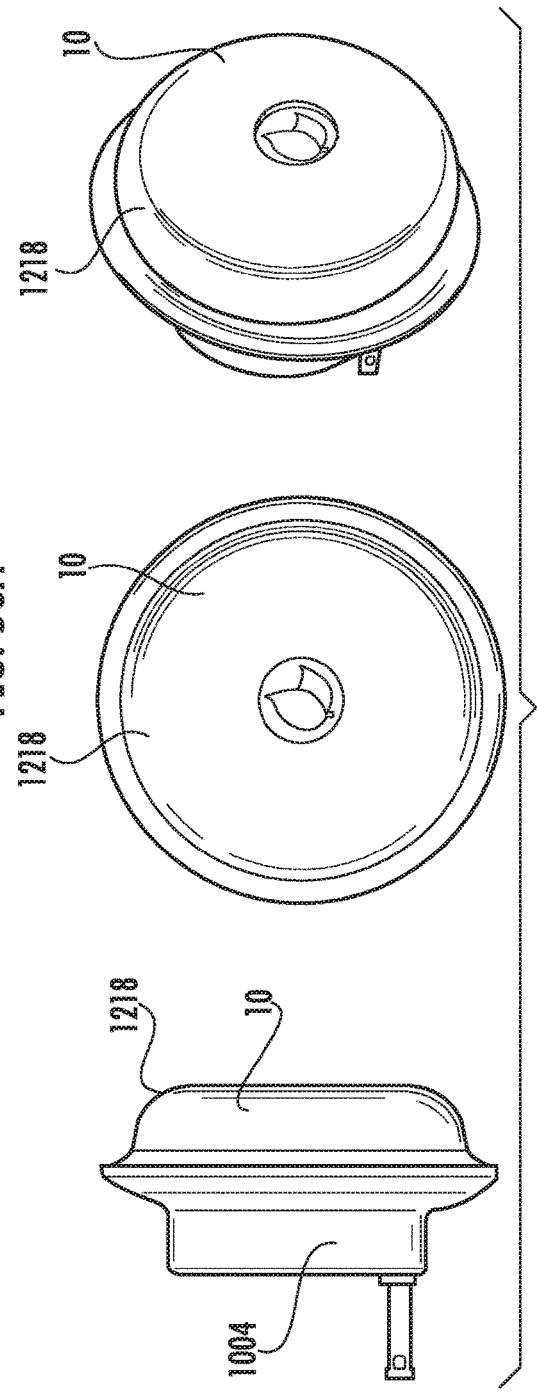

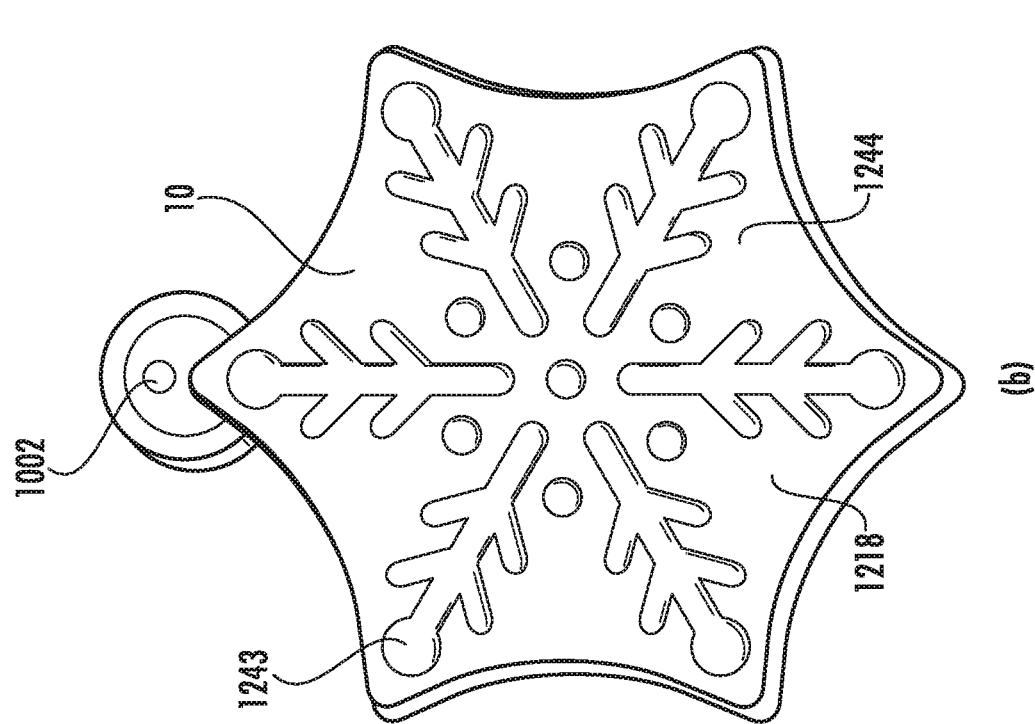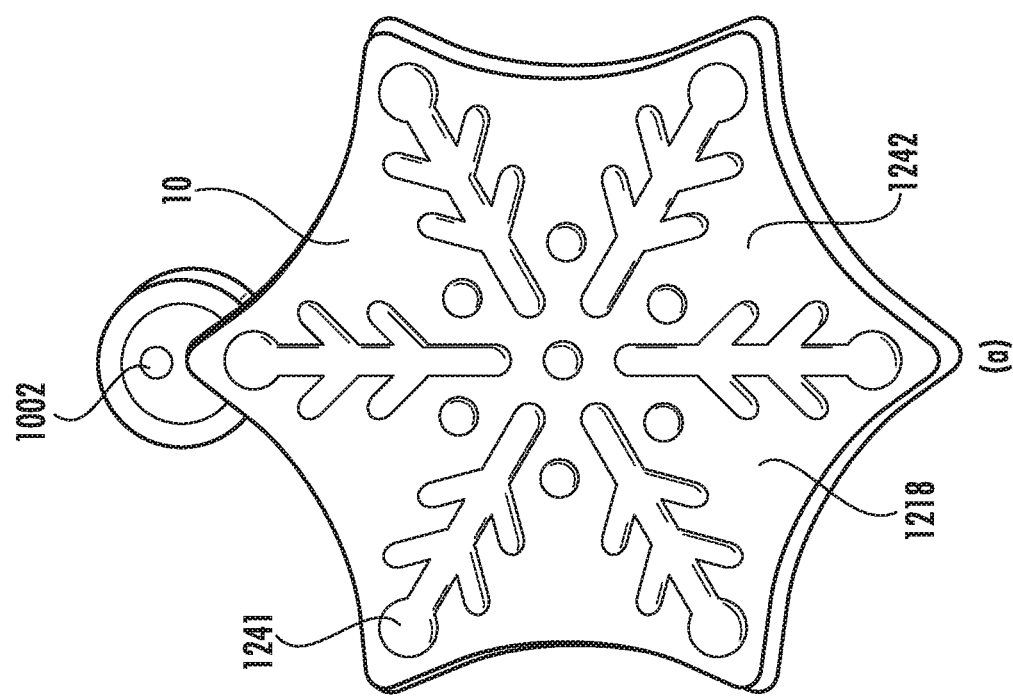
FIG. 75

ARTICLES FORMED OF PULP BASE MATERIALS WITH MODULATED SCENT RELEASE

CROSS REFERENCE TO RELATED APPLICATION

This application is related to and claims priority benefit from U.S. Provisional Application No. 62/402,906 ("the '906 application"), filed on Sep. 30, 2016, entitled ARTICLES FORMED OF PULP BASE MATERIALS WITH MODULATED SCENT RELEASE. The '906 application is hereby incorporated in its entirety by this reference.

FIELD OF THE INVENTION

The field of the invention relates to articles formed of pulp base materials, which are configured to provide a modulated release of volatile compositions, and more specifically relates to articles formed of pulp base materials that provide a modulated release of volatile olfactory or fragrance compounds.

BACKGROUND

Fragrance-releasing devices are well known and commonly used in household and commercial establishments to provide a pleasant environment for people in the immediate space. Further, aroma-driven experiences are well recognized to improve or enhance the general mood of individuals. In some instances, fragrances may trigger memories of experiences associated with the specific scent. Whether it is providing a pleasant environment, affecting a general demeanor, or triggering a nostalgic memory, a steady, long-lasting release of fragrance will ensure consumer and customer satisfaction.

Fragrance-release devices based on passive diffusion are limited in their product-use by a finite supply of the fragrance and its evaporation rate from a surface. In some examples, the fragrance-release device is designed to carry the fragrance liquid within its architecture so that the fragrance supply is finite and determined by the size of the fragrance-release device.

The evaporation rate of fragrance from the fragrance-release device is determined, at least in part, by the composition of the fragrance, where compositions containing more volatile compounds (e.g. "top" notes) will evaporate faster than those with less volatile compounds (e.g. "base" notes). A fragrance composition determines its character. As a result, changing the composition of the fragrance will affect the character. The release rate profile of fragrance is generally strong (more intense) at the beginning of product use, followed by decreasing intensity over time.

For these fragrances, there is a need to modulate the release of fragrance from the fragrance-release device to provide a steady and long-lasting fragrance release without changing the fragrance load and character. Specifically, there is a need to temper the release of fragrance compounds at the initial stage of product use, followed by facilitation of fragrance compound release at a later stage of product use. There is also a need to modulate the type of scent released over time so that the olfactory senses do not become immune to the scent released by the article.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, an article comprises a pulp base material comprising fibers, wherein pores are formed between the fibers, and a volatile composition comprising at least one top note component and at least one base note component. The volatile composition at least partially fills the pores of the pulp base material, wherein a release rate of the at least one top note component is modulated by the pulp base material, and wherein a release rate of the at least one base note component is enhanced by the pulp base material.

In some embodiments, the pulp base material comprises at least one low porosity zone and at least one high porosity zone. The at least one top note component may be added to the at least one low porosity zone, and the at least one base note component may be added to the at least one high porosity zone.

The at least one low porosity zone and the at least one high porosity zone may be formed by use of a mold having different drainage surfaces, by use of a divider within a mold, by application of different pressures to portions of a mold, by application of different pulp concentrations to portions of a mold, and/or by application of different amounts of gas or gas-forming materials to portions of the pulp base material. In some embodiments, the at least one low porosity zone is formed in a first mold and the at least one high porosity zone is formed in a second mold.

The article may comprise at least two pulp base materials joined together.

In some embodiments, the pulp base material comprises at least one surface having complex geometry. The complex geometry may comprise peaks and flatter regions. The peaks may enhance the release rate of the volatile composition and/or provide three-dimensional emission of the volatile composition.

The article may comprise an attachment element. The attachment element may comprise a hole.

The article may comprise a smooth surface for holding the article in an upright position. In some embodiments, a stand is coupled to the article to hold the article in an upright position.

A backing layer may be added to the article. The backing layer may be formed of a conductive material.

In some embodiments, the article may further comprise an opening through the article for placement of a light source.

In certain embodiments, the pulp base material comprises a first porosity and openings in which other materials having at least a second porosity are added to the pulp base material.

A modulating coating may applied to the pulp base material, only applied to the at least one low porosity zone, and/or only applied to the at least one high porosity zone.

In some embodiments, the article is combined with at least one energy source.

The at least one energy source may be a warmer bowl or plate and/or a fan. The article may form at least one blade of the fan.

In some embodiments, the article is positioned around a light source.

In some embodiments, the article is positioned within a support structure.

BRIEF DESCRIPTION OF THE DRAWINGS

In the following detailed description, embodiments of the invention are described referring to the following figures:

FIG. 31 includes top, front, and side views of an article formed by joining two pulp base materials, according to certain embodiments of the present invention.

FIGS. 38A and 38B include front images of articles with stands and a variety of shapes, according to certain embodiments of the present invention.

FIG. 46 includes side views of articles combined with energy sources, according to certain embodiments of the present invention.

FIGS. 54A and 54B include front, side, and perspective images of articles with a variety of shapes and coloration and a plug-in heating element, according to certain embodiments of the present invention.

FIGS. 55A and 55B include front, side, and perspective images of articles with a variety of shapes and coloration and a plug-in heating element, according to certain embodiments of the present invention.

FIGS. 56A and 56B include front, side, and perspective images of articles with a variety of shapes and coloration and a plug-in heating element, according to certain embodiments of the present invention.

FIG. 75 is a front view of an article, according to certain embodiments of the present invention.

DETAILED DESCRIPTION

Figure 1:
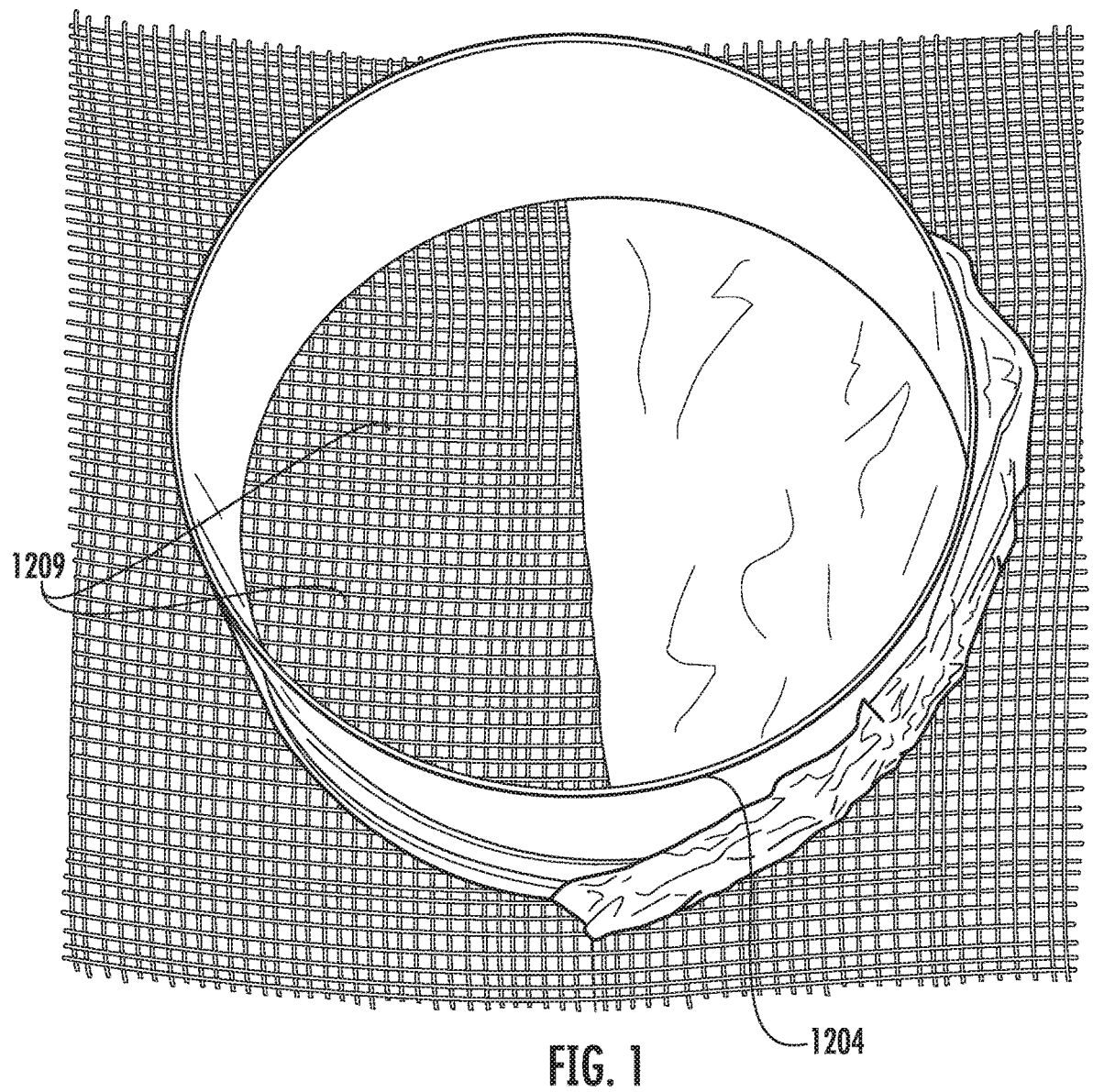
FIG. 1 is an image of a mold used to form a pulp base material, according to certain embodiments of the present invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

According to certain embodiments of the present invention, an article 10 comprises a base material 12.

A. Base Material

The base material 12 may comprise an internal structure 20 comprising a plurality of pores 22 that are configured to provide locations for the volatile composition 24 to be stored therein and released therefrom, which is described in detail below.

The base material 12 may comprise natural and/or synthetic pulp compositions; pulp compositions combined with other products, including but not limited to paper, cellulose, cellulose acetate, pulp lap, cotton linters, biological plant-derived materials (from living plants), synthesized pulp compositions, and mixed pulps; polymer material; porous material; and/or extrudate.

As known in the art, pulp is primarily a collection of fibers with other components of the source material, wherein the fibers are derived from a natural or synthetic source material, for example, biological plants (natural) or petroleum-based synthesis products (synthetic). Pulp may be produced from various types of woods using any one of several known pulping techniques. The pulp may be from hardwoods, softwoods, or mixtures thereof. The pulp may also be produced from bamboo, sugarcane, and other pulp sources. The pulp may also be made from recycled materials, and comprises recovering waste paper and remaking it into new products.

In certain embodiments, the number and/or size of the plurality of pores 22 (i.e., porosity) within the base material 12 may be controlled by the compactness and/or size of the fibers and/or particles that form the internal structure 20. For example, in certain embodiments of the base material 12 that comprise fibers, voids between the fibers form tiny air passages throughout the internal structure 20. The compactness of the fibers affects the degree in which the base material 12 allows gas or liquid to pass through it. For example, porosity may affect absorbency, uptake, and/or load amount of volatile compositions, or may affect the rate of release of such substances. Porosity and/or absorbency of the base material 12 may be affected by adding other materials, such as additives to the matrix material 12 as it is being formed from a composition, such as pulp or any other composition described above, so that the additives are located within the internal structure 20 of the base material 12 after formation.

The porosity of a base material 12 that comprises pulp may be affected at any stage of the pulp production process. An increased level of fiber refining causes the fibers to bond together more strongly and tightly, making the pulp material denser, thereby reducing the network of air passages and the porosity. The porosity of the base material 12 may also be controlled using other compression methods, which are described in detail below.

The porosity of the base material 12 is measured quantitatively as either the length of time it takes for a quantity of air to pass through a sample, or the rate of the passage of air through a sample, using either a Gurley densometer (in the first case) or a Sheffield porosimeter (in the second case). With the Gurley densometer, the porosity is measured as the number of seconds required for 100 cubic centimeters of air to pass through 1.0 square inch of a given material at a pressure differential of 4.88 inches of water, as described in ISO 5646-5, TAPPI T-460, or TAPPI T-536.

The porosity may affect how completely and how quickly the volatile composition 24 is absorbed into a pulp base material 12, as such absorption may occur primarily by capillary action. For example, a pulp base material 12 with high porosity may have increased absorbency of the volatile composition 24. As an example relating porosity to standard test methods for sheets of paper, the porosity of the pulp base material 12 may range from 0.01 Gurley second—100 Gurley seconds, and all ranges therein. In certain embodiments where there are multiple layers of pulp base material 12, the porosity may range from 0.01 Gurley second—20 Gurley seconds. The volatile composition 24 may be applied to the base material 12 in the form of a film or a coating, or as a treatment integrated into the internal structure 20 of the base material 12. The difference in porosities affects the release rate of the volatile composition 24, as the lower porosity has a lower release rate, whereas the higher porosity has a higher release rate. Having a higher porosity in one portion of the base material 12 (such as inner layer or inner ply) compensates for the fact that the volatile composition 24 has to travel through more layers/plies to reach the outside of the base material 12. It is also noted that the density of the base material 12 affects the internal reservoir of the base material 12 (i.e., the capacity to absorb the volatile composition 24).

In some embodiments, different thicknesses of the base material 12 may have different amounts of compression applied during the manufacturing process such that the resultant base materials 12 may have varying densities, porosities, and absorbencies.

Additional description of base materials, porosity, pulp concentrations, etc. may be found in U.S. Publication No. 2011/0262377, the entire contents of which is incorporated herein by reference.

In certain embodiments, the porosity of the pulp base material 12 may be controlled such that the pulp base material 12 is configured with varying porosity zones 1202. In some embodiments, the porosity zones 1202 may be formed by changing the compactness of the fibers within the pulp base material 12.

For example, the pulp base material 12 may be formed within a mold 1204, as shown in FIG. 1. The mold 1204 is configured to form a pulp base material 12 having at least one high porosity zone 1206 and at least one low porosity zone 1208.

The pulp base material 12 positioned over the portion of the mold 1204 having a plurality of apertures 1209 in the base surface comprises the low porosity zone 1208. When pressure is uniformly applied to the pulp base material 12, more water is removed from that zone of the pulp base material 12 via the drainage apertures 1209. As a result, the low porosity zone 1208 will have greater fiber compactness (and thus a greater density).

In contrast, the pulp base material 12 positioned over the portion of the mold 1204 with the solid base surface comprises the high porosity zone 1206. When pressure is uniformly applied to the pulp base material 12, less water is removed from that zone of the pulp base material 12 because there is no additional drainage mechanism to assist with water removal. As a result, the high porosity zone 1206 will have less fiber compactness (and thus a lower density).

Figure 2:
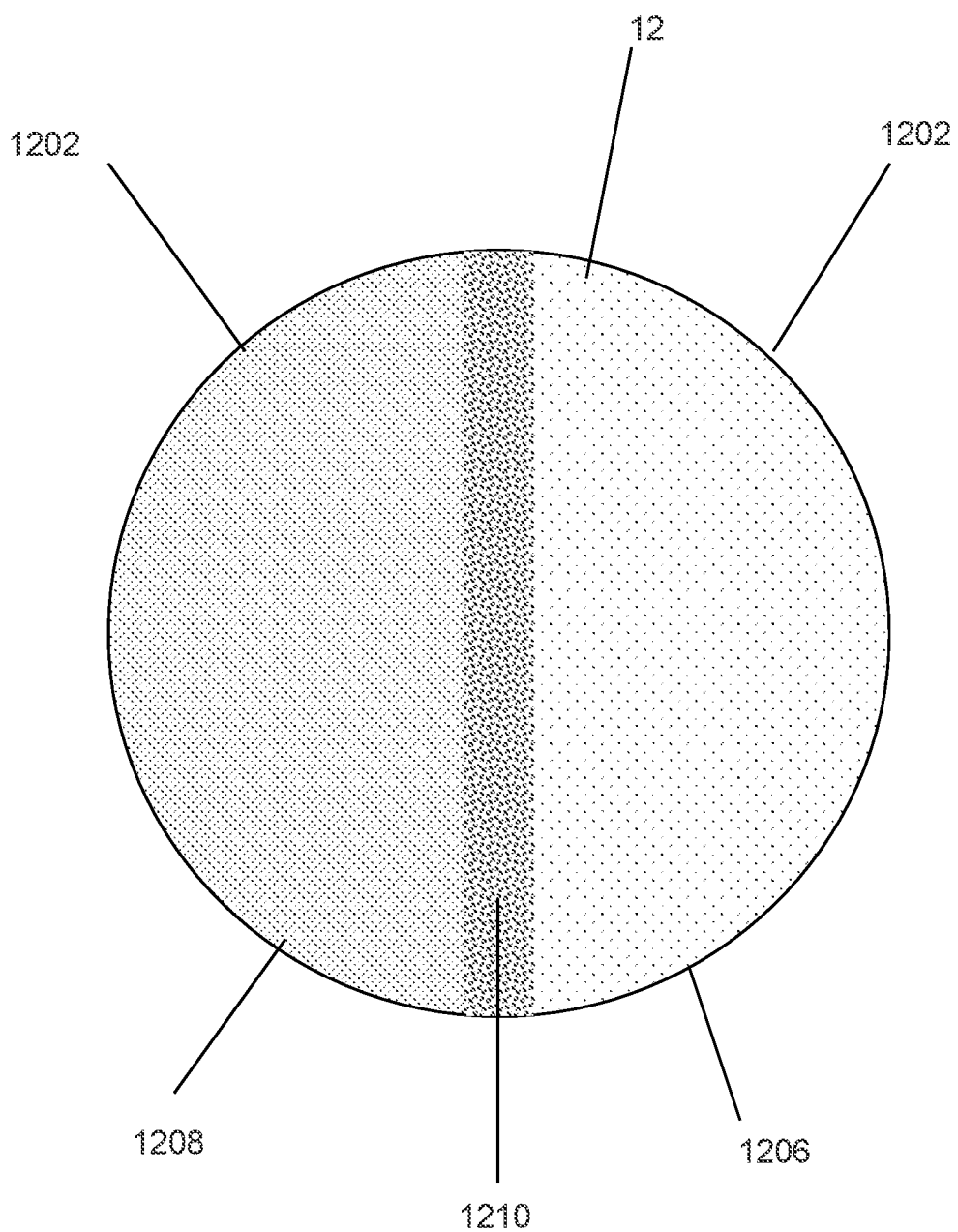
FIG. 2 is a top view of the pulp base material formed with the mold of FIG. 1.
Figure 3:
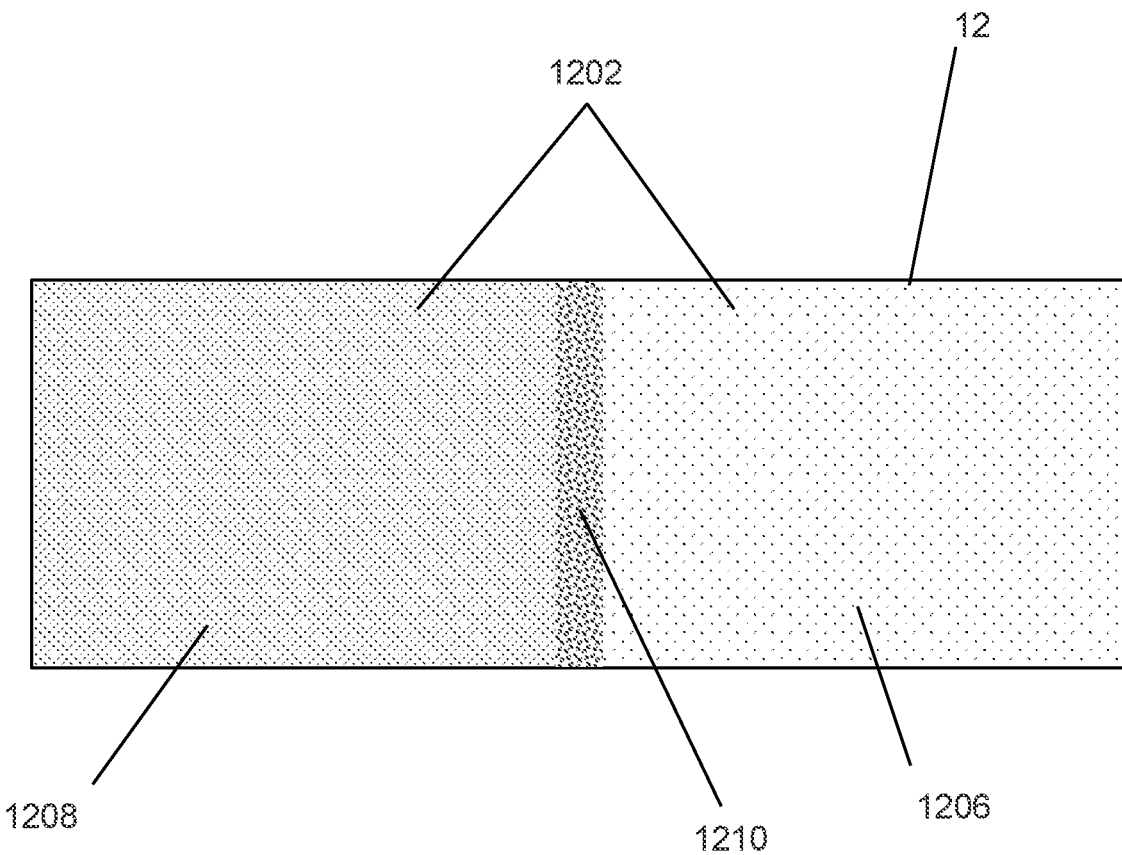
FIG. 3 is a side view of the pulp base material of FIG. 1.
Figure 4:
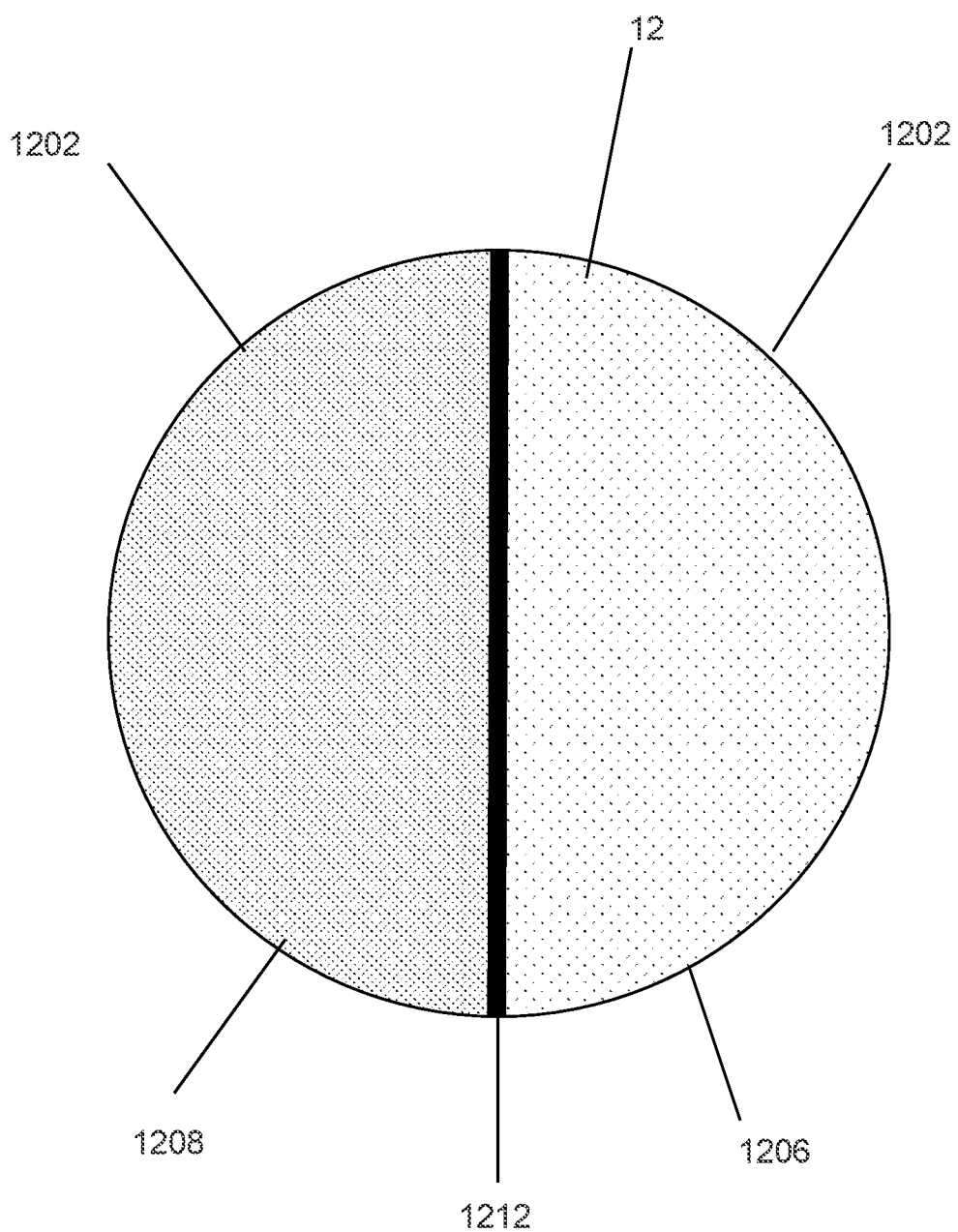
FIG. 4 is a top view of a pulp base material formed with a divider, according to certain embodiments of the present invention.

As best illustrated in FIGS. 2-3, there may be transitional porosity zones 1210 between the high porosity zone 1206 and the low porosity zone 1208, in which the fiber compactness gradually changes. When the volatile composition(s) 24 are infused into zones 1206, 1208 of the pulp base material 12, a certain amount of wicking of the volatile composition(s) 24 may occur through the transitional porosity zones 1210.

In further embodiments, as best illustrated in FIGS. 4-9, a divider 1212 may be positioned, or at least partially embedded within the pulp base material 12. To position the divider 1212 within the pulp base material 12, the divider 1212 may be positioned within the mold 1204 when the pulp composition is introduced into the mold 1204. The divider 1212 may be shaped to separate the zones 1206 and 1208 so as to eliminate some or substantially all of the transitional porosity zones 1210, as well as some or substantially all of the wicking of the volatile composition 24 between the various porosity zones 1202.

In some embodiments, the pulp base material 12 with a lower concentration of pulp fibers may be added to the high porosity zone 1206, and the pulp base material 12 with a higher concentration of pulp fibers may be added to the low porosity zone 1208. When pressure is uniformly applied to the mold 1204, the high porosity zone 1206 will have less fiber compactness (and thus a lower density) than the low porosity zone 1208. When pressure is applied to compact the mold 1204 to a uniform distance, the low porosity zone 1208 will have greater fiber compactness (and thus a higher density) due to a greater number of fibers per volume, than the high porosity zone 1206.

Alternatively, a pulp base material 12 having a uniform concentration of pulp fibers may be added to both zones 1206, 1208. More pressure may be applied to the low porosity zone 1208, thereby compressing it more to reduce the porosity (i.e., by compacting the fibers more and increasing the density). In contrast, less pressure may be applied to the high porosity zone 1206, thereby compressing it less than the low porosity zone 1208.

Figure 5:
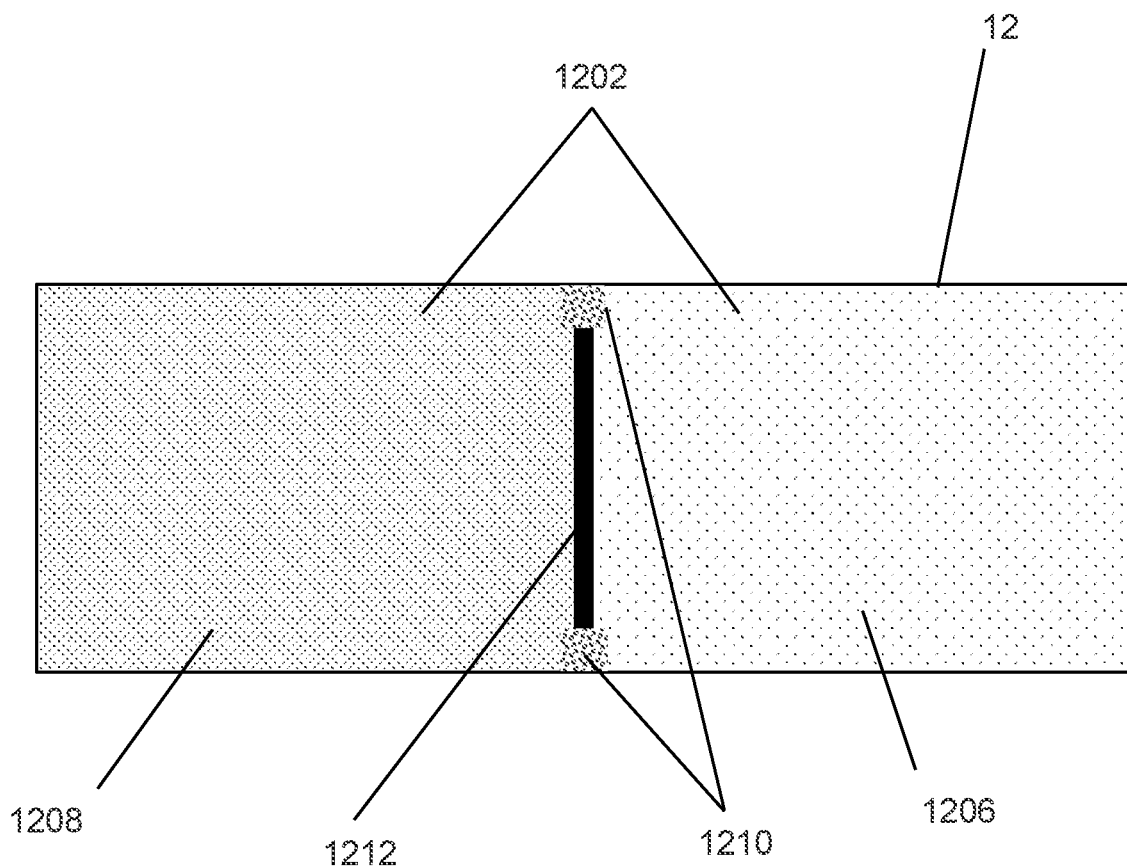
FIG. 5 is a side view of a pulp base material formed with a divider in which the top and bottom surfaces of the divider are covered by pulp material, according to certain embodiments of the present invention.
Figure 6:
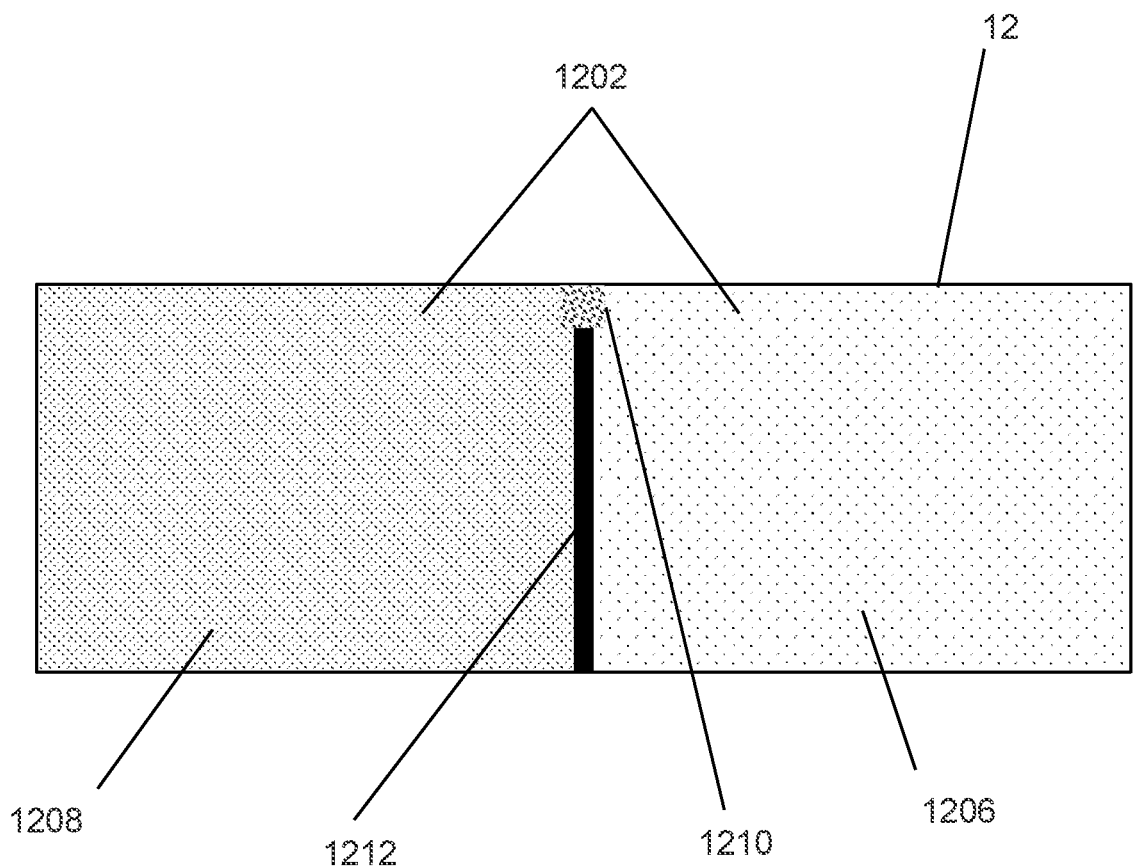
FIG. 6 is a side view of a pulp base material formed with a divider in which the top surface of the divider are covered by pulp material, according to certain embodiments of the present invention.
Figure 7:
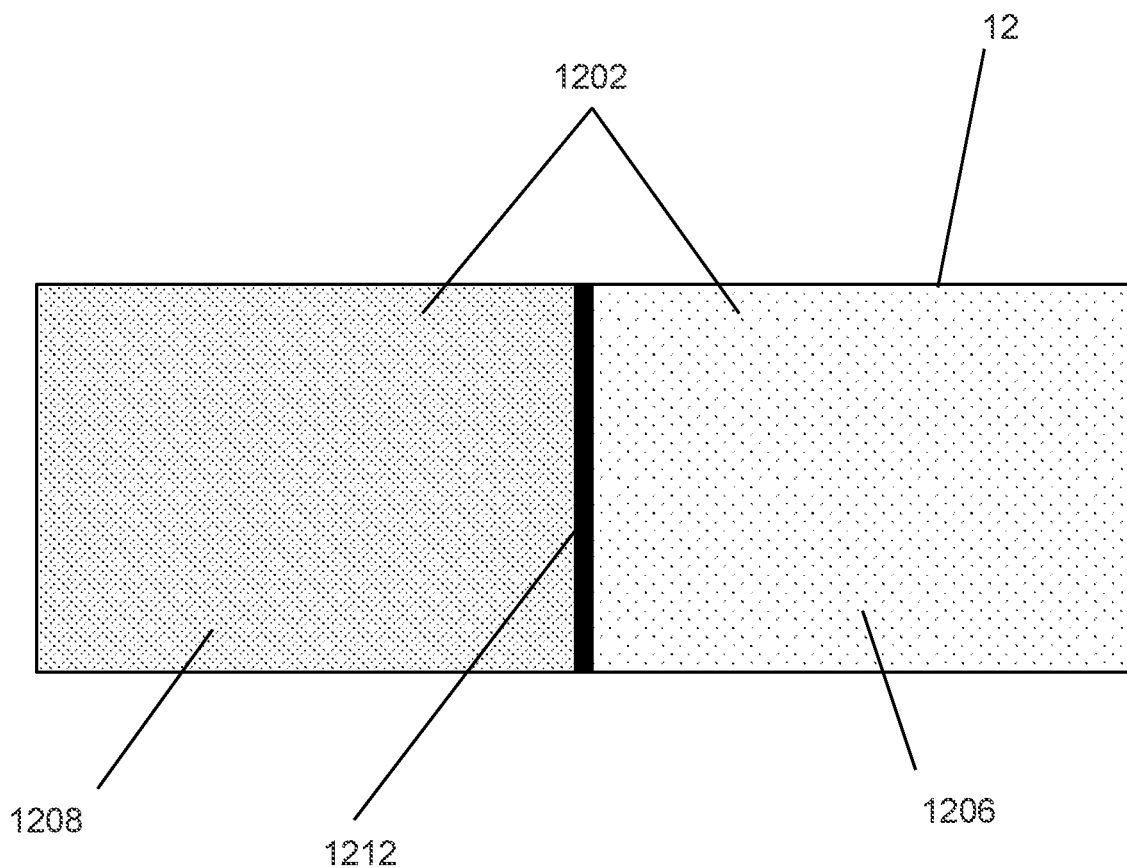
FIG. 7 is a side view of a pulp base material formed with a divider in which the top and bottom surfaces of the divider are not covered by pulp material, according to certain embodiments of the present invention.

As best illustrated in FIGS. 5-6, the divider 1212 may be shaped so as to be at least partially embedded within the pulp base material 12. In these embodiments, a portion of the pulp base material 12 may extend over an upper (FIGS. 5-6) and/or lower (FIG. 6) surface of the divider 1212 so that the divider 1212 is not visible through the overlapping pulp base material 12. When the volatile composition(s) 24 are infused into zones 1206, 1208 of the pulp base material 12, a certain amount of wicking of the volatile composition(s) 24 may occur through the overlapping pulp base material 12.

In other embodiments, as best illustrated in FIGS. 4 and 6-9, the divider 1212 may be shaped so as to form at least a portion of a visible surface of the article 10. In these embodiments, the divider 1212 may be shaped so as to form a portion of a decorative design or other aesthetically appealing surface treatment of the article 10.

In further embodiments, the porosity zones 1202 may be formed by introducing varying amounts of a pore-forming agent such as a gas or gas-forming material. The gas or gas-forming material may be introduced into the pulp base material 12 prior to or after introduction into the mold 1204. Examples of gas-forming materials include solids, volatile liquids, chemical reagents, such as calcium carbonate and acid, thermally decomposable materials which will cause evolution of a gas by, for example, decomposition of bicarbonate, or biological agents, such as dextrose and yeast. Different amounts of gas or gas-forming materials may be introduced into each zone 1206, 1208, thereby producing zones with differing porosities, even if the fiber content of each zone is approximately the same. For example, the high porosity zone 1206 may be infused with a larger amount of a gas or gas-forming material, thereby having a greater porosity, while the low porosity zone 1208 may be infused with a lesser amount of a gas or gas-forming material, thereby having a lower porosity.

In further embodiments, zones 1206 and 1208 may be formed in completely separate molds 1204 using any of the above techniques (i.e., fiber compactness, infusion of gas or gas-forming materials, refining, additives, or any other porosity-controlling method described above) to adjust the porosity of zone 1206 relative to the porosity of zone 1208.

Figure 10:
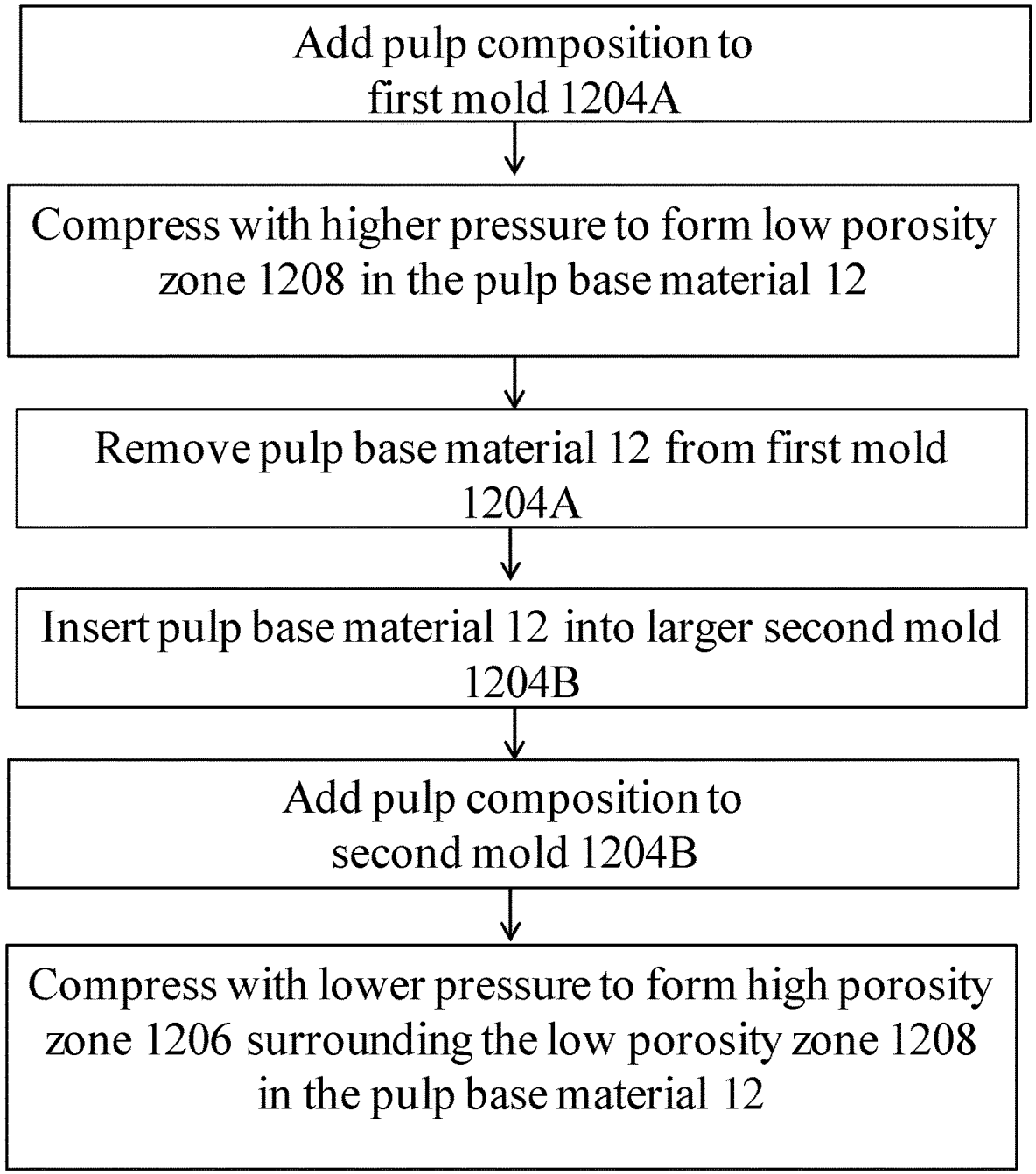
FIG. 10 is a flow diagram of a multi-step molding process, according to certain embodiments of the present invention.
Figure 11:
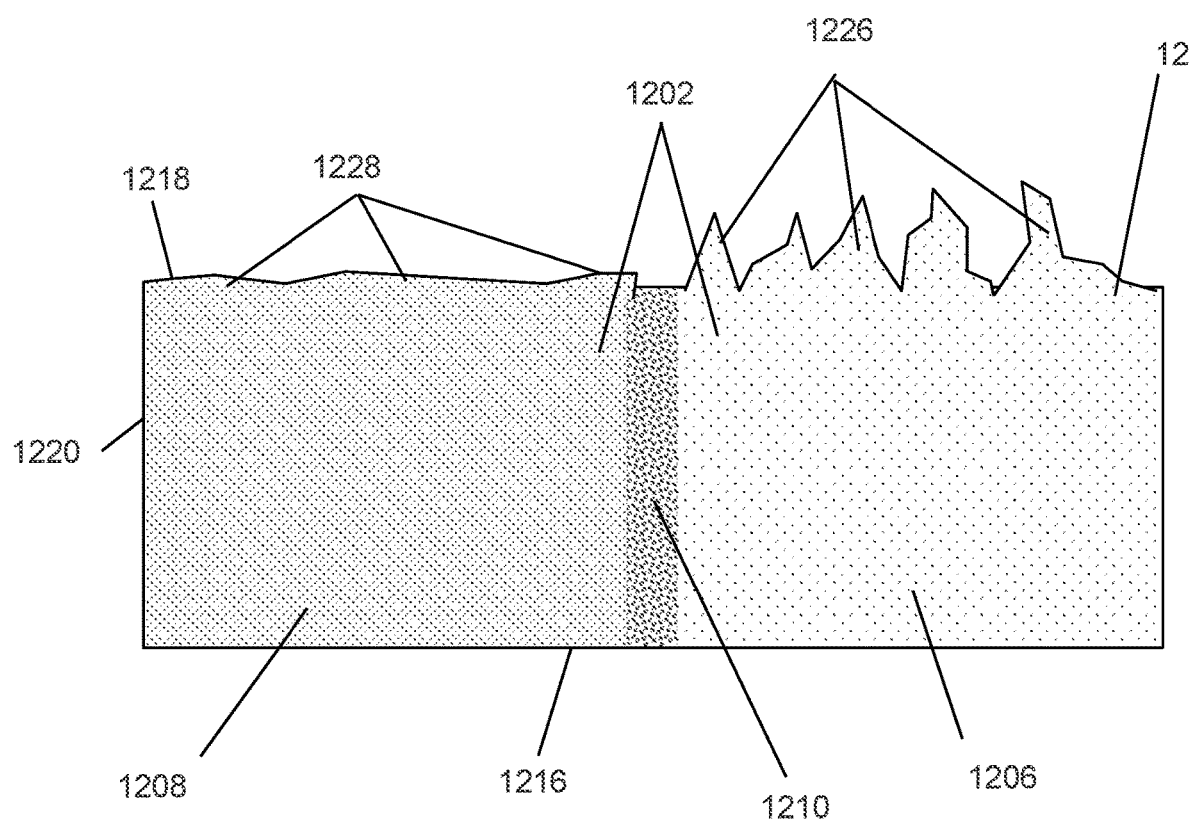
FIG. 11 is a side view of a pulp base material formed with complex surface geometry, according to certain embodiments of the present invention.
Figure 12:
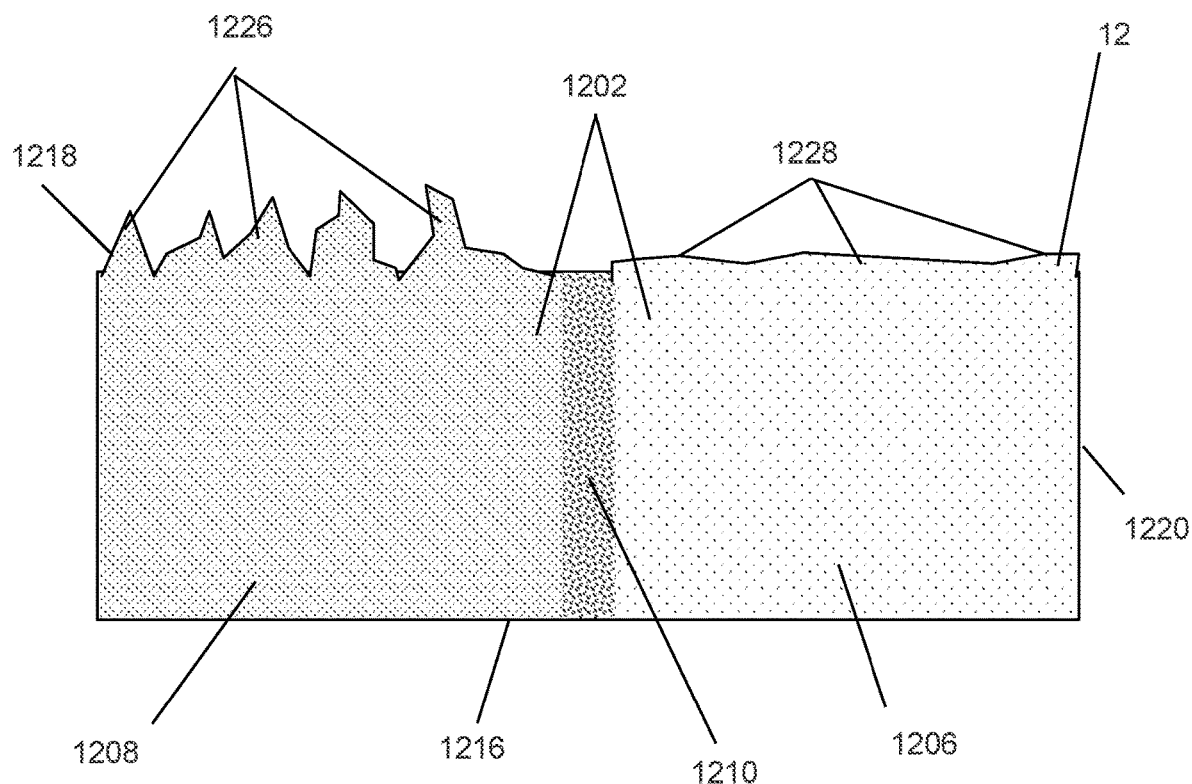
FIG. 12 is a side view of a pulp base material formed with complex surface geometry, according to certain embodiments of the present invention.
Figure 13:
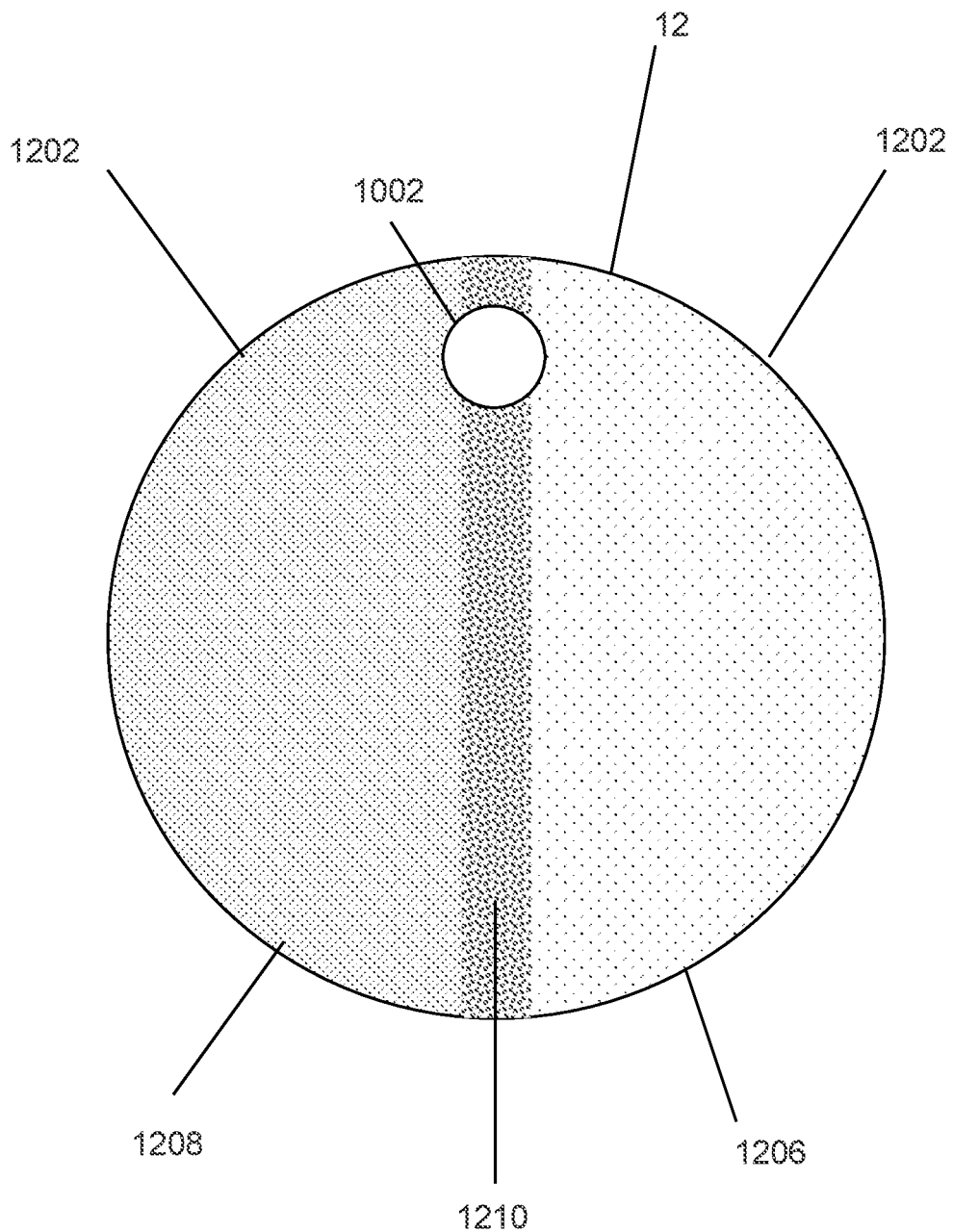
FIG. 13 is a top view of a pulp base material formed with an attachment element, according to certain embodiments of the present invention.
Figure 14:
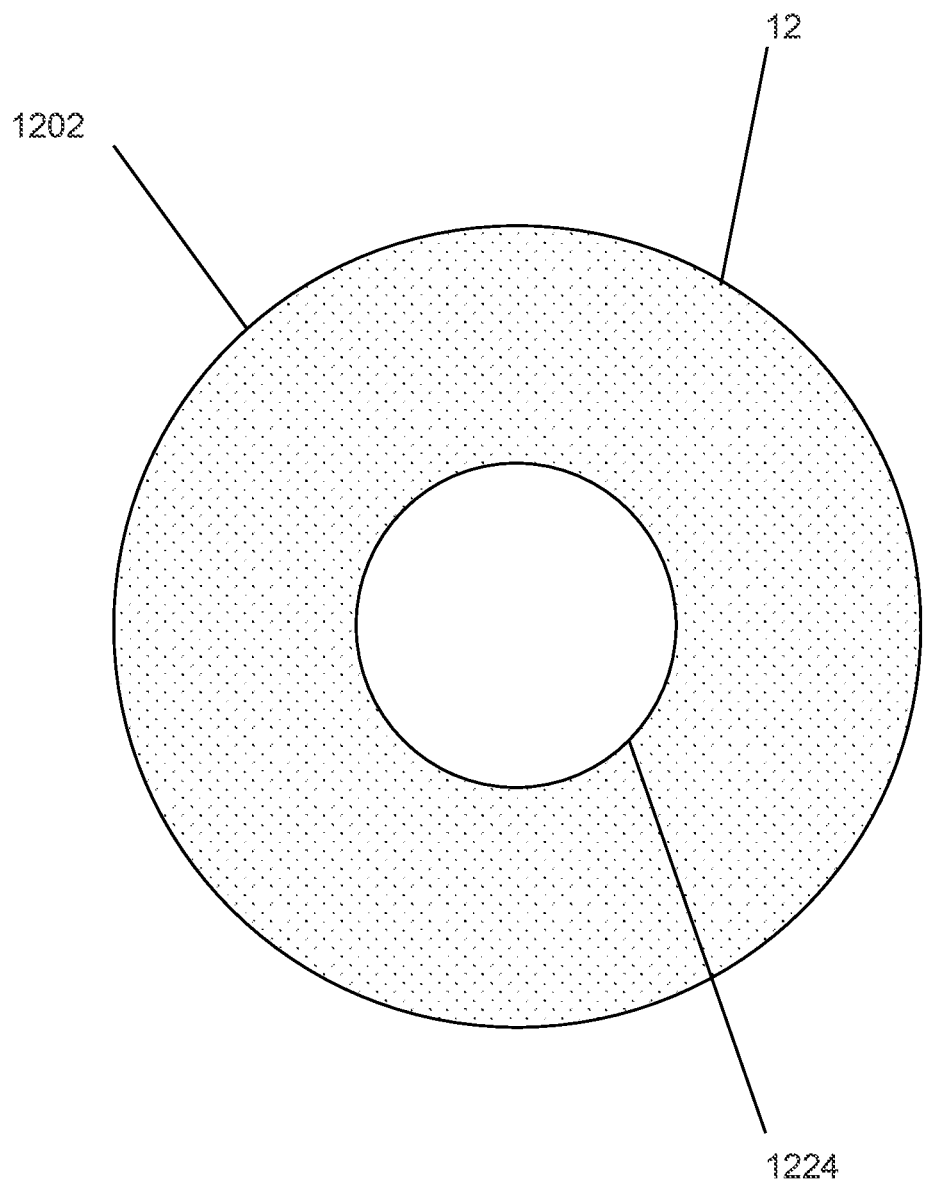
FIG. 14 is a top view of a pulp base material formed with an opening, according to certain embodiments of the present invention.

Furthermore, as described in FIG. 10, the pulp base material 12 may be formed using at least two molding steps. In the first step, pulp composition is added to a first mold 1204A, which is then compressed using a higher pressure (in the range of 0.1 lb/in$^2$ to 100 lb/in$^2$) to form the low porosity zone 1208. The pulp base material 12 is removed from the first mold 1204A, and then inserted into a second mold 1204B having a larger volume than the first mold 1204A. Additional pulp composition is then added to the second mold 1204B to surround the pulp base material 12 from the first mold 1204A. The material inside mold 1204B is then compressed using a lower pressure (in the range of 0.1 lb/in$^2$ to 100 lb/in$^2$) to form the high porosity zone 1206. This technique forms a pulp base material 12 having discrete porosity zones 1202 without the transitional porosity zones 1210 forming between the porosity zones 1202 and also without the need for a divider 1212 to separate the zones. Additionally, a treatment may be applied to the low porosity zone 1208 before additional pulp composition is added to the second mold 1204B to maintain the shape and/or density of the low porosity zone 1208 after addition of the additional pulp composition. Examples of the treatment include, but are not limited to wet strength agents, binders, wax, starch, sizing, cross-linking reagents, and/or any other suitable agent.

In the embodiments where the divider 1212 is shaped so as to completely eliminate any overlapping pulp base material 12 between the zones 1206, 1208 and/or where the zones 1206, 1208 are formed in different molds, joining mechanisms 1214 between the zones 1206, 1208 may be used to discrete units of the pulp base material 12 into the article 10, as illustrated in FIGS. 17-18, 30A, 31-32, and 40.

Examples of suitable joining mechanisms 1214 may include but are not limited to any suitable chemical fasteners such as adhesives, coatings, wax, starch, and gums, and/or any suitable mechanical fasteners such as male/female clips, anchors, hook and loop fasteners, pins, screw-type fasteners, impregnation-type fasteners, and magnets. These mechanical fasteneres may, in certain embodiments, be part of the molding process itself and may be made out of pulp.

Figure 17:
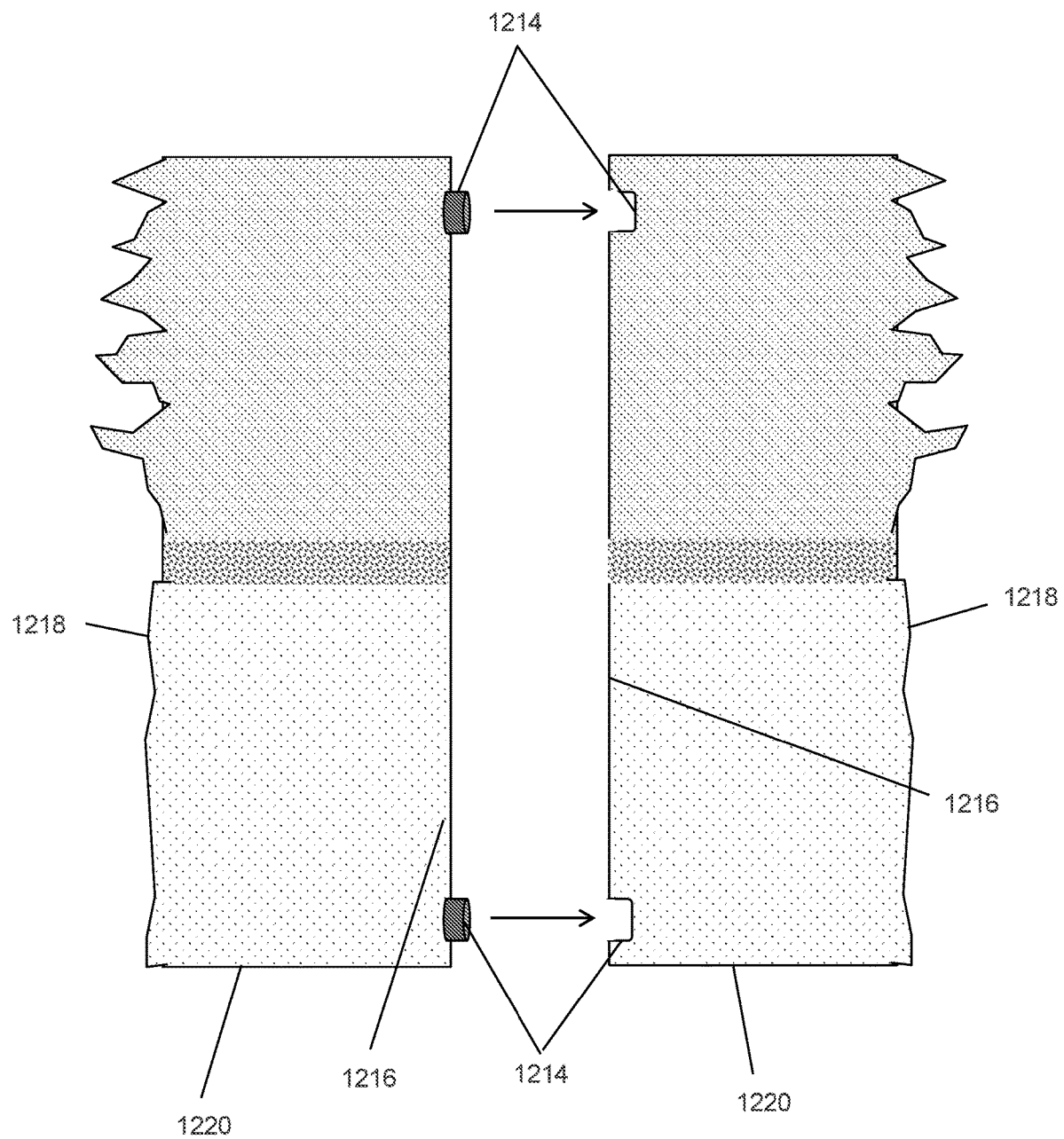
FIG. 17 is a side view of two pulp base materials being joined, according to certain embodiments of the present invention.
Figure 18:
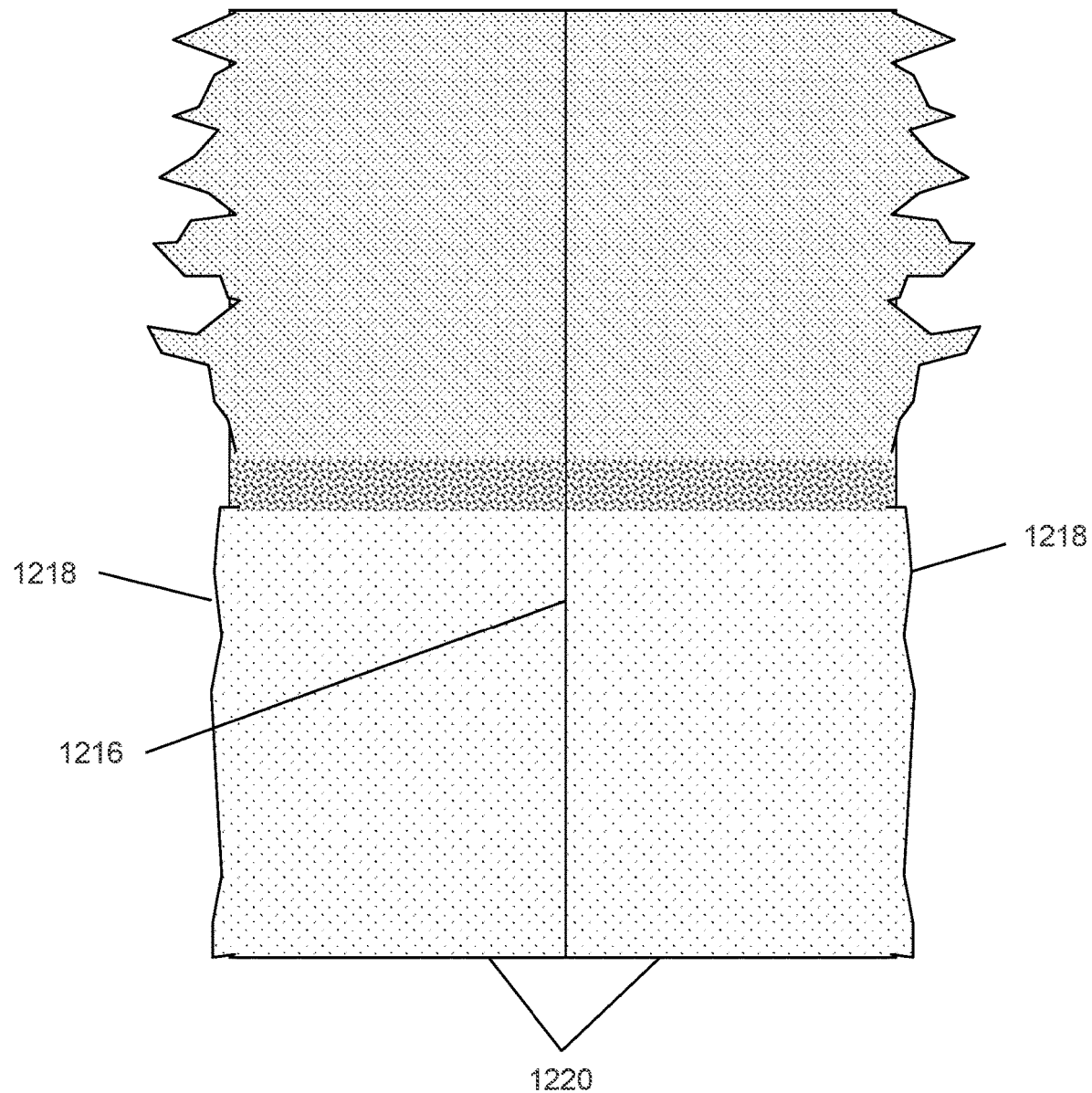
FIG. 18 is a side view of the two pulp base materials of FIG. 17 joined.

FIG. 17 illustrates an example of joining mechanisms 1214 that may be used. In certain embodiments, the joining mechanisms 1214 may be included in the mold when the pulp base material 12 is formed. In other embodiments, the joining mechanisms 1214 may be added to the zones 1206, 1208 after the molding process is completed.

Figure 9:
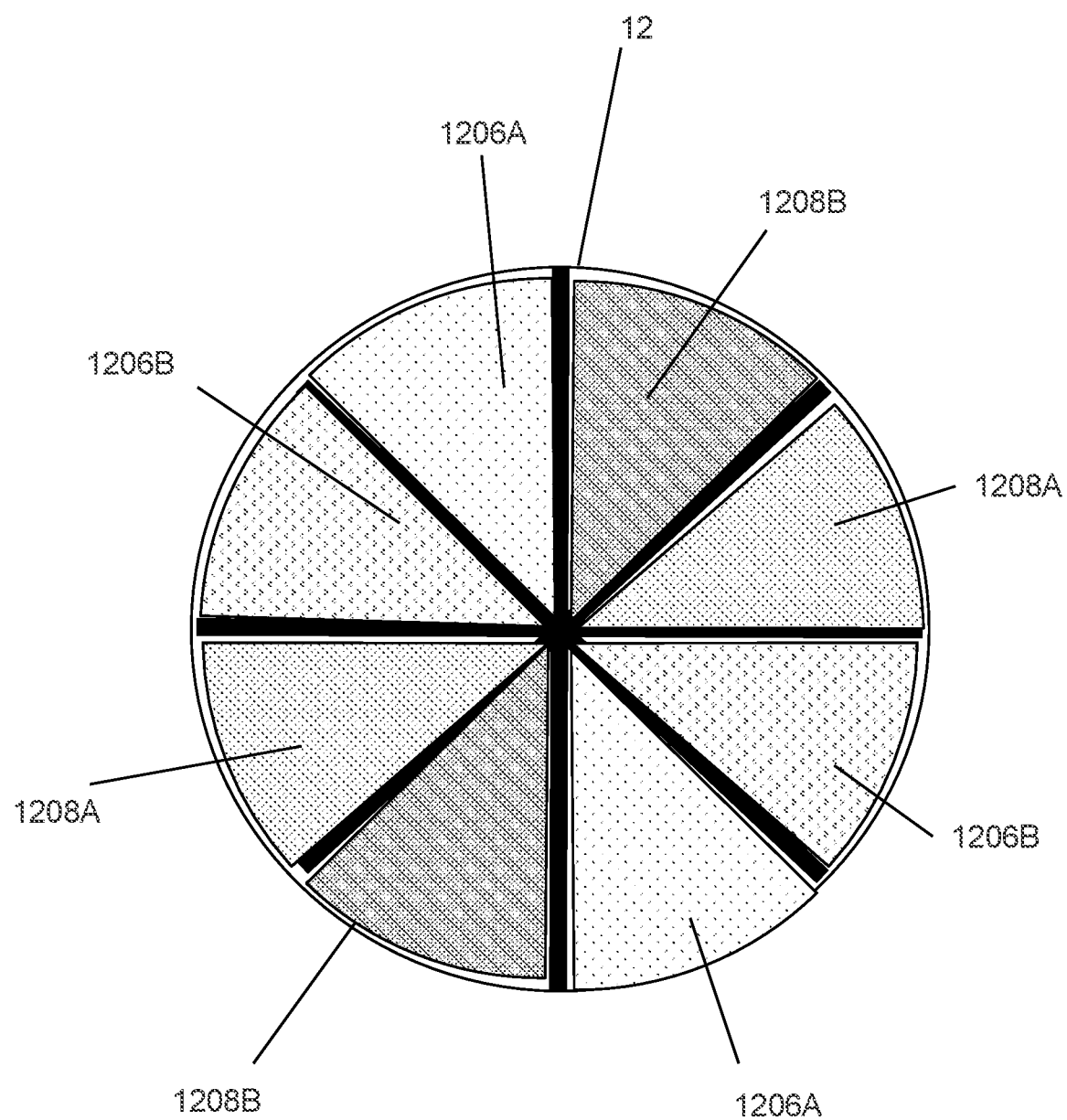
FIG. 9 is a top view of a pulp base material formed with a divider comprising multiple zones, according to certain embodiments of the present invention.

While the above description of the pulp base material 12 focused on two porosity zones 1206, 1208, the embodiments are by no means so limited. For example, the above techniques and mechanisms may be used to form a pulp base material 12 having any suitable number of zones, including but not limited to three, four, five, six, or more zones. As illustrated in FIG. 9, the pulp base material 12 may include eight zones: zones 1206A having the highest porosity, 1206B having high porosity, 1208A having low porosity, and 1208B having the lowest porosity.

Furthermore, the zones may have any suitable shape, which includes but is not limited to wedge or pie shapes, rectilinear, elliptical, circular, or any suitable type of simple or complex geometry. Furthermore, while the zones 1206, 1208 have been described as being formed with different porosities, the person of ordinary skill in the relevant art will understand that the zones 1206, 1208 may be formed of the same or similar porosities using any of the forming or joining techniques discussed above.

Furthermore, as best illustrated in FIGS. 2 11-12, 17-18, 30A, 31-32, and 40, the zones may be formed with a relatively smooth interlocking surface 1216 for joining with other zones, while also having a very rough or complex exterior-facing surface 1218 that may include many peaks 1226 that form the outer surface of the pulp base material 12.

Figure 71:
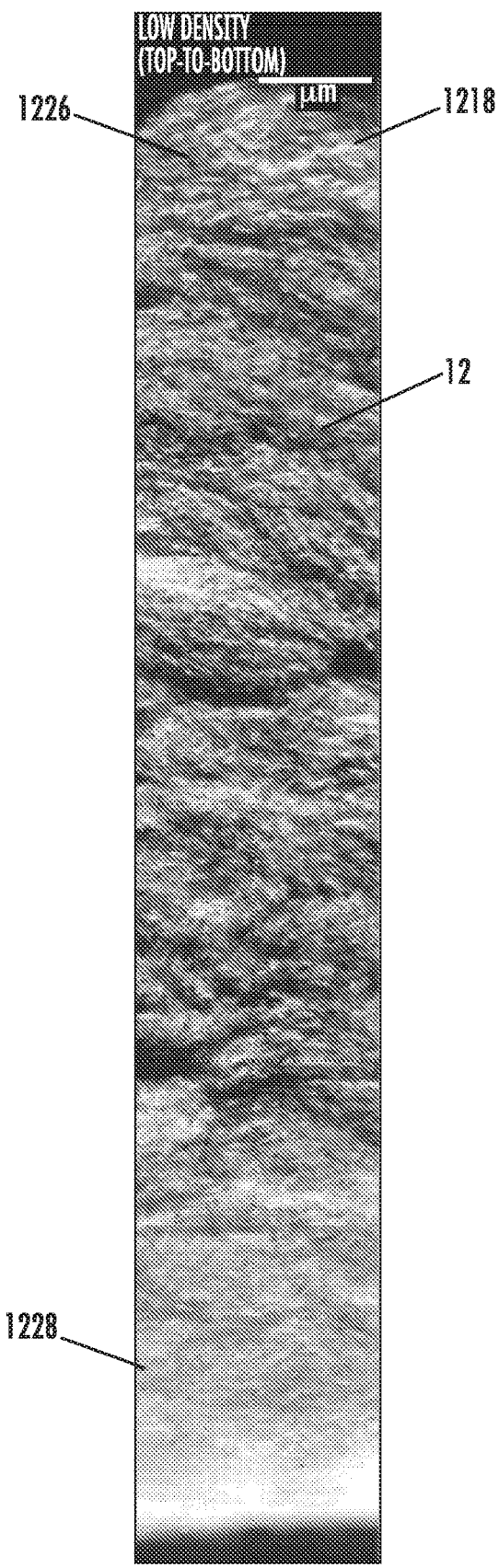
FIG. 71 is a high resolution image of the cross-section of the low density sample of FIG. 69.
Figure 72:
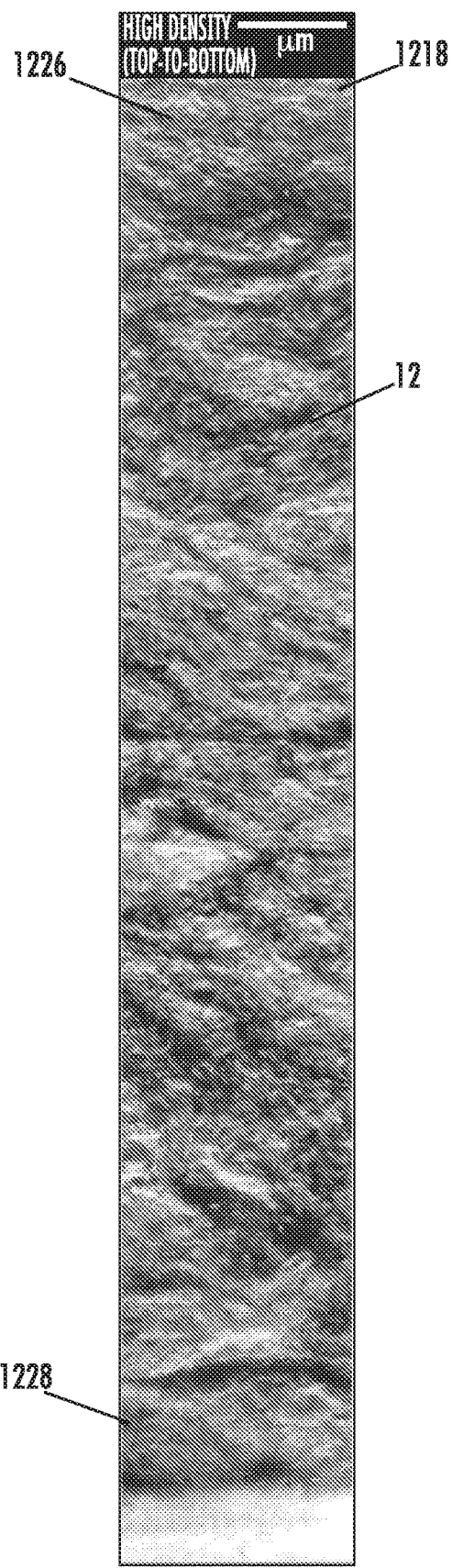
FIG. 72 is a high resolution image of the cross-section of the high density sample of FIG. 70.

In some embodiments, the complex geometry of the exterior-facing surface 1218 may provide additional release rate control. For example, as shown in the attached microphotographs in FIGS. 71 and 72, the pulp base material 12 contains mini-variations in pulp compositions that are located within peaks 1226 that are located on the surface 1218. The shape of the peaks 1226 causes the pulp fibers to become more highly concentrated at a micro-scale in these areas, whereas the valleys or flatter regions 1228 are configured for better pulp fiber dispersion at a micro-scale. As a result, there are variations in release rates from peak areas 1226 as compared to the flatter regions 1228. Additionally, as explained in more detail below, the different surface areas of the peaks 1226 and the valleys or flatter regions 1228 will also provide release rate control. Thus, the surface geometry may be configured to provide more peaks 1226 within the zone 1206 to further enhance the release rate of the "base notes," while using a smoother surface texture within zone 1208 to further regulate the release rate of the "top notes." Thus, the release rate can be tailored by density and/or surface area differences.

The location and concentration of the peaks 1226 also enhances the directionality of the release of the volatile composition 24. For example, the peaks 1226 act as small three-dimensional emitters, thus allowing the volatile composition 24 to emit from the raised surface of the peak 1226 in all directions. In contrast, the flatter regions 1228 tend to emit in more limited directionality because there is less surface area that faces in a range of directions. The range of emitting directionality provided by the peaks 1226 and flatter regions 1228 may be optimized and tied with locations of certain volatile compositions 24 within the pulp base material 12. The surface geometry may be designed to work in conjunction with porosity zones 1202 and/or with a pulp base material 12 having a relatively uniform porosity.

In some embodiments, as illustrated in FIGS. 20-26, 28-29, 30A-30B, 35, 59-64, and 73-76, the article 10 may include an attachment element 1002 for attaching the article 10 to another article or to other objects, such as a portion of any form of transportation (such as a cabin of a car, plane, train, boat, etc.), a Christmas tree or other real or artificial ornamentation or decoration, a fixture in a home or office, or a body. Such an attachment element 1002 may comprise a hole within the pulp base material 12 through which a hook, clip, loop, string, prongs, band, magnet, or other mechanisms for attaching an article to a surface, another article, or another structure may be inserted or otherwise coupled to the article 10. In other embodiments, the article 10 may comprise an attachment element 1002 that is configured to penetrate through at least a portion of the pulp base material 12.

The attachment element 1002 may be formed in or attached to the article 10 after the pulp base material 12 has been molded. The attachment element 1002 may also be connected to or formed as part of the divider 1212 or other structure that is placed into the mold 1204 with the pulp composition so that the attachment element 1002 is at least partially embedded within the pulp base material 12.

In some embodiments, as best illustrated in FIGS. 11-12, 17-18, 24-25, 31, the article 10 may include an externally-facing smooth surface 1220 that forms a support surface to hold the article 10 in an upright position when positioned on another surface such as a table, desk, counter, window sill, etc.

In certain embodiments, as best illustrated in FIGS. 23, and 35-44, a stand 1006 may be configured to couple to the article 10. The stand 1006 may be formed of any material that does not absorb or transmit the volatile composition 24 so as to prevent contact between the article 10 and other surfaces. Suitable materials include, but are not limited to metal, metalized films, ceramic, glass, glazed ceramics, plastic, polymers, and any other impervious material.

In other embodiments, as best illustrated in FIGS. 8, 24-27, and 29, the article 10 may include a backing layer 1222 that is applied to at least one surface of the article 10. The backing layer 1222 may be formed of any material that does not absorb or transmit the volatile composition 24 so as to prevent contact between the article 10 and other surfaces. Suitable materials include but are not limited to metal, metalized films, ceramic, glass, glazed ceramics, plastic, polymers, and any other impervious material.

The backing layer 1222 may be applied to the article 10 after the pulp base material 12 has been molded using any suitable chemical fasteners such as adhesives, coatings, wax, starch, gum and/or any suitable mechanical fasteners such as snap-fit design, male/female clips, anchors, hook and loop fasteners, pins, screw-type fasteners, impregnation-type fasteners, roughness or compatibility of the surface to bind pulp fibers, and magnets.

Figure 8:
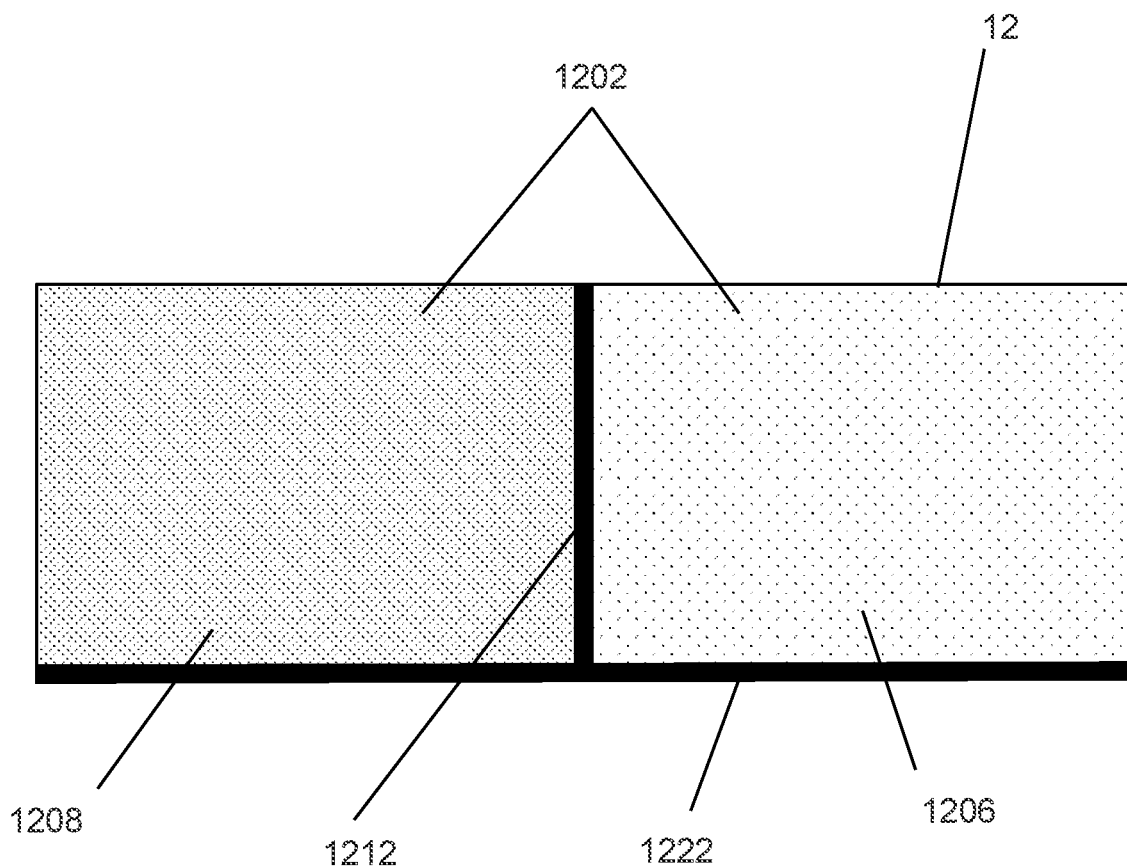
FIG. 8 is a side view of a pulp base material formed with a divider comprising a backing layer, according to certain embodiments of the present invention.

In certain embodiments, as best illustrated in FIG. 8, the backing layer 1222 may also be connected to or formed as part of the divider 1212 or other structure that is placed into the mold 1204 with the pulp composition so that the backing layer 1222 forms an exterior surface of the base pulp material 12.

In further embodiments, as best illustrated in FIGS. 14-16, 21, 41 and 43, the article 10 may further include a dowel or other opening 1224 that extends through a portion of or entirely through the article 10. The opening 1224 may be formed within the pulp base material 12 during the molding process or may be formed in the article 10 using a mechanical tool to form the opening 1224. The opening 1224 may be configured for placement of a light source, such as an light emitting diode or other light source, within the article 10.

Figure 15:
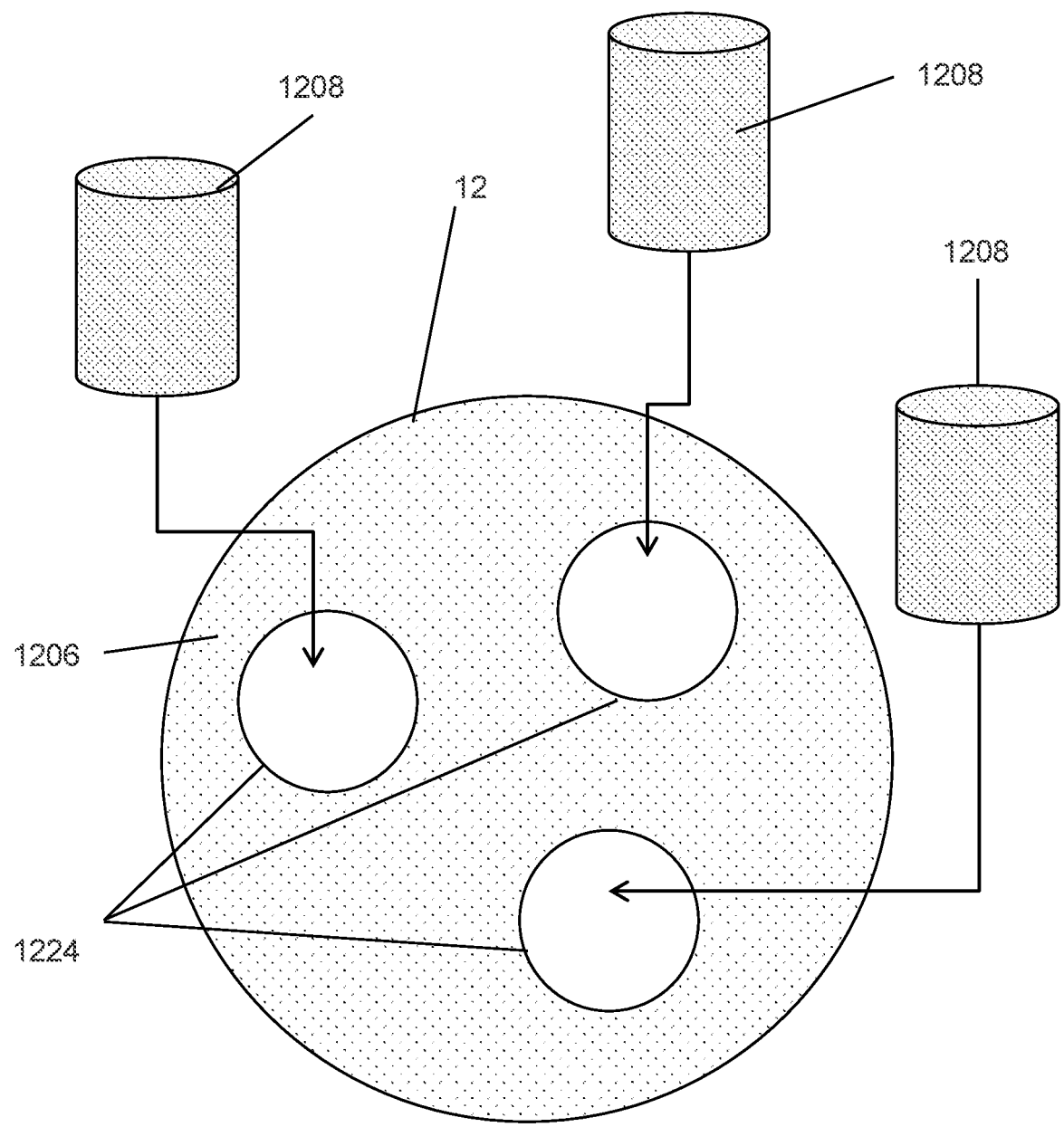
FIG. 15 is a top view of a pulp base material formed with a plurality of openings for addition of other materials, according to certain embodiments of the present invention.
Figure 16:
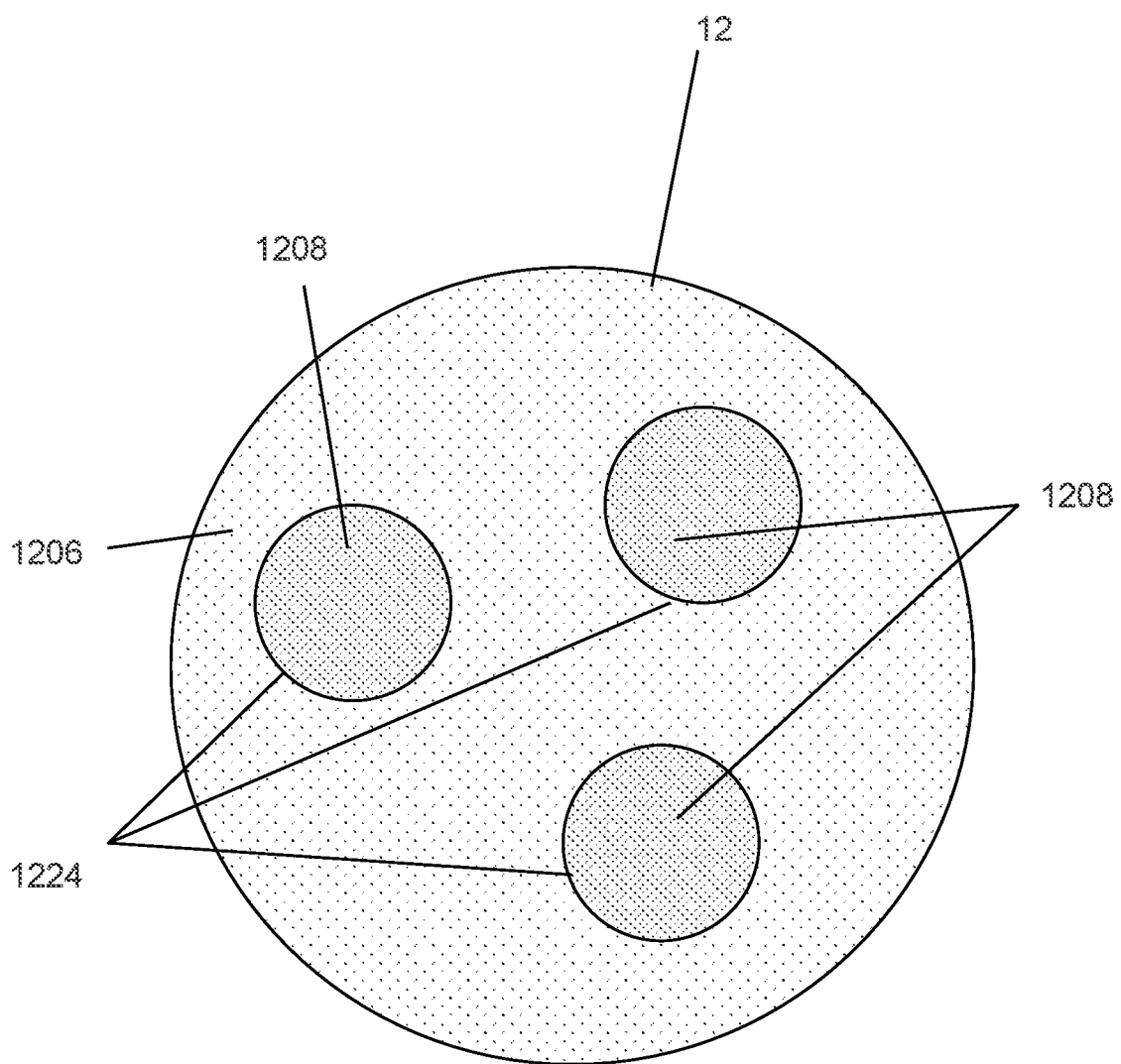
FIG. 16 is a top view of the pulp base material of FIG. 15 with the other materials incorporated into the plurality of openings.

In further embodiments, one or more openings 1224 may form a receptacle for the insertion of other pulp base materials 12 or other materials or objects. For example, as best illustrated in FIGS. 15-16, the pulp base material 12 may be molded having a uniform first porosity without porosity zones 1202 but with at least one opening 1224. This opening 1224 may be shaped to receive another pulp base material 12 that is molded having a uniform second porosity without porosity zones 1202 and having a shape that substantially conforms to the shape and dimensions of the opening 1224. Once the second pulp base material 12 is inserted into the opening 1224, the article 10 may then comprise different porosity zones 1202 resulting from the different porosities of the other pulp base materials 12. Additional openings 1224 may be included with the article 10, and more pulp base materials 12 with additional different porosities may be inserted to form a plurality of porosity zones 1202. In further embodiments, other items such as scented rods of spiral wound paper, may be inserted into the openings 1224. Thus, the openings 1224 may serve as a way to replenish the volatile composition 24 within the article 10 by removing older base materials 12 or scented rods from which the scent has been depleted, and replacing them with new ones.

Figure 19:
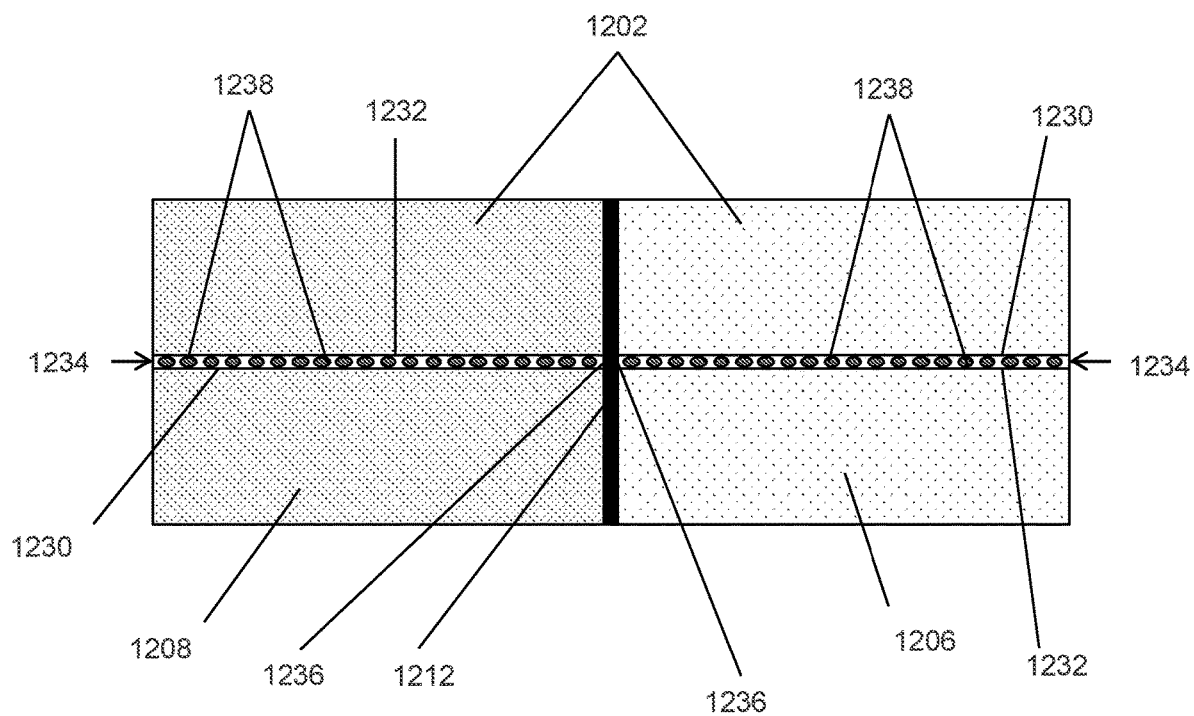
FIG. 19 is a side view of a pulp base material with a capillary system for introduction of volatile compositions into the pulp base material.
Figure 20:
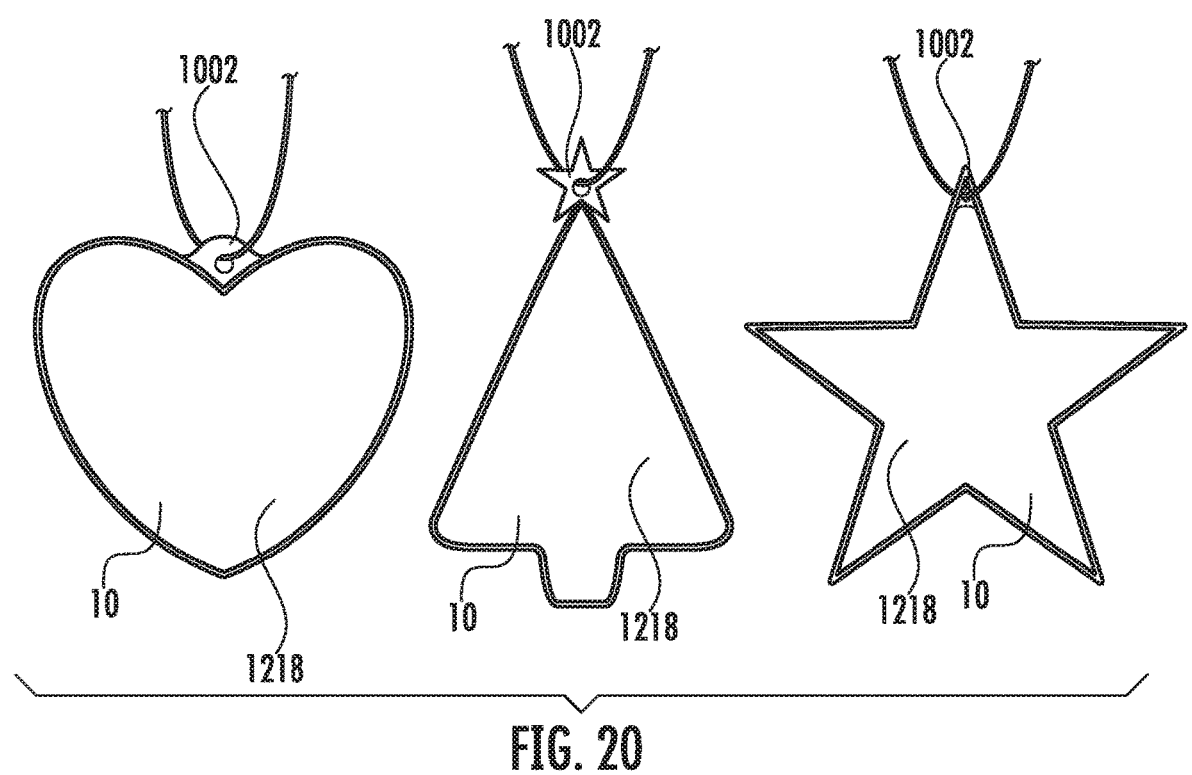
FIG. 20 includes front images of articles with attachment elements and a variety of shapes, according to certain embodiments of the present invention.
Figure 21:
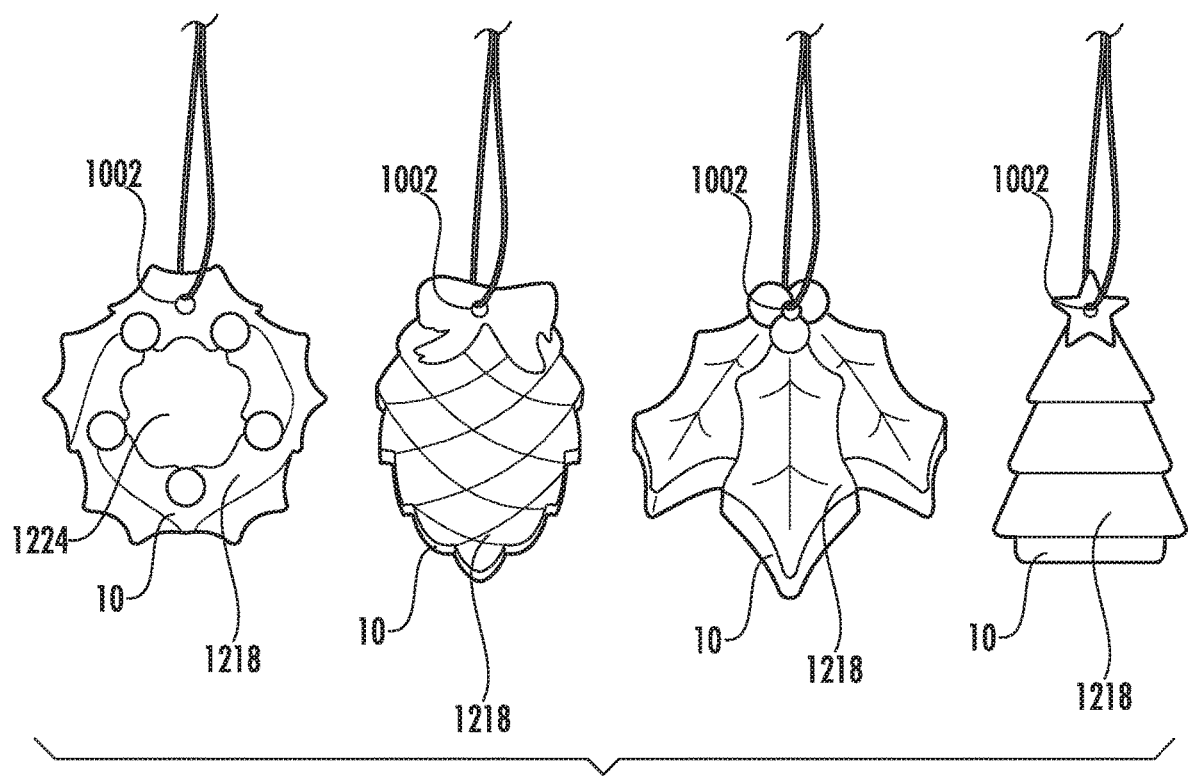
FIG. 21 includes front images of articles with attachment elements and a variety of shapes, according to certain embodiments of the present invention.
Figure 22:
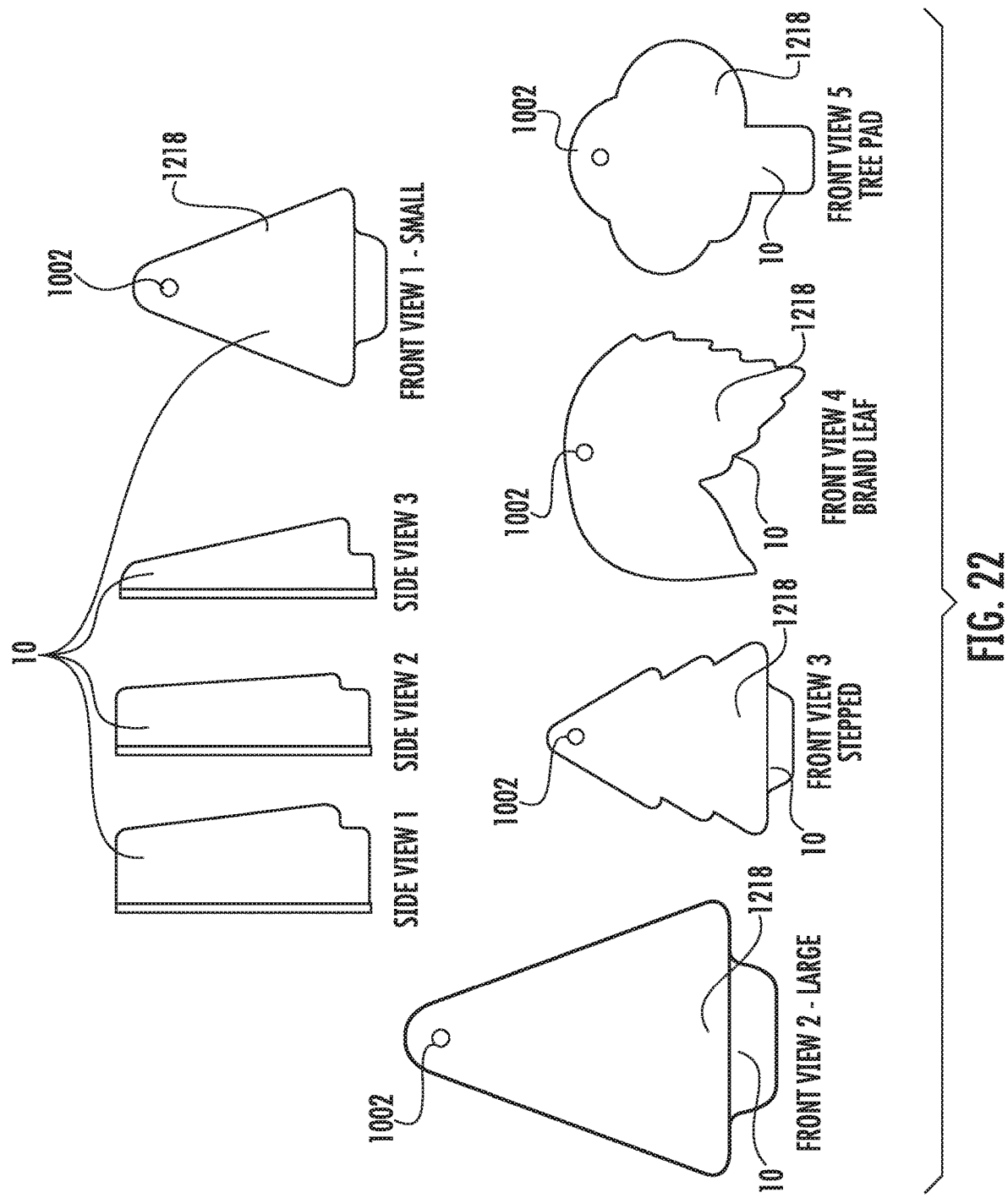
FIG. 22 includes front and side images of articles with attachment elements and a variety of shapes, according to certain embodiments of the present invention.
Figure 23:
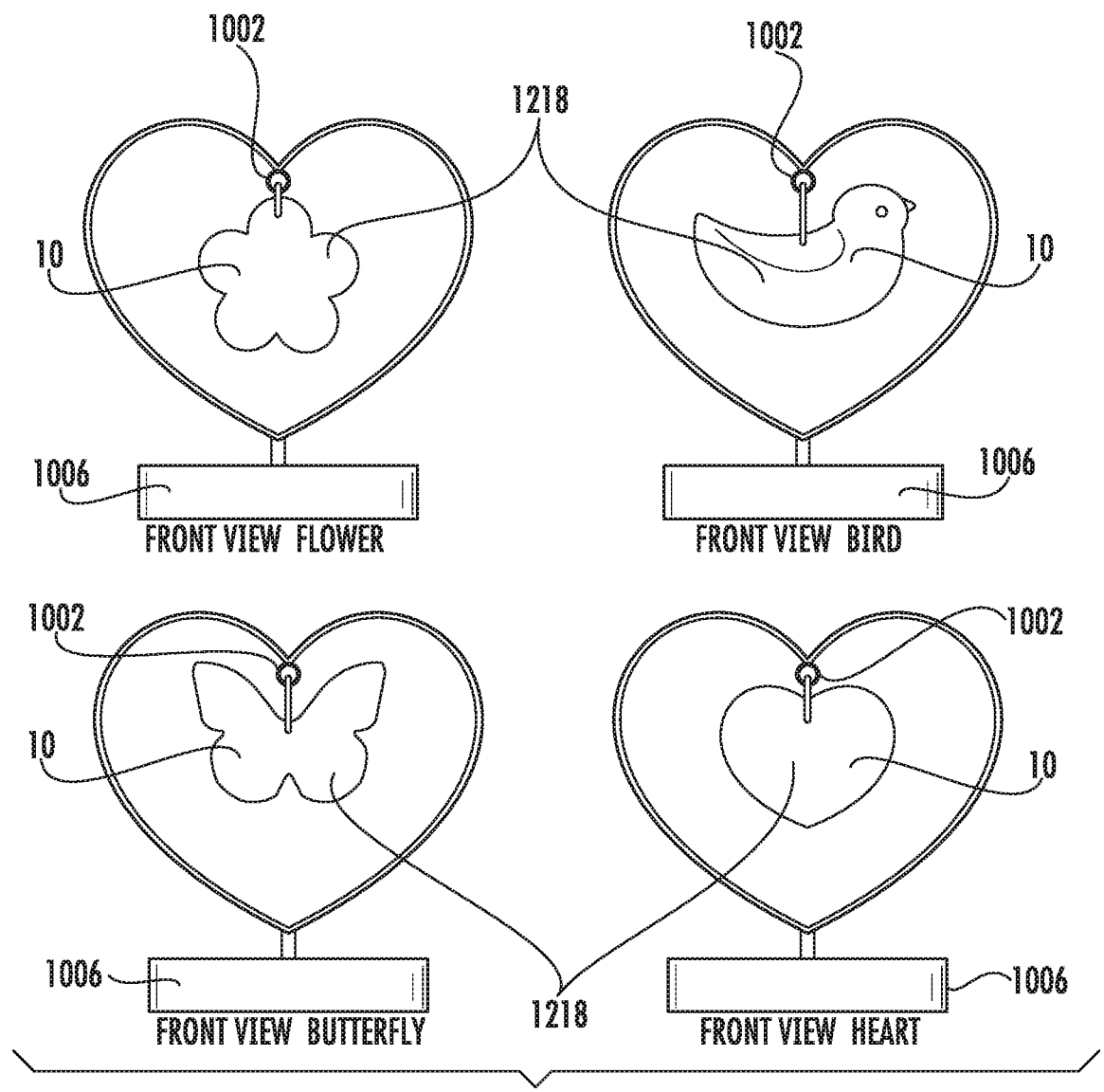
FIG. 23 includes front images of articles with attachment elements that couple the articles to stands, according to certain embodiments of the present invention.
Figure 24:
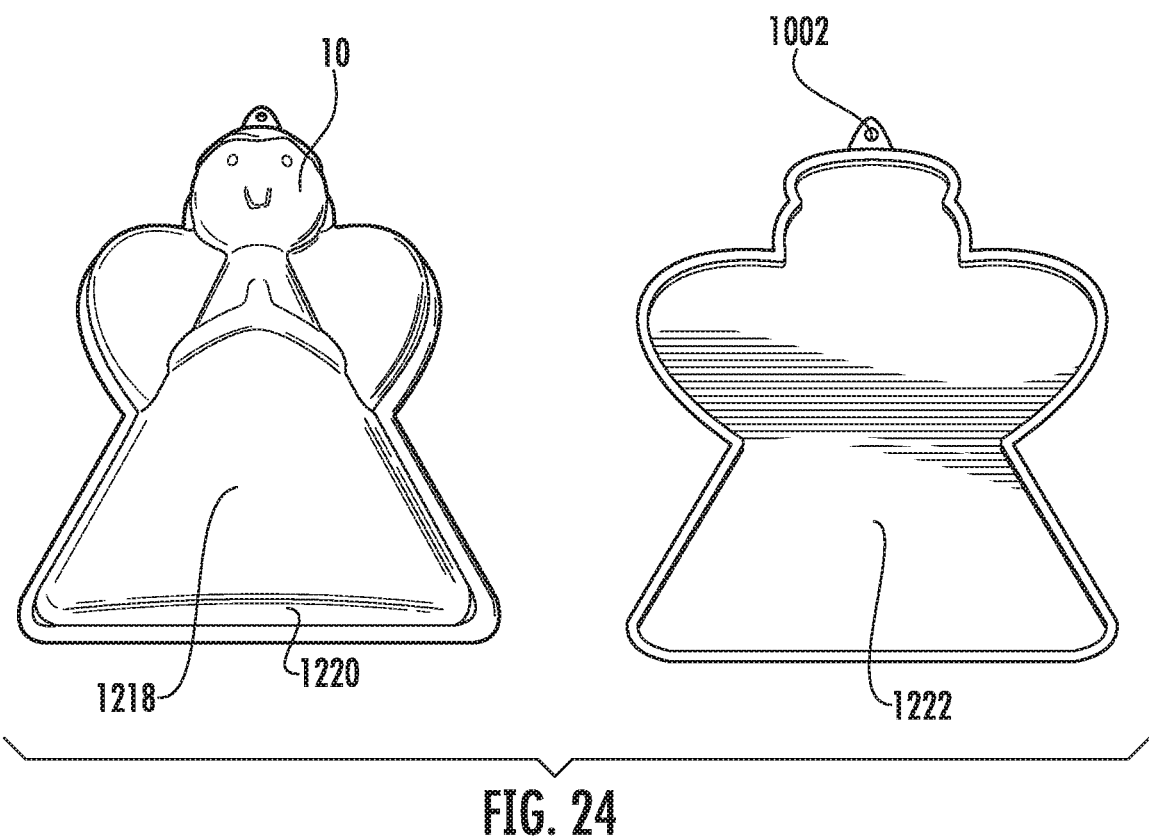
FIG. 24 is a front image of an article and an attachable backing layer, according to certain embodiments of the present invention.
Figure 25:
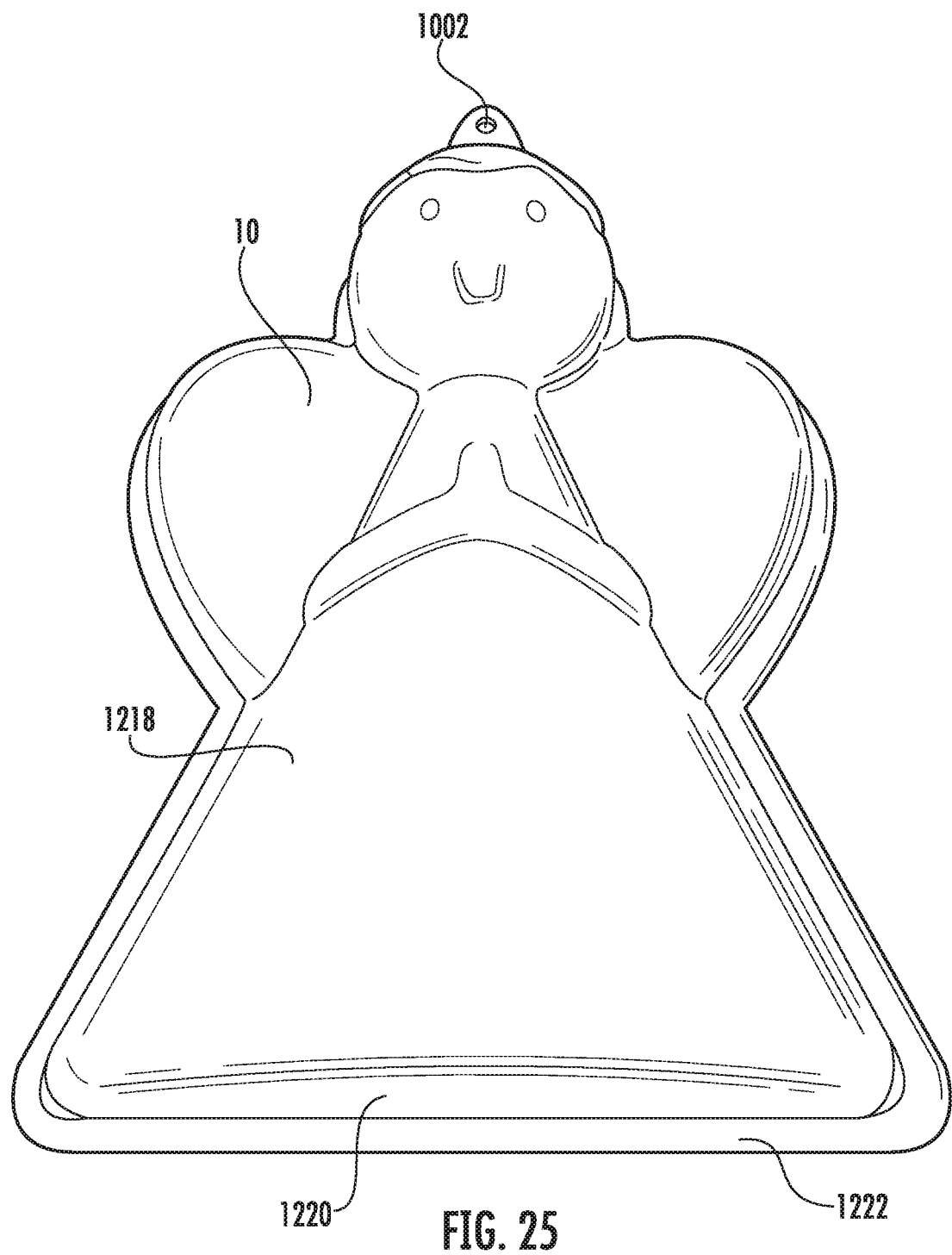
FIG. 25 is a front view of the article of FIG. 24 attached to the backing layer.
Figure 26:
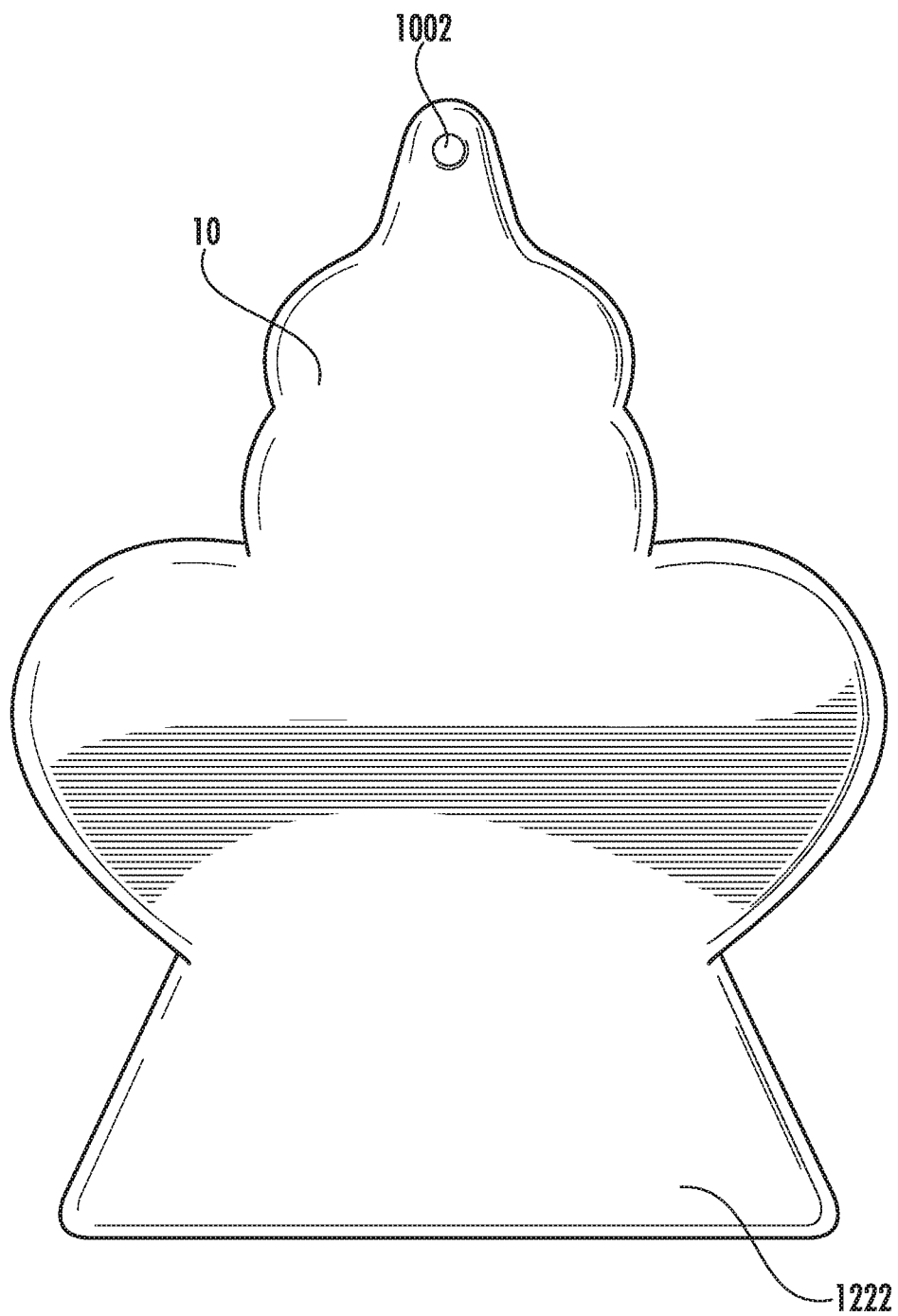
FIG. 26 is a rear view of the article of FIG. 24 attached to the backing layer.
Figure 27:
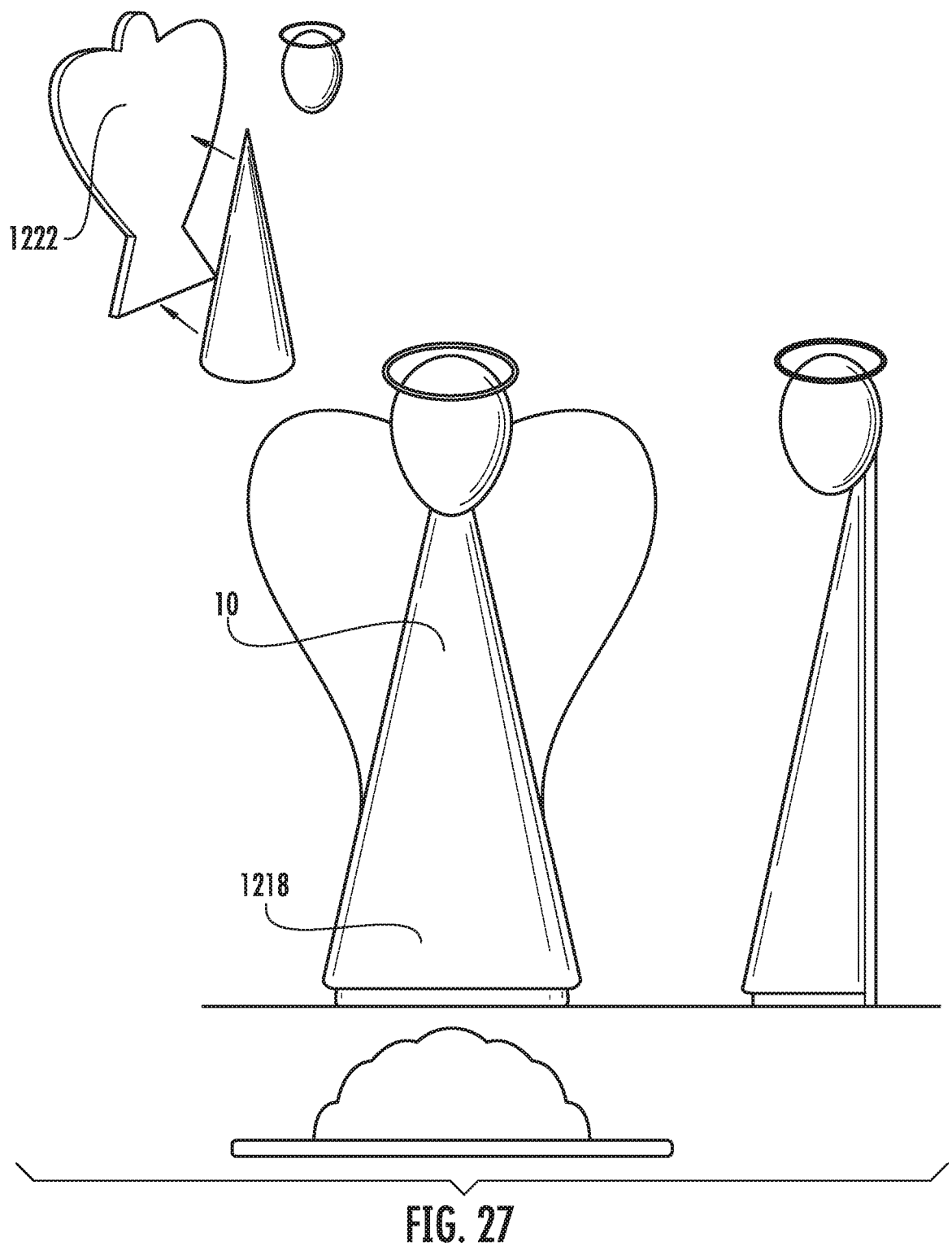
FIG. 27 is a sketch of an article with an attachable backing layer.
Figure 28:
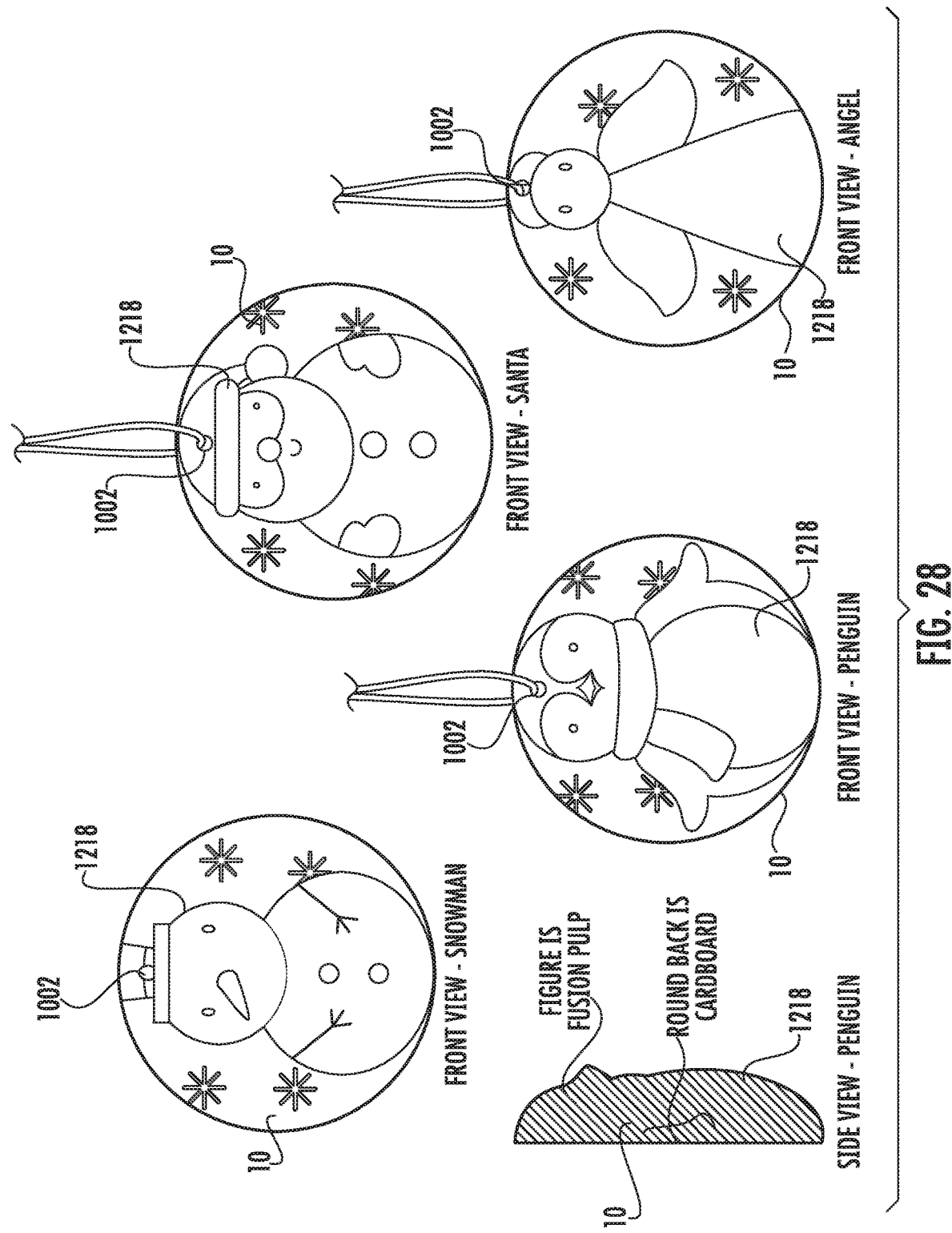
FIG. 28 includes front and side images of articles with attachment elements and a variety of shapes and coloration, according to certain embodiments of the present invention.
Figure 29:
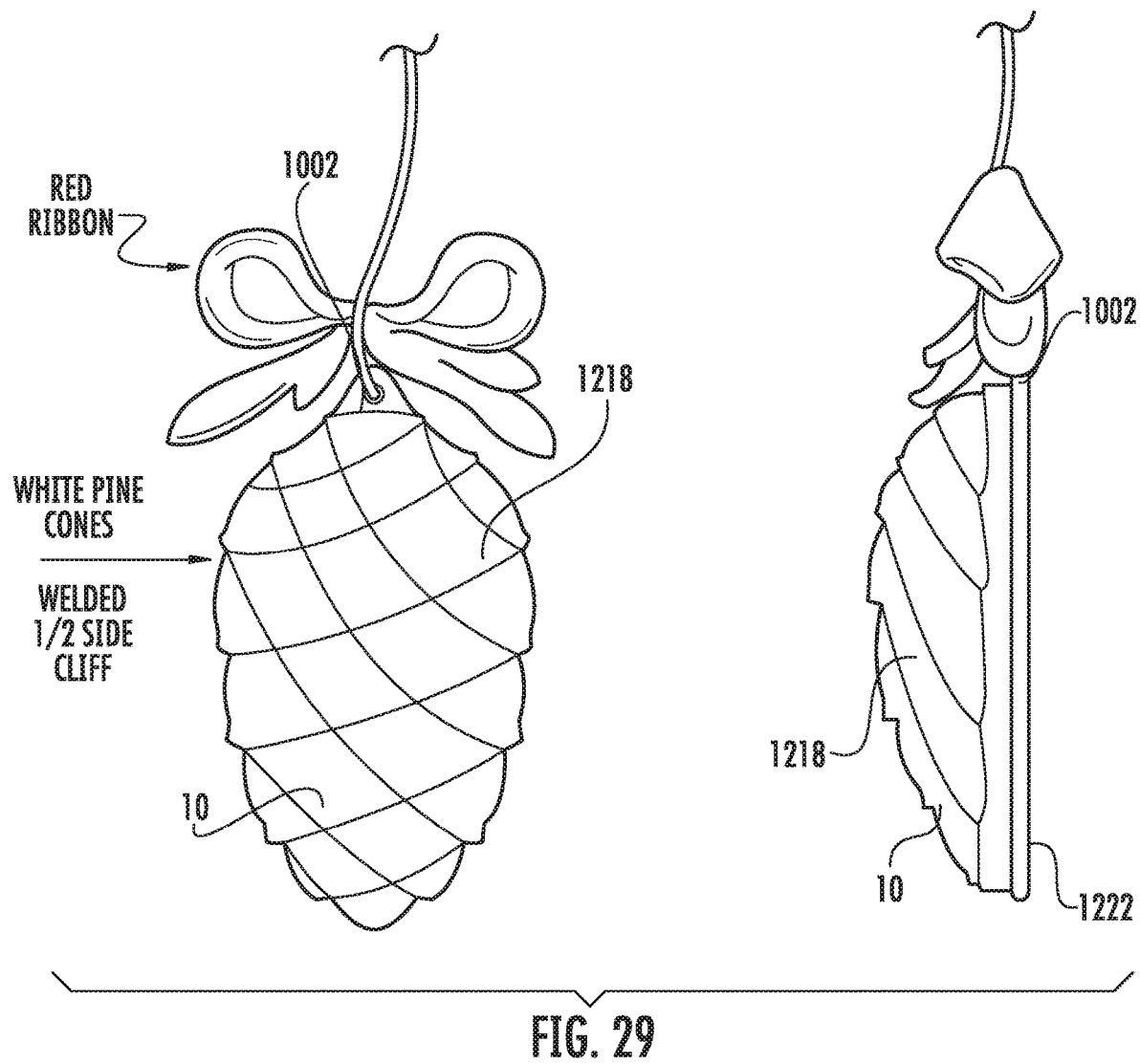
FIG. 29 is a sketch of an article with an attached backing layer.
Figure 30A:
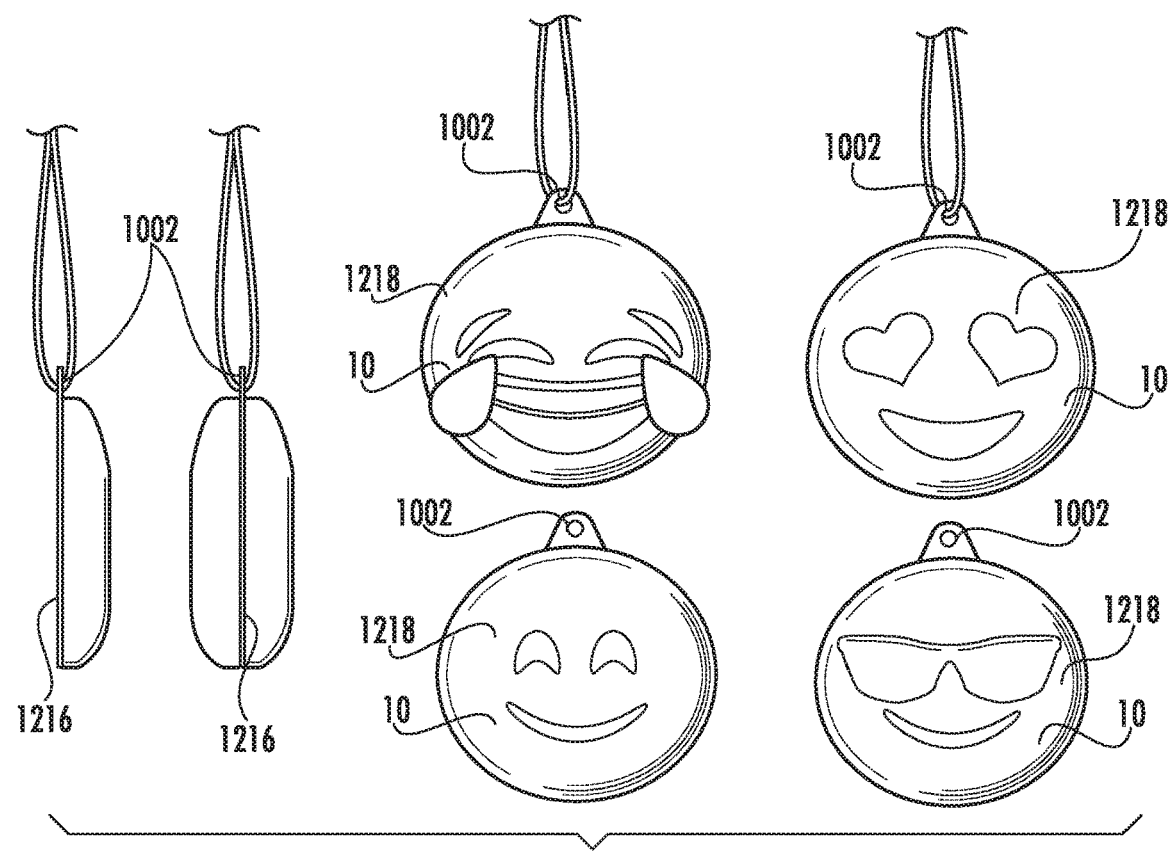
FIG. 30A includes front and side images of articles with attachment elements and a variety of shapes and coloration, along with a side image of an article formed by joining two pulp base materials, according to certain embodiments of the present invention.
Figure 30B:
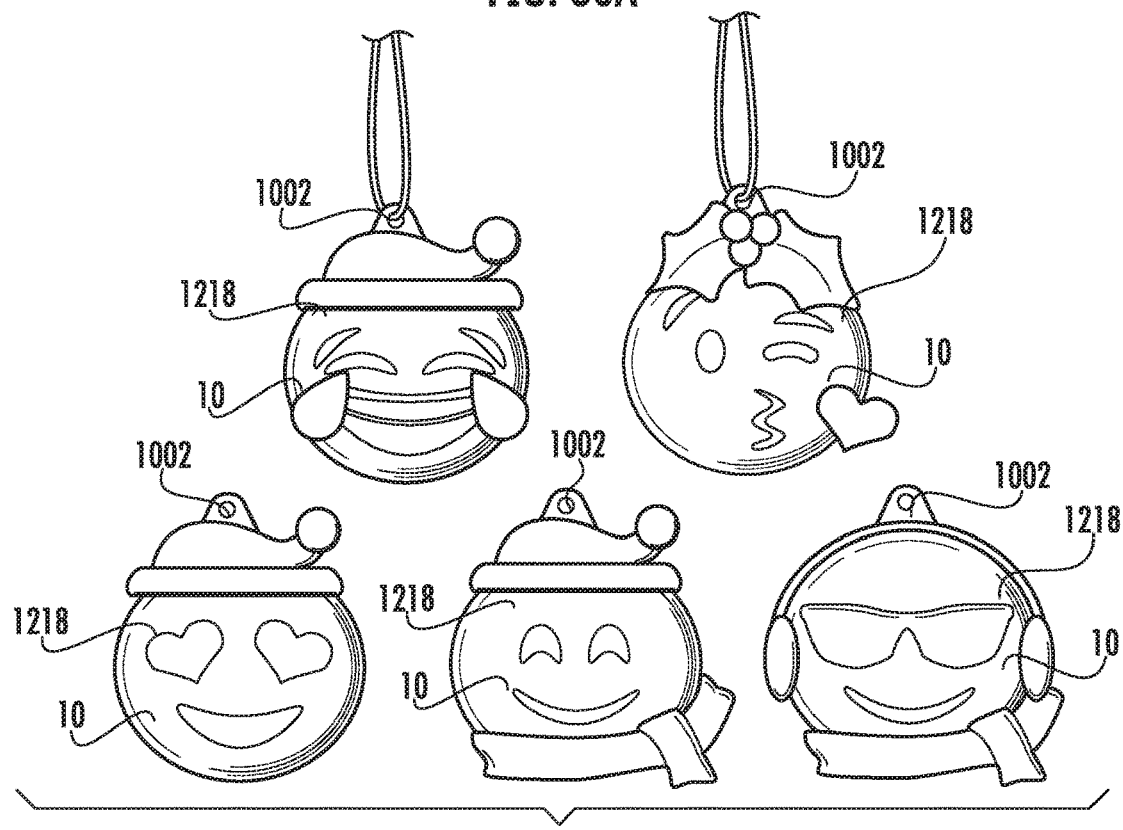
FIG. 30B includes front images of articles with attachment elements and a variety of shapes and coloration, according to certain embodiments of the present invention.
Figure 32:
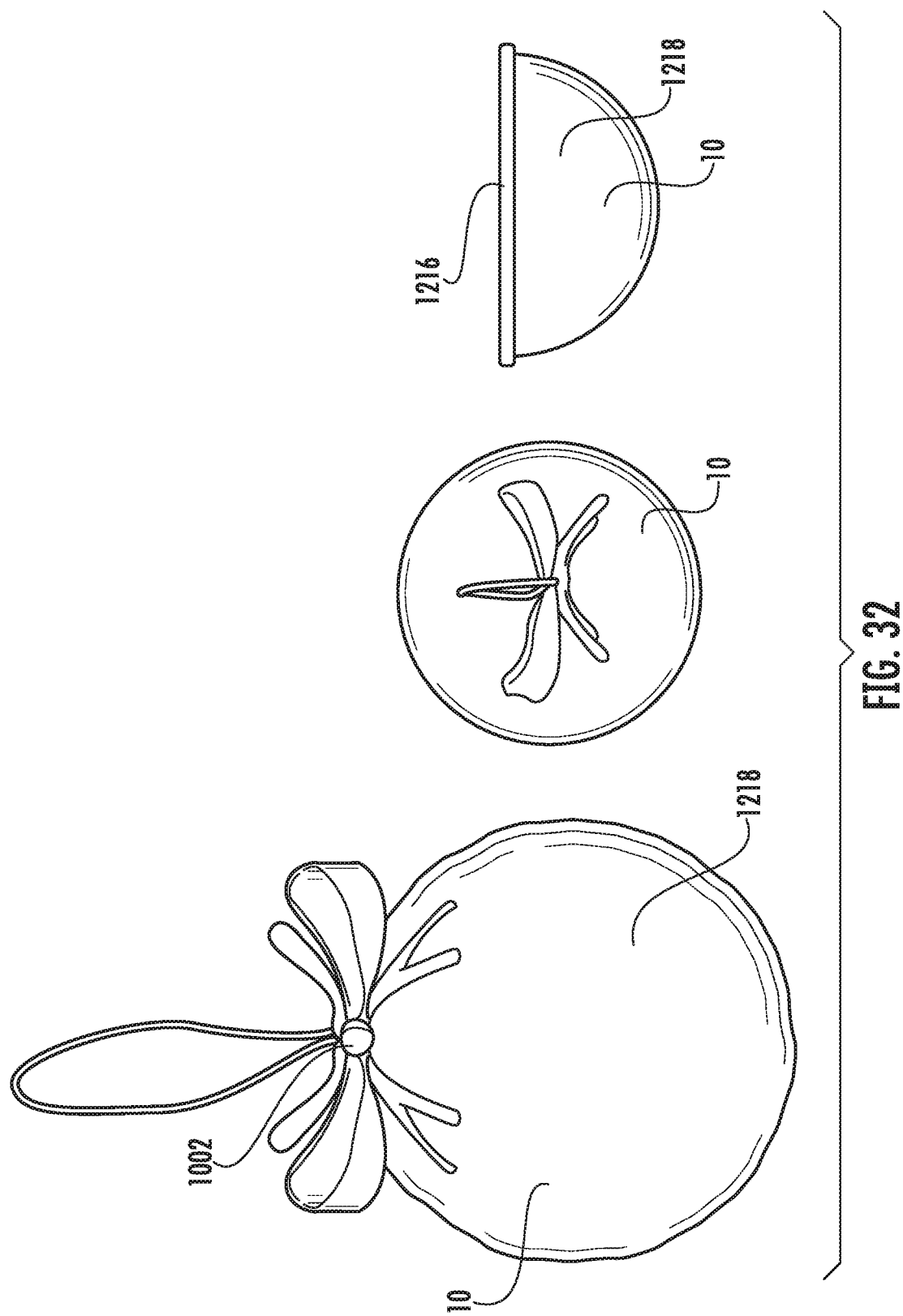
FIG. 32 includes top, front, and side views of an article formed by joining two pulp base materials, according to certain embodiments of the present invention.
Figure 33A:
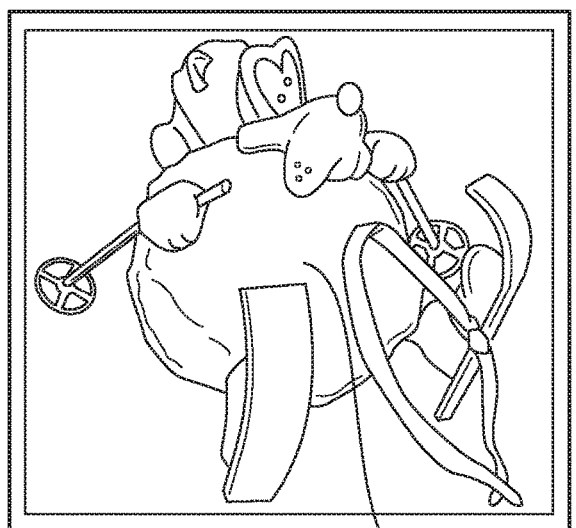
FIGS. 33A, 33B and 33C include images of an article formed by joining two pulp base materials, according to certain embodiments of the present invention.
Figure 33B:
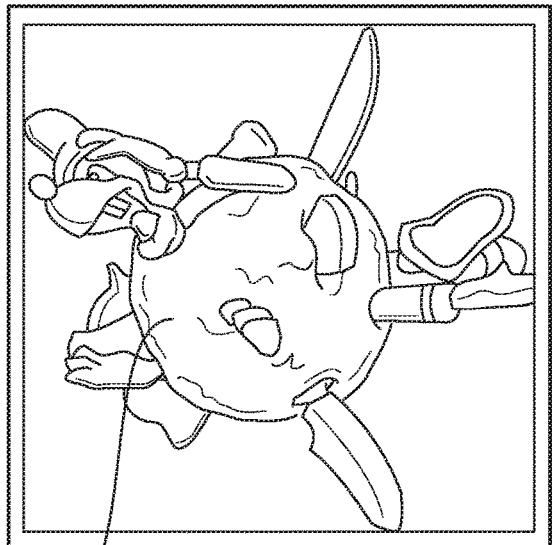
Figure 33C:
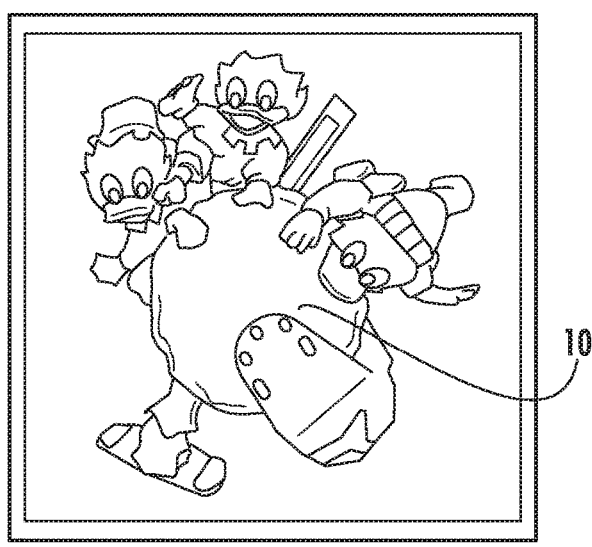
Figure 34:
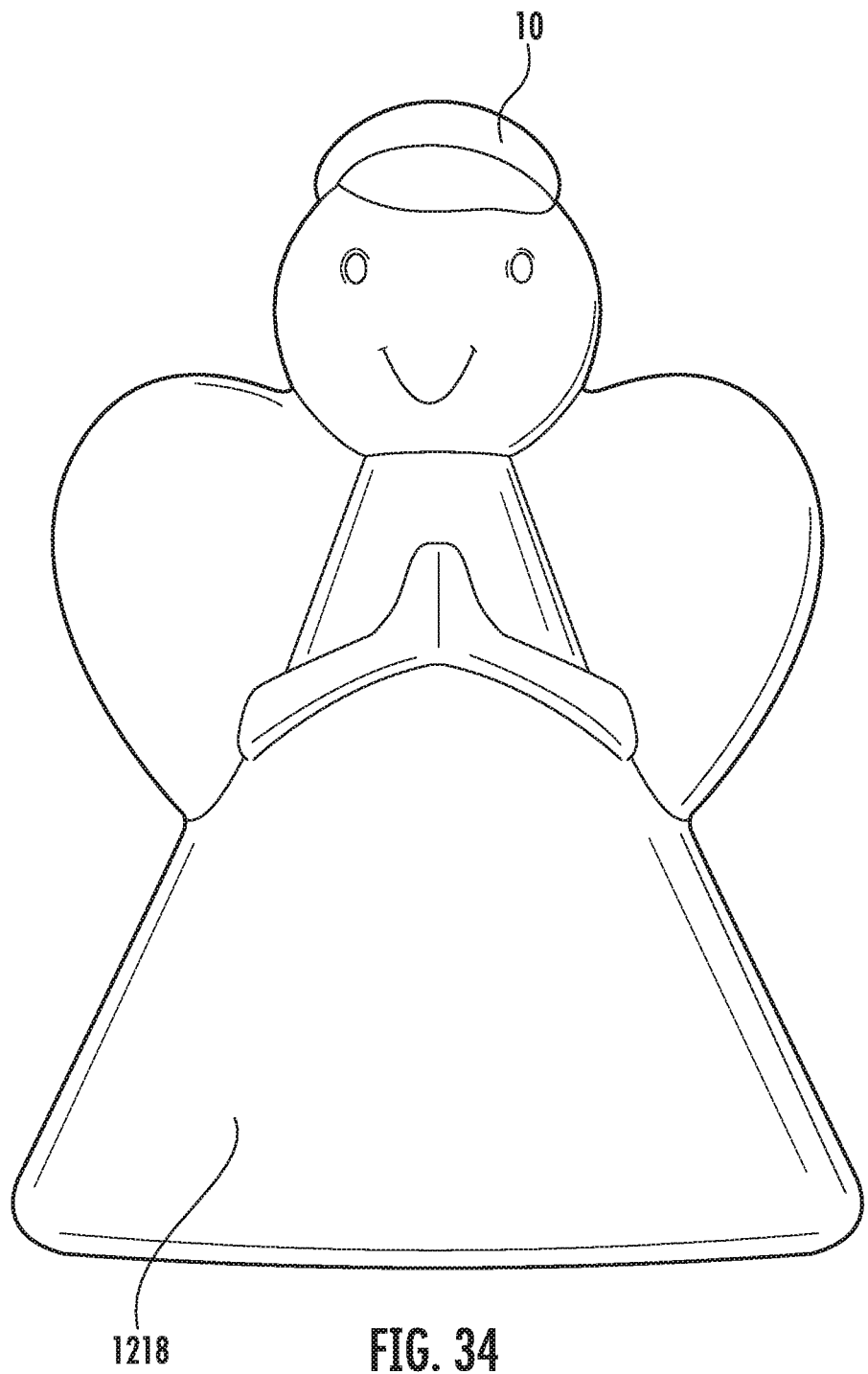
FIG. 34 is a front view of an article, according to certain embodiments of the present invention.
Figure 35:
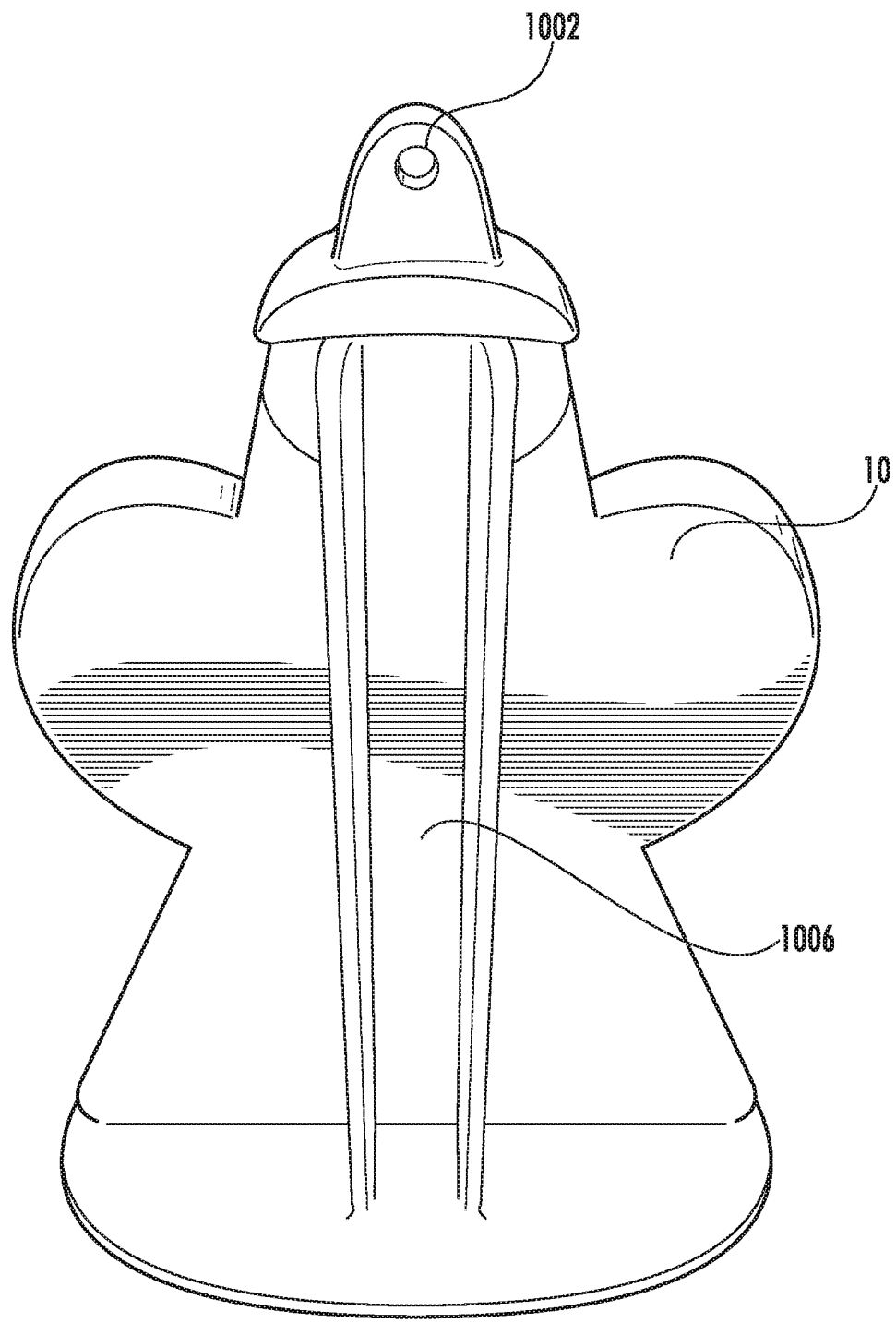
FIG. 35 is a rear view of the article of FIG. 34 coupled to a stand.
Figure 36:
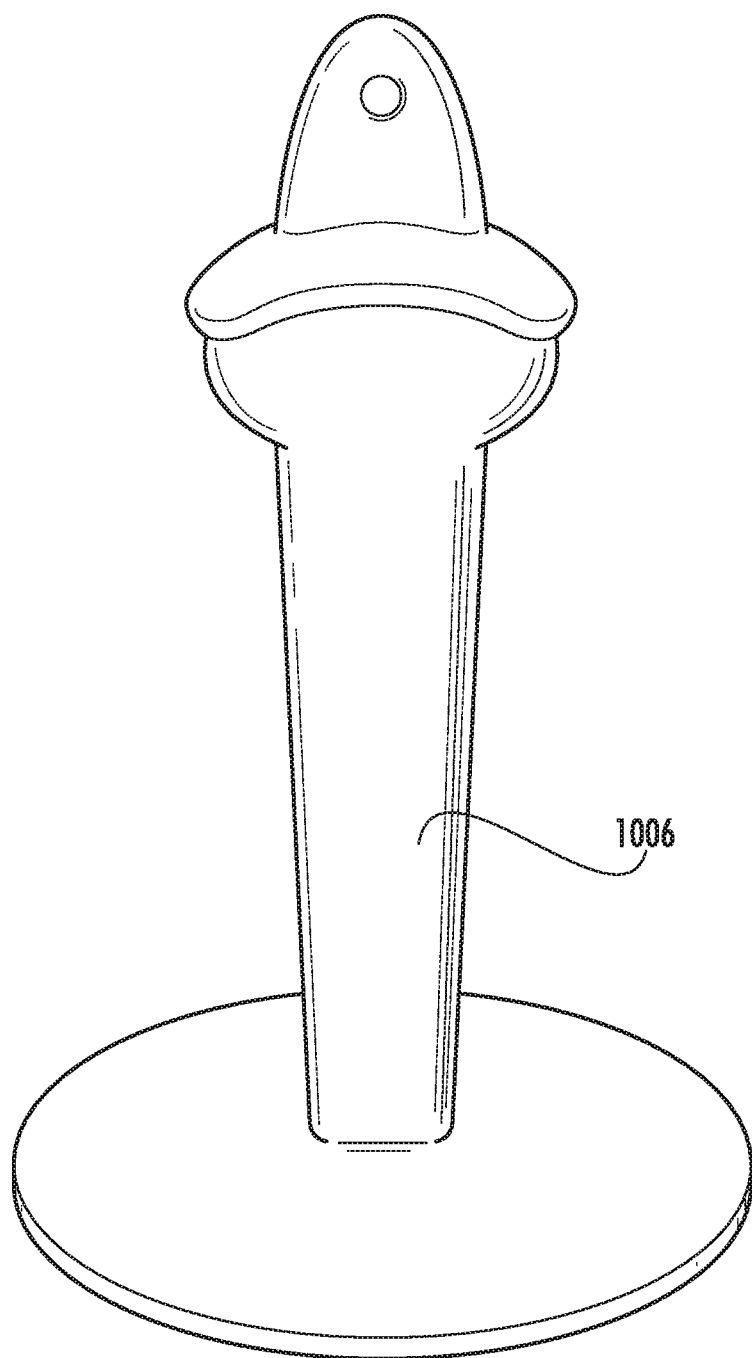
FIG. 36 is a front view of the stand of FIG. 35.
Figure 37:
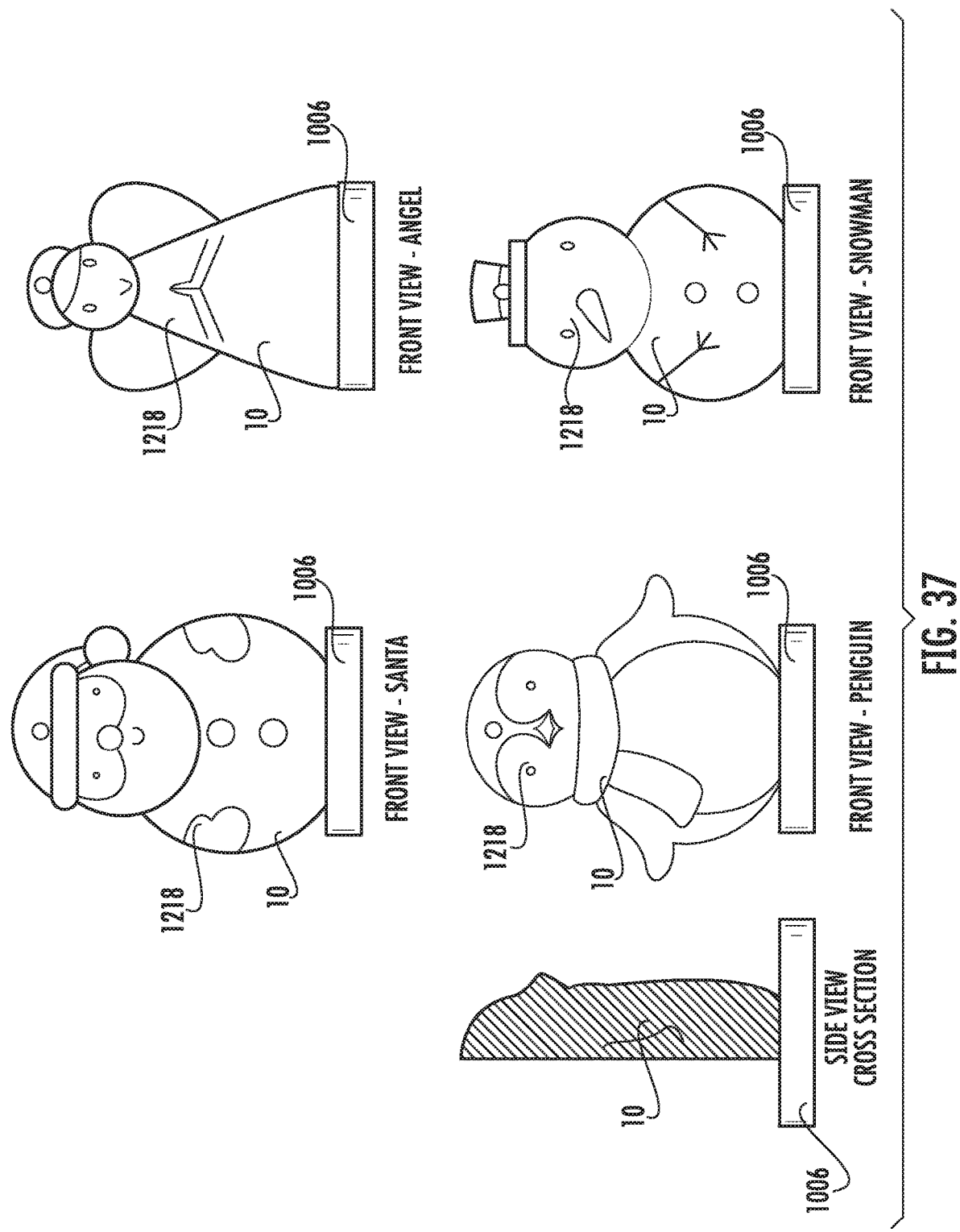
FIG. 37 includes front and side images of articles with stands and a variety of shapes and coloration, according to certain embodiments of the present invention.
Figure 39A:
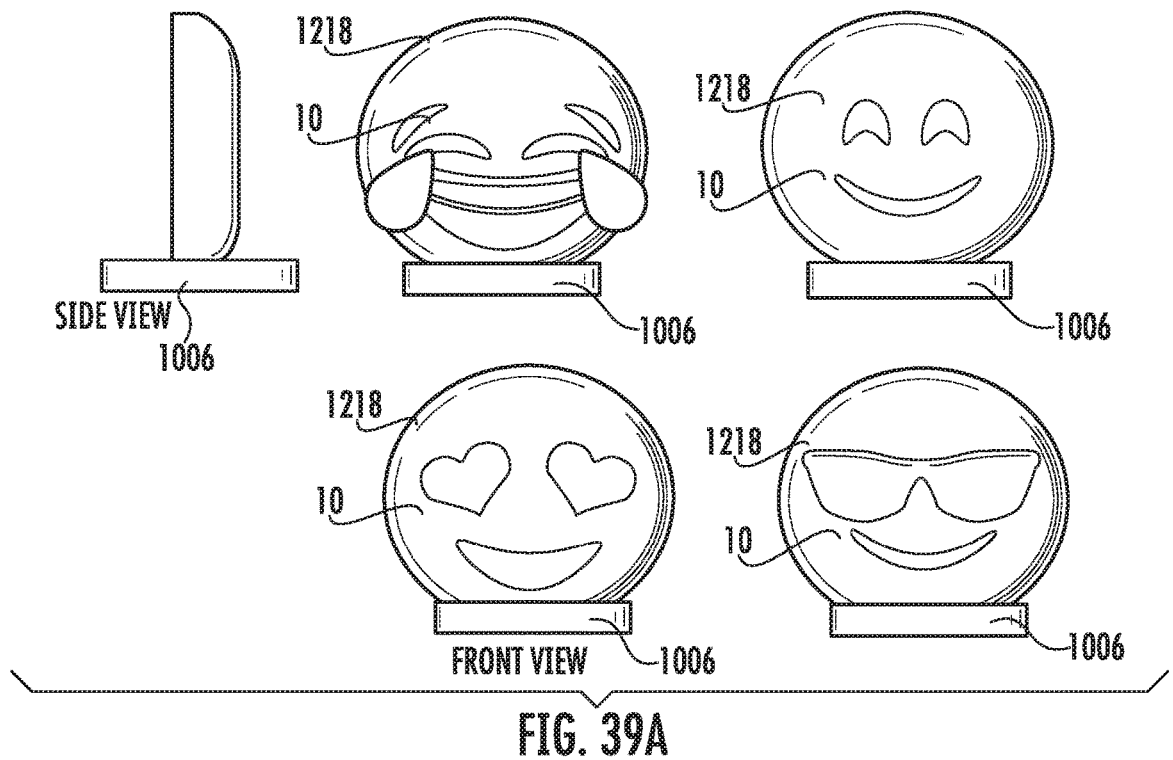
FIG. 39A includes front and side images of articles with stands and a variety of shapes and coloration, according to certain embodiments of the present invention.
Figure 39B:
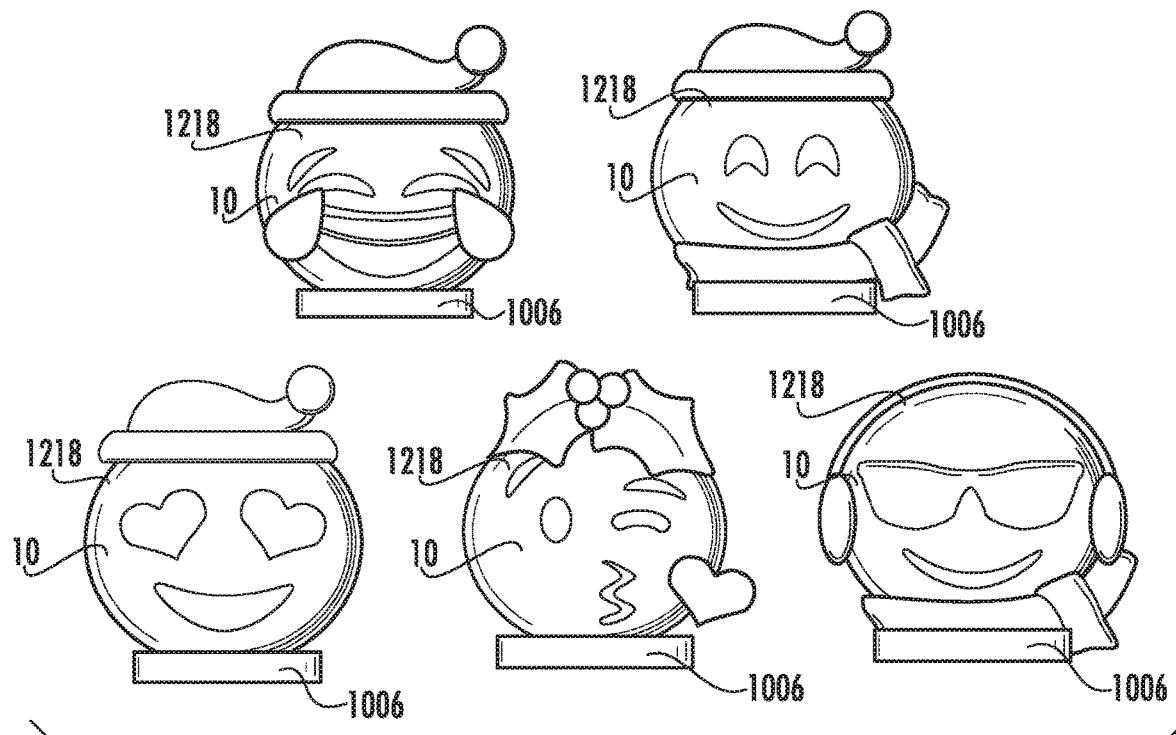
FIG. 39B includes front images of articles with stands and a variety of shapes and coloration, according to certain embodiments of the present invention.
Figure 40:
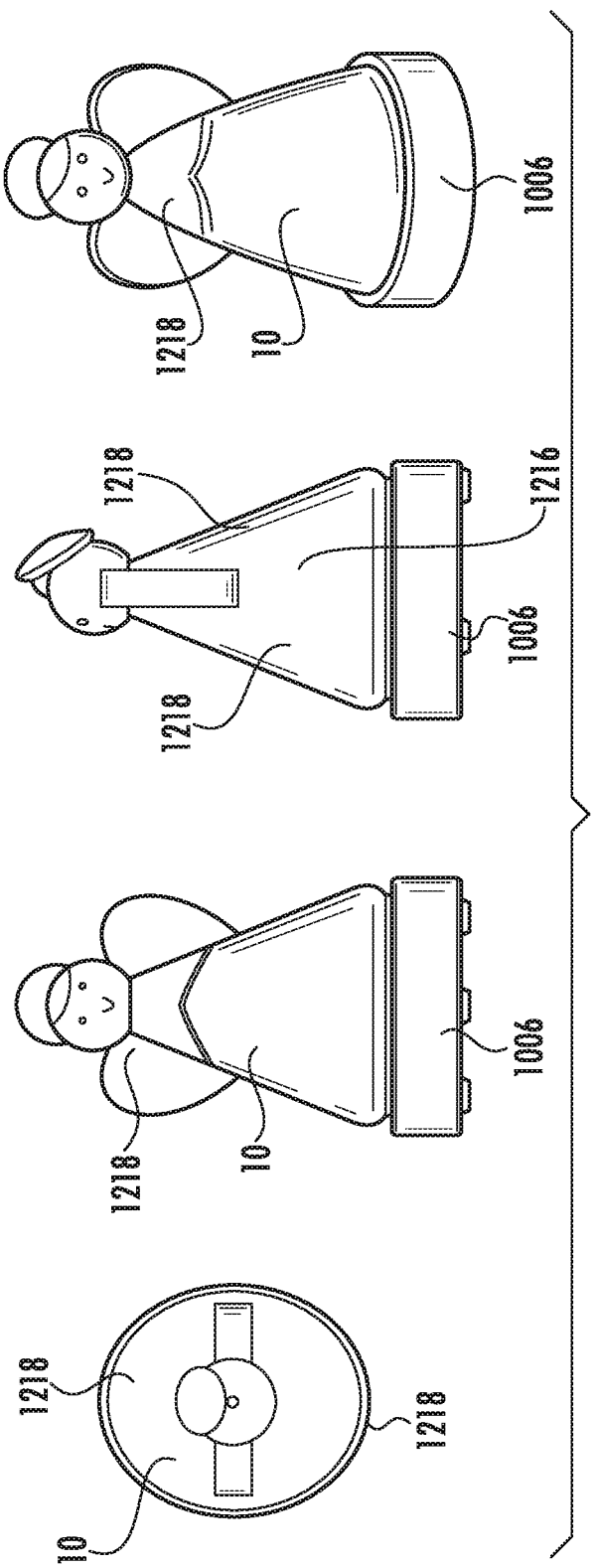
FIG. 40 includes top, front, side, and rear views of an article formed by joining two pulp base materials, according to certain embodiments of the present invention.
Figure 41A:
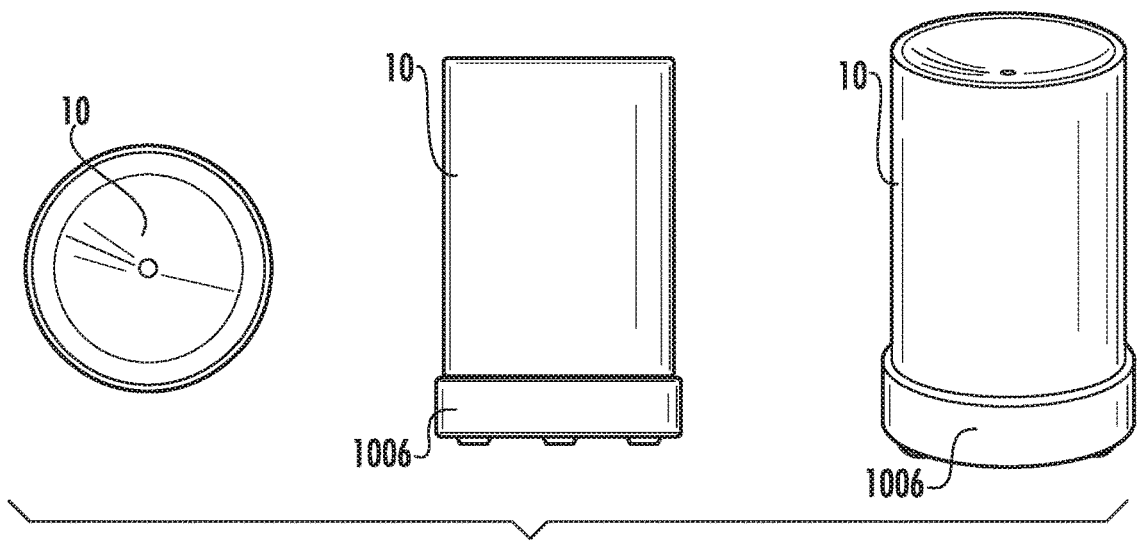
FIGS. 41A, 41B, and 41C include top and side views of articles with stands and a variety of shapes, according to certain embodiments of the present invention.
Figure 41B:
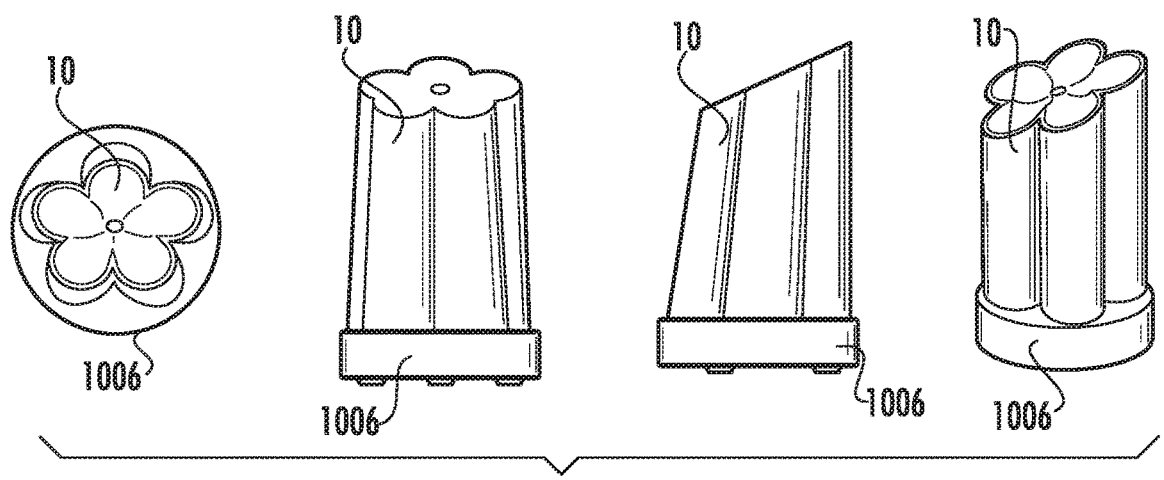
Figure 41C:
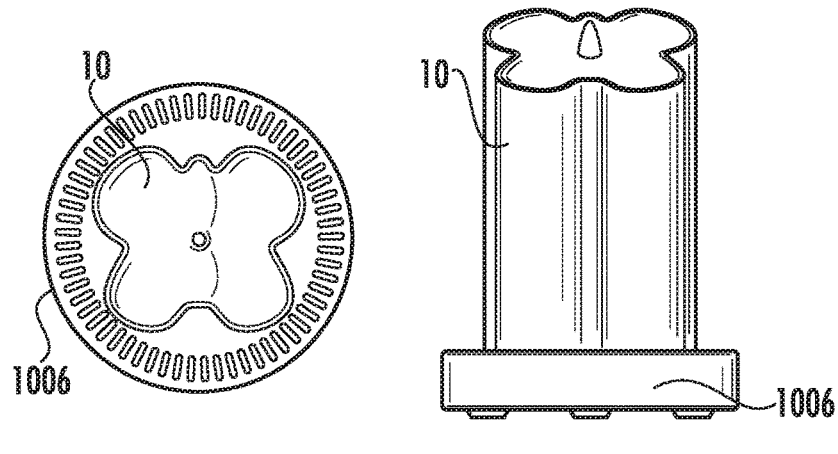
Figure 42:
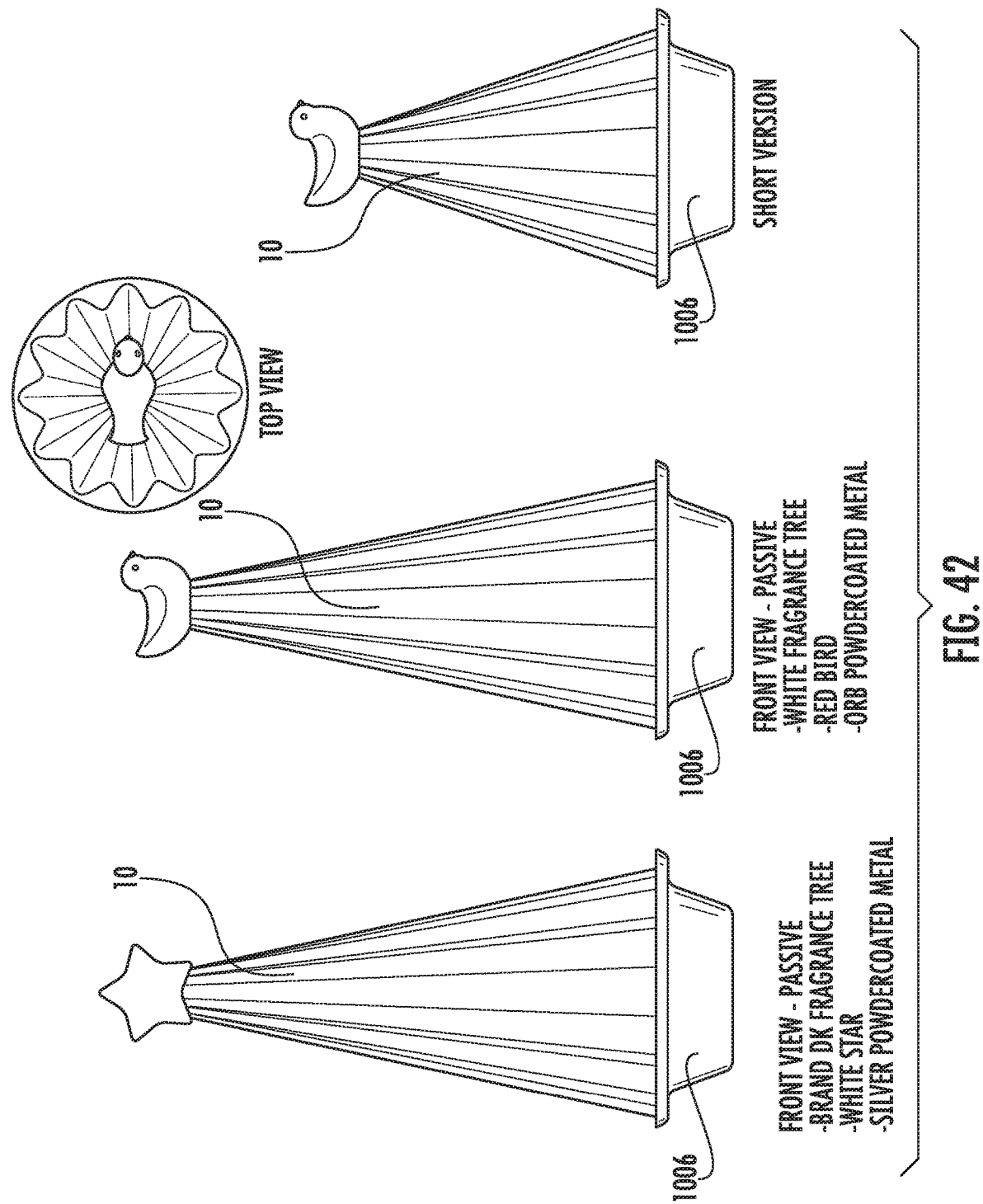
FIG. 42 includes side views of articles with stands, according to certain embodiments of the present invention.
Figure 43:
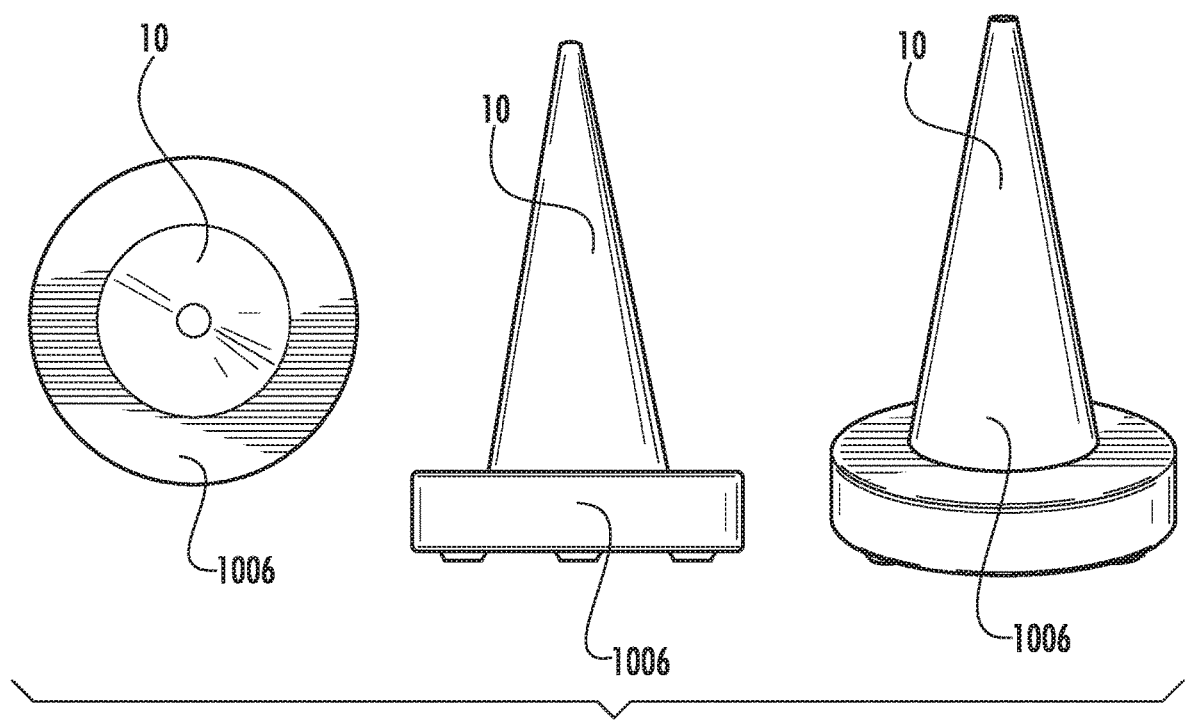
FIG. 43 includes top, side, and perspective views of an article with a stand, according to certain embodiments of the present invention.
Figure 44A:
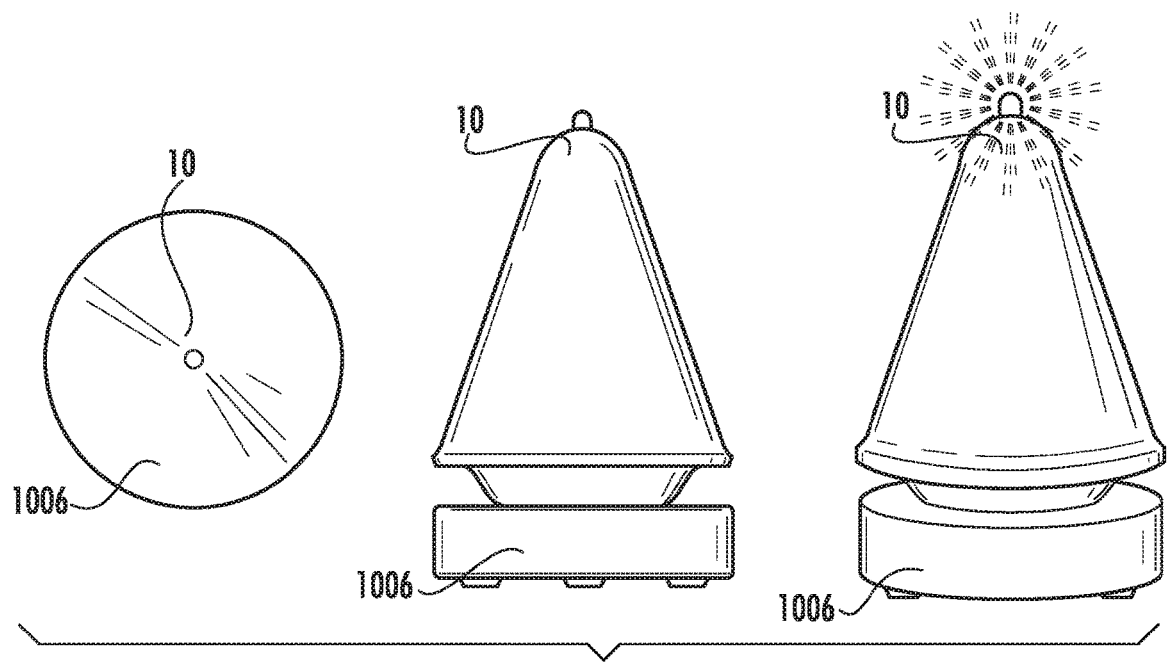
FIGS. 44A and 44B include top, side, and perspective views of an article with a stand, according to certain embodiments of the present invention.
Figure 44B:
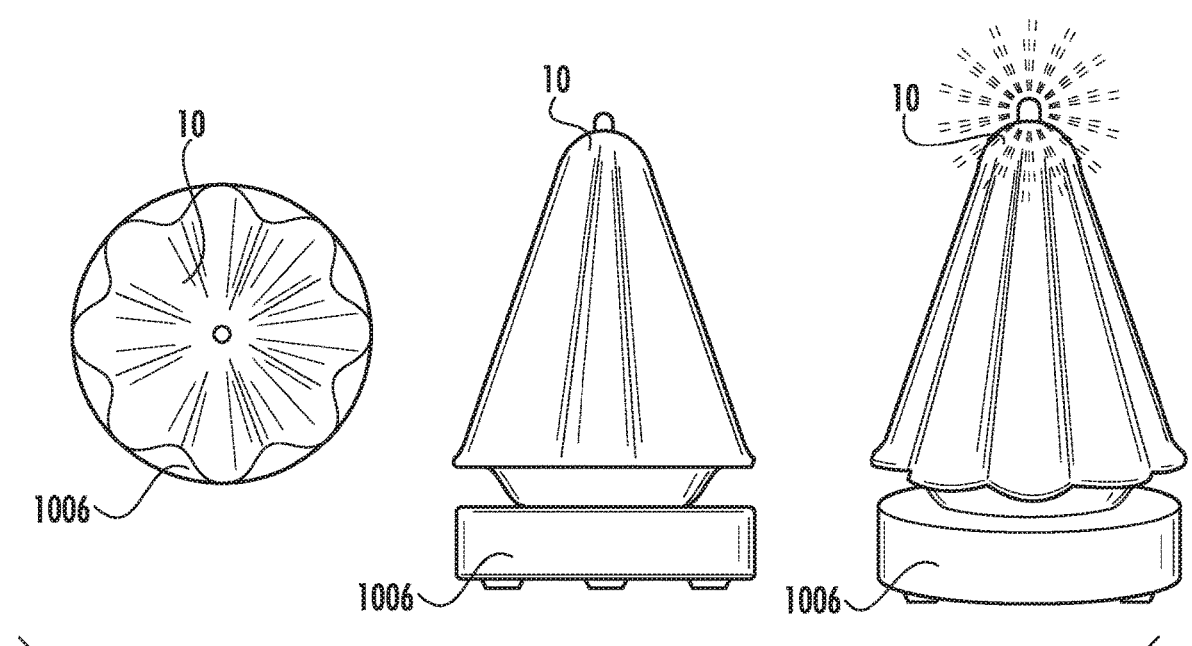
Figure 45:
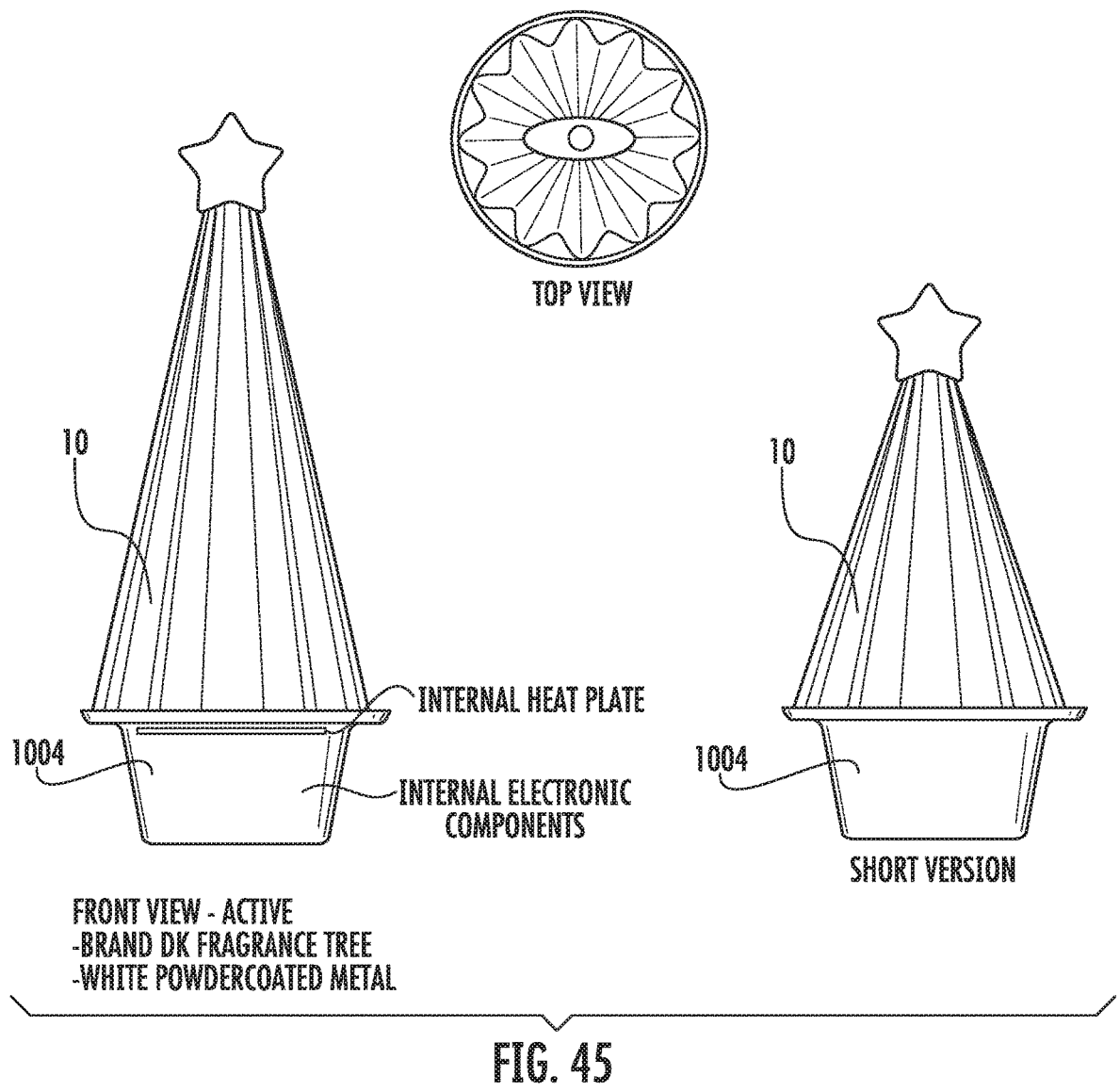
FIG. 45 includes side views of articles combined with energy sources, according to certain embodiments of the present invention.
Figure 47:
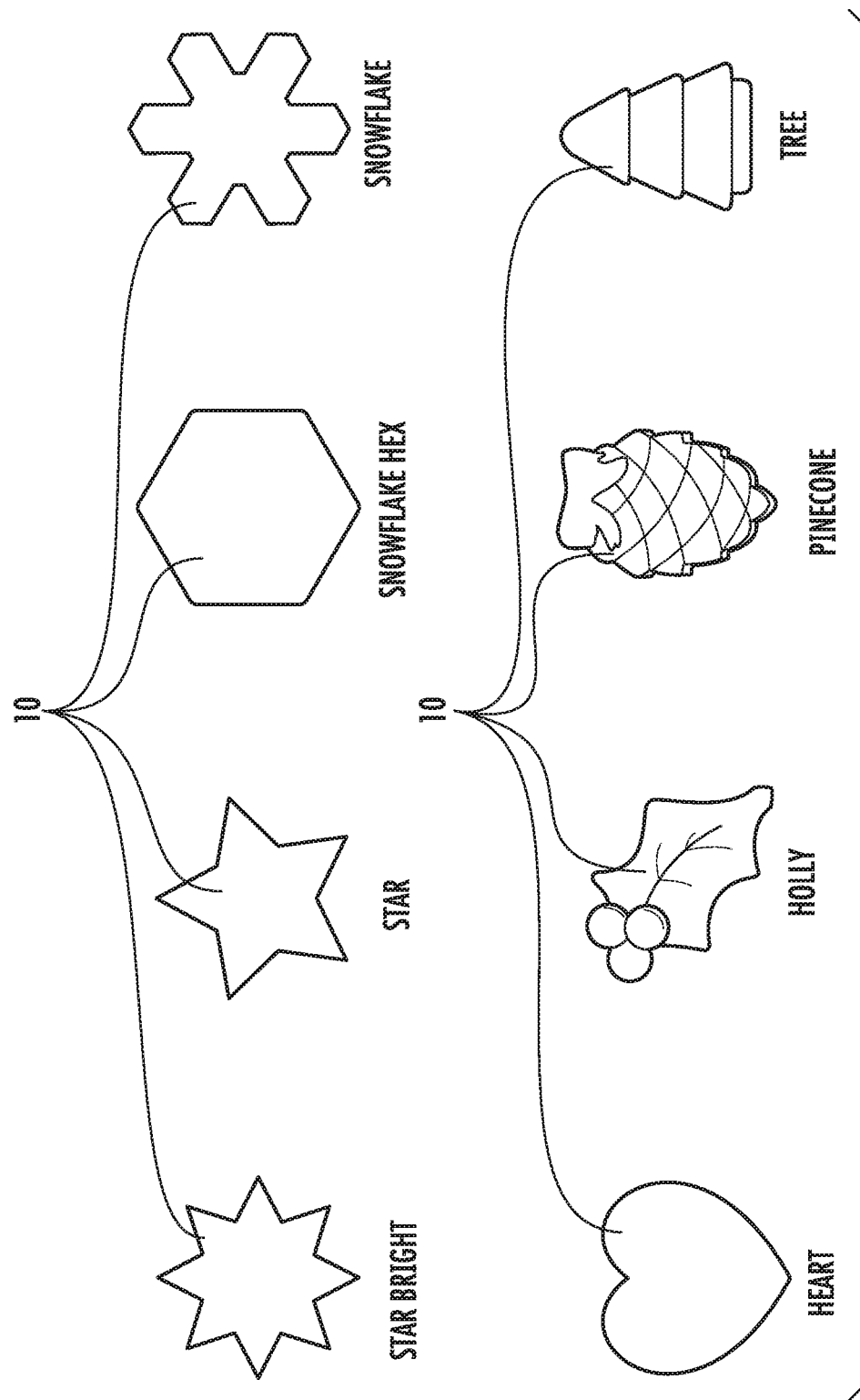
FIG. 47 includes front views of articles with a variety of shapes and coloration, according to certain embodiments of the present invention.
Figure 48:
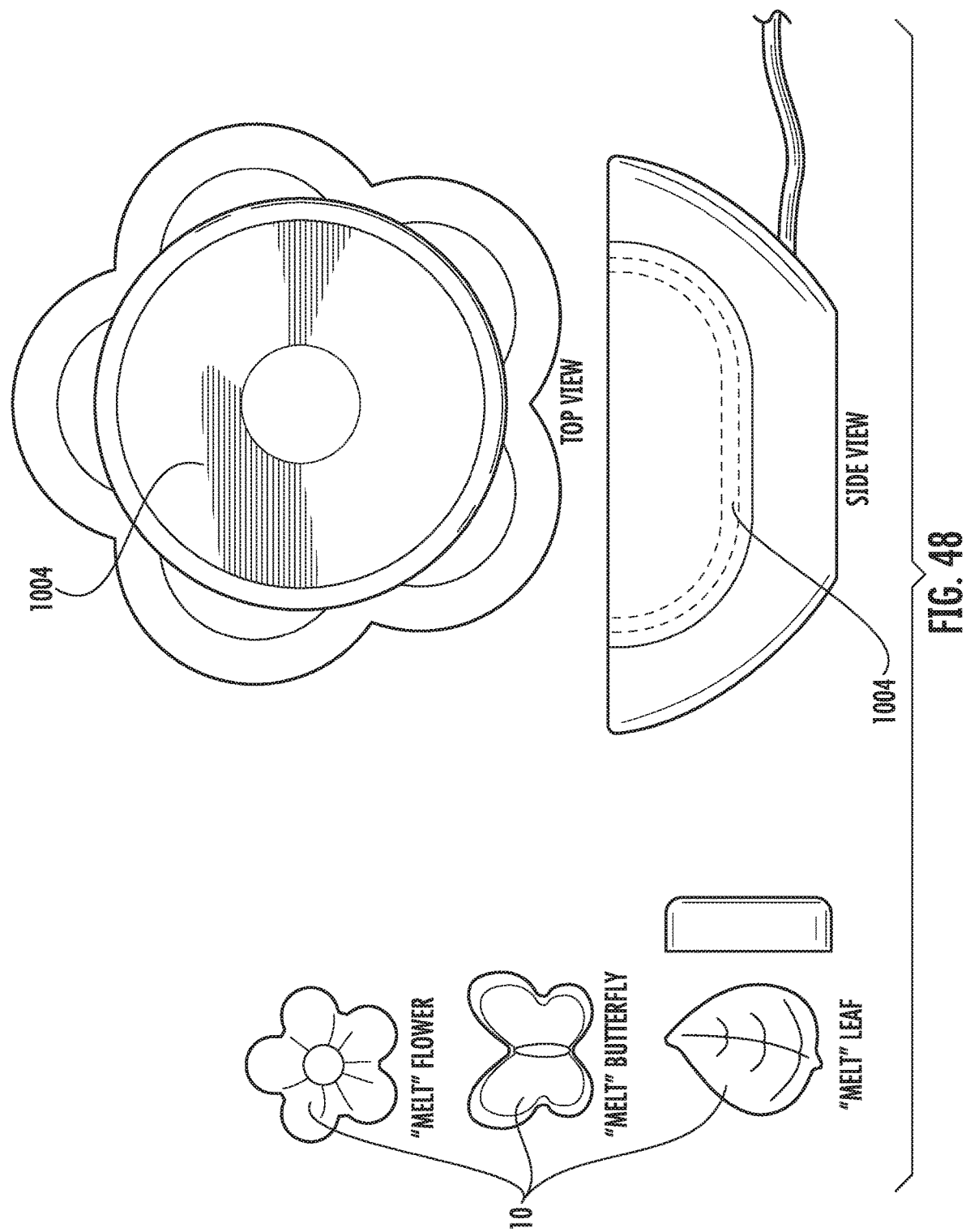
FIG. 48 includes front views of articles with a variety of shapes and a warmer bowl, according to certain embodiments of the present invention.
Figure 49:
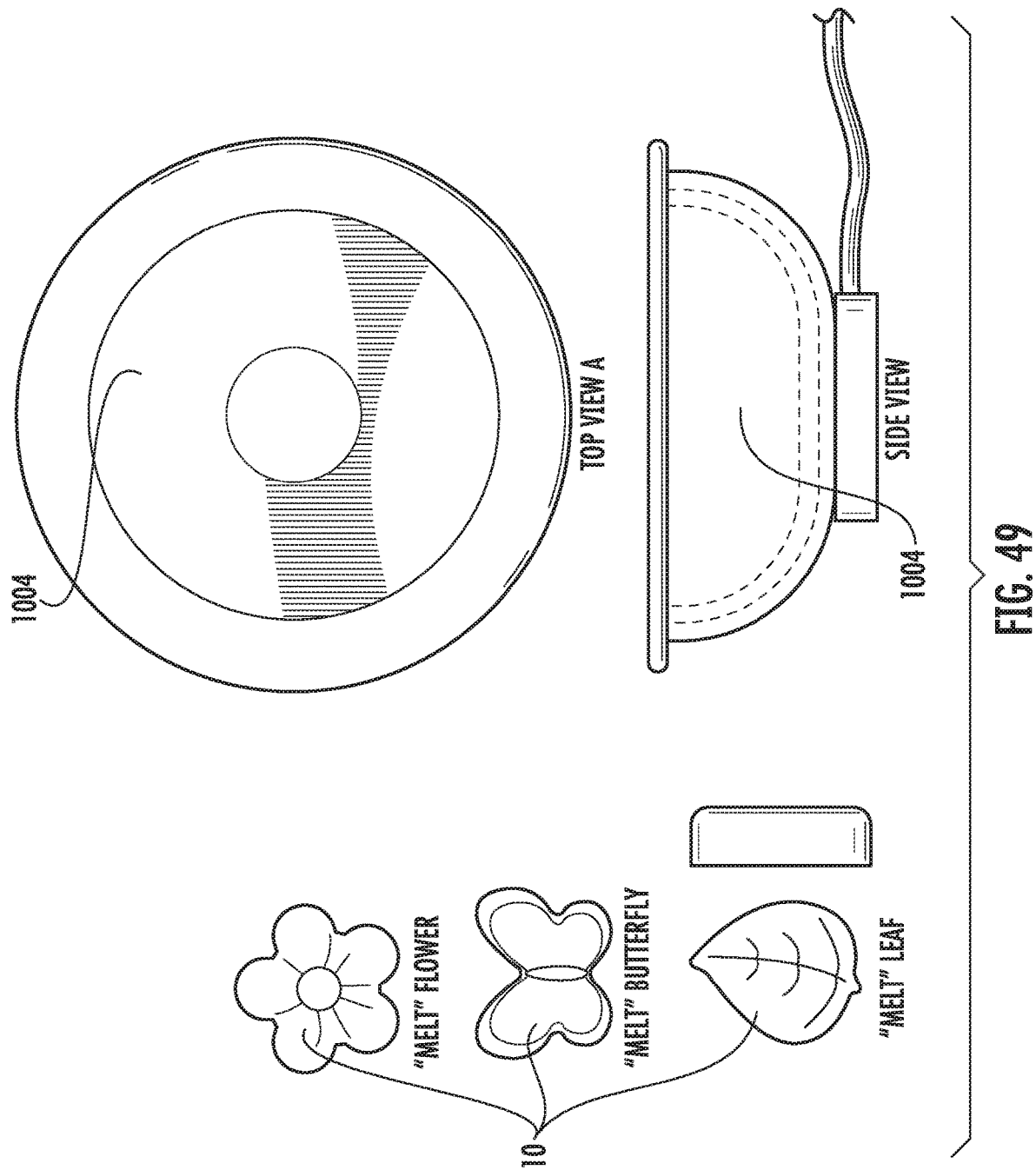
FIG. 49 includes front views of articles with a variety of shapes and a warmer bowl, according to certain embodiments of the present invention.

In other embodiments, as best illustrated in FIG. 19, a capillary structure 1230 may be incorporated into the dividers 1212 and/or may be a separate structure that is added to the mold 1204 prior to or during the pulp composition addition. This capillary structure 1230 may comprise a length of tubing 1232 having one open end 1234 accessible from an outer surface of the pulp base material 12 and an opposing end 1236 terminating within the body of the pulp base material 12. The opposing end 1236 may be connected to the divider 1212 to suspend the capillary structure 1230 within the mold 1204 during the pulp composition addition and molding process.

In certain embodiments, the capillary structure 1230 may comprise separate tubing extending through each zone 1206, 1208. The tubing may further comprise a series of small apertures 1238 along its length. The capillary structure 1230 may be used to reintroduce a volatile composition 24 into the zones 1206, 1208 once the concentration is depleted. The volatile composition 24 is introduced through the open end 1234 and disperses into the zones 1206, 1208 via the apertures 1238. Each zone 1206, 1208 may receive a different volatile composition 24 and/or the re-fill design allows for the volatile compositions 24 to be replaced with different scents as desired.

In certain embodiments, as best illustrated in FIGS. 45-46, 48-49, and 51-58, the article 10 may be combined with at least one energy source 1004, including but not limited to a heating element (such as a warmer bowl or plate, electrical plug-in, chemical warmer pack, candle, light source, heating element system, and any other heat generating object) and a wind element (such as a fan, blower, air circulation vent, bladeless fan, and any other air movement object).

The article 10 may be combined with the energy source 1004 in a variety of manners. A variety of energy sources that are attached and/or placed in close proximity to articles containing volatile compositions are described in U.S. Publication No. 2015/0217016, the entire contents of which is incorporated herein by reference.

In some embodiments, the article 10 may be positioned within a warmer bowl or plate 1004, wherein the article 10 is heated through contact with the surface of the warmer bowl 1004. The surface of the warmer bowl or plate 1004 produces heat in a range of approximately 90° F. to 250° F. In further embodiments, a chemical warmer pack 1004 may be attached or positioned adjacent to the article 10.

In these embodiments, the backing layer 1222 may be configured to serve as a contact surface between the article 10 and the warmer bowl 1004. To improve the efficiency of heat transfer between the article 10 and the warmer bowl 1004, the backing layer 1222 may be formed of a conductive material such as tin, copper, aluminum, or other suitable metallic materials.

According to some embodiments, the article 10 may be shaped into a light shade or screen, which is positioned around and/or near an incandescent light bulb. For example, the article 10 may be positioned as a screen for a night light or a shade for small decorative lights. The article 10 may also be configured as a lamp shade or screen for larger bulbs.

Figure 77:
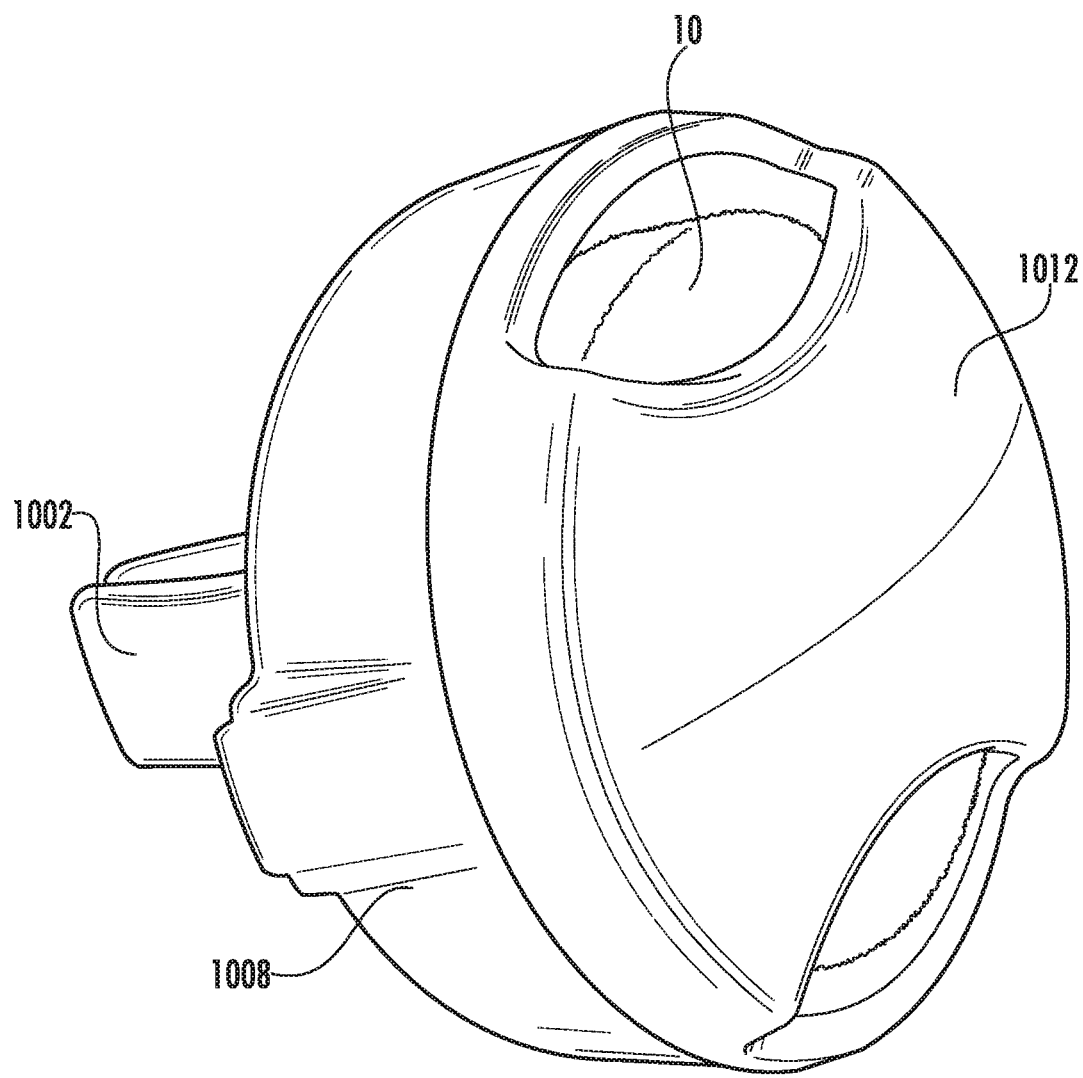
FIG. 77 is a perspective assembled view of a support structure for an article, according to certain embodiments of the present invention.
Figure 78A:
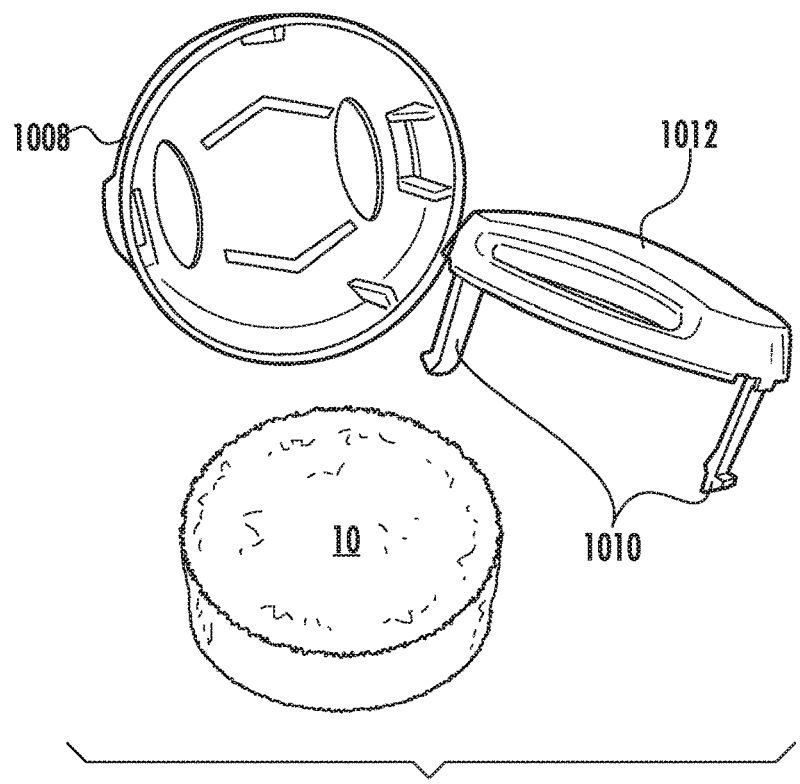
FIGS. 78A and 78B are exploded perspective views of the support structure of FIG. 77.
Figure 78B:
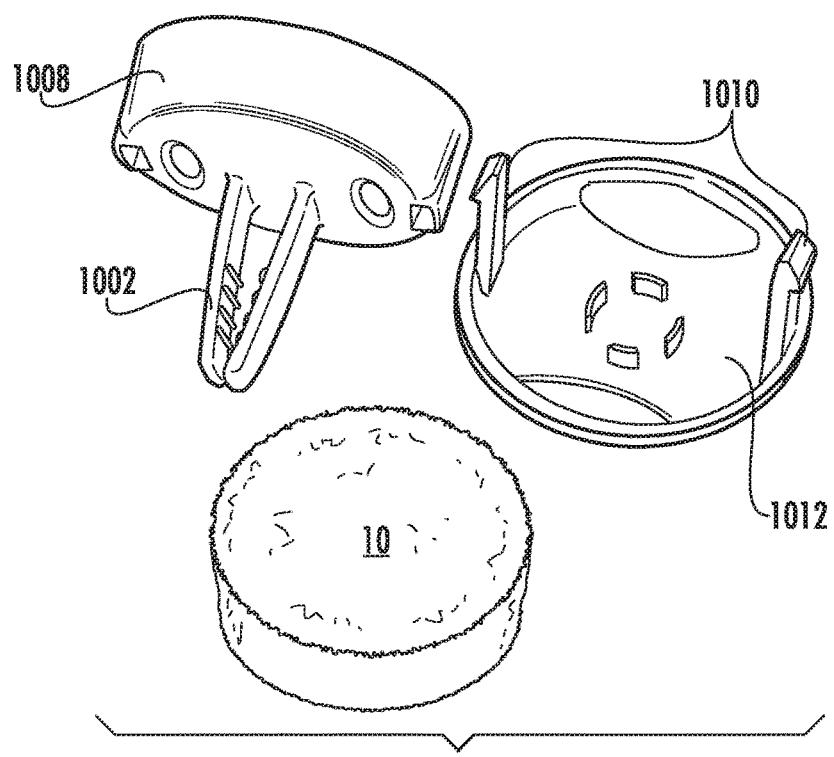

The article 10 may also be positioned within the path of and/or coupled to a wind element such as a fan, as shown in FIGS. 57-58 and 77-78B. In some embodiments, the article 10 may form at least a portion of one or more blades of the fan and/or may be attached to a vent cover. In these embodiments, the article 10 may be positioned within a support structure 1008, such as the pronged structure 1008 shown in FIGS. 59-64 or the cup structure 1008 in FIGS. 77-78B. Prongs 1010 extend to partially enclose sides of the article 10 to secure the article 10 to the support structure 1008. The prongs 1010 may be attached to the support structure 1008 (as shown in FIGS. 59-64) or to the decorative cover 1012 (as shown in FIGS. 77-78B). The support structure 1008 also comprises an attachment element 1002, which secures the support structure 1008 to a vent blade or other suitable surface. In some embodiments, as shown in FIG. 78B, the attachment element 1002 may include a pair of clamp members biased toward one another that can engage a suitable surface, such as an exterior portion of a fan or a vent in an automobile. The support structure 1008 may further comprise a decorative cover 1012 that attaches to an outer surface of the prongs 1010.

The heat generated by the energy source 1004 heats the volatile composition 24 within the article 10 so as to facilitate its release, and the wind generated by the energy source 1004 creates an air flow over the article 10, which facilitates dispersion of the volatile composition 24.

As shown in FIGS. 73-76, the article 10 may include a plurality of zones with different densities. The article 10 may have any number of zones with different respective densities. For example, the article 10 may include a first density zone 1241, a second density zone 1242, a third density zone 1243, and a fourth density zone 1244. In some embodiments, the density zones may correlate to various porosity zones, as described above (e.g., high porosity zones 1206 and low porosity zones 1208). In some cases, a high density zone correlates to a low porosity zone 1208 and a low density zone correlates to a high porosity zone 1206. However, the article 10 is not limited to two density/porosity zones and may have any number of density/porosity zones. In addition to affecting the absorption and subsequent release of the volatile composition 24 (explained in greater detail below), the various density zones may also affect the aesthetics/appearance of article 10. In some embodiments, the volatile composition 24 may be combined with a dye (such as an oil soluble dye). Various dyes are described in greater detail below. The color of the dye in the volatile composition 24 appears more dark or concentrated in the high density areas of article 10. In some cases, the base material 12 is approximately white and the dye is a color (such as red, blue, green, etc.) such that the lower density areas appear closer to the white color of the base material 12 while the higher density areas have a darker color closer to the color of the dye.

Figure 73:
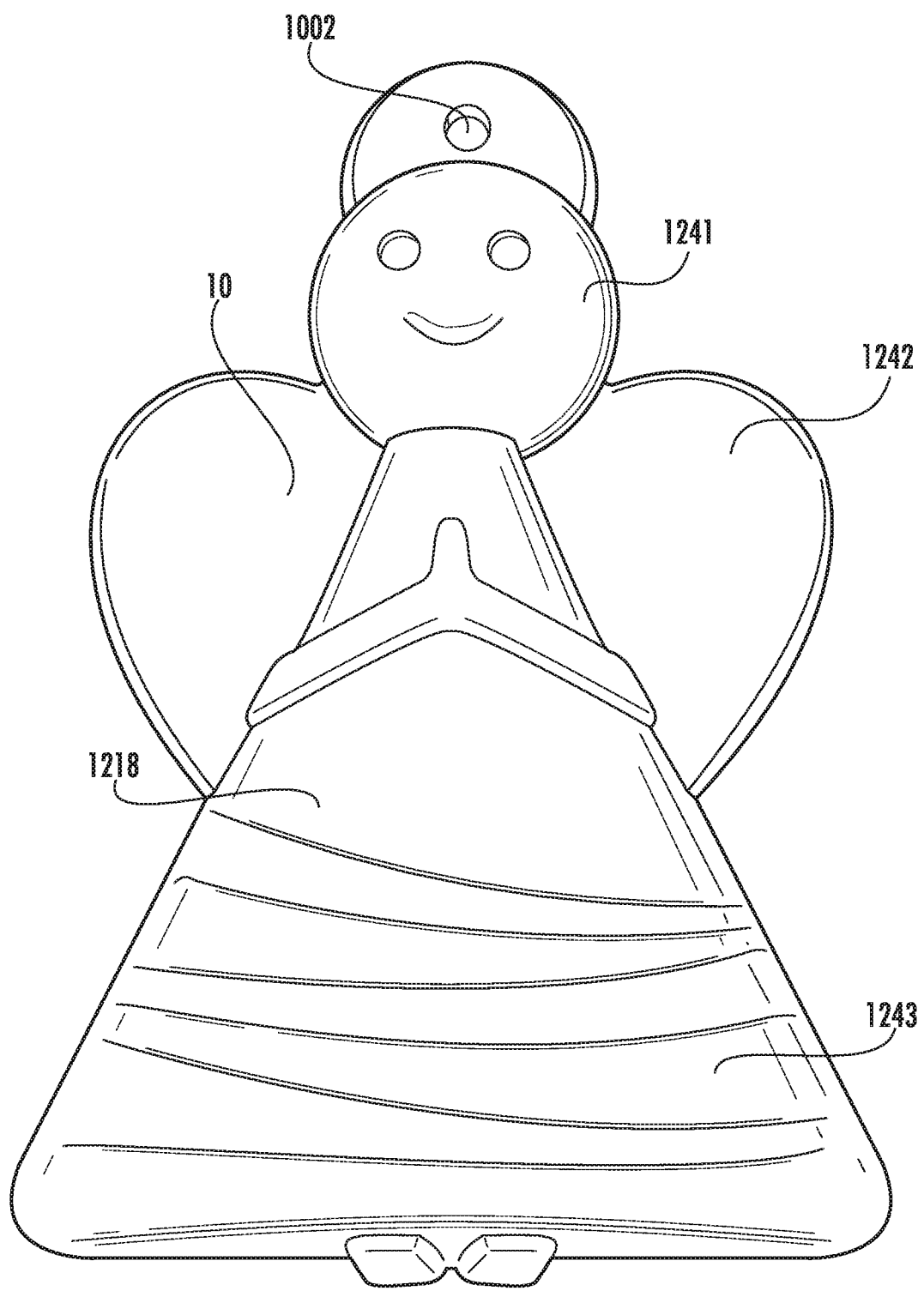
FIG. 73 is a front view of an article, according to certain embodiments of the present invention.
Figure 74:
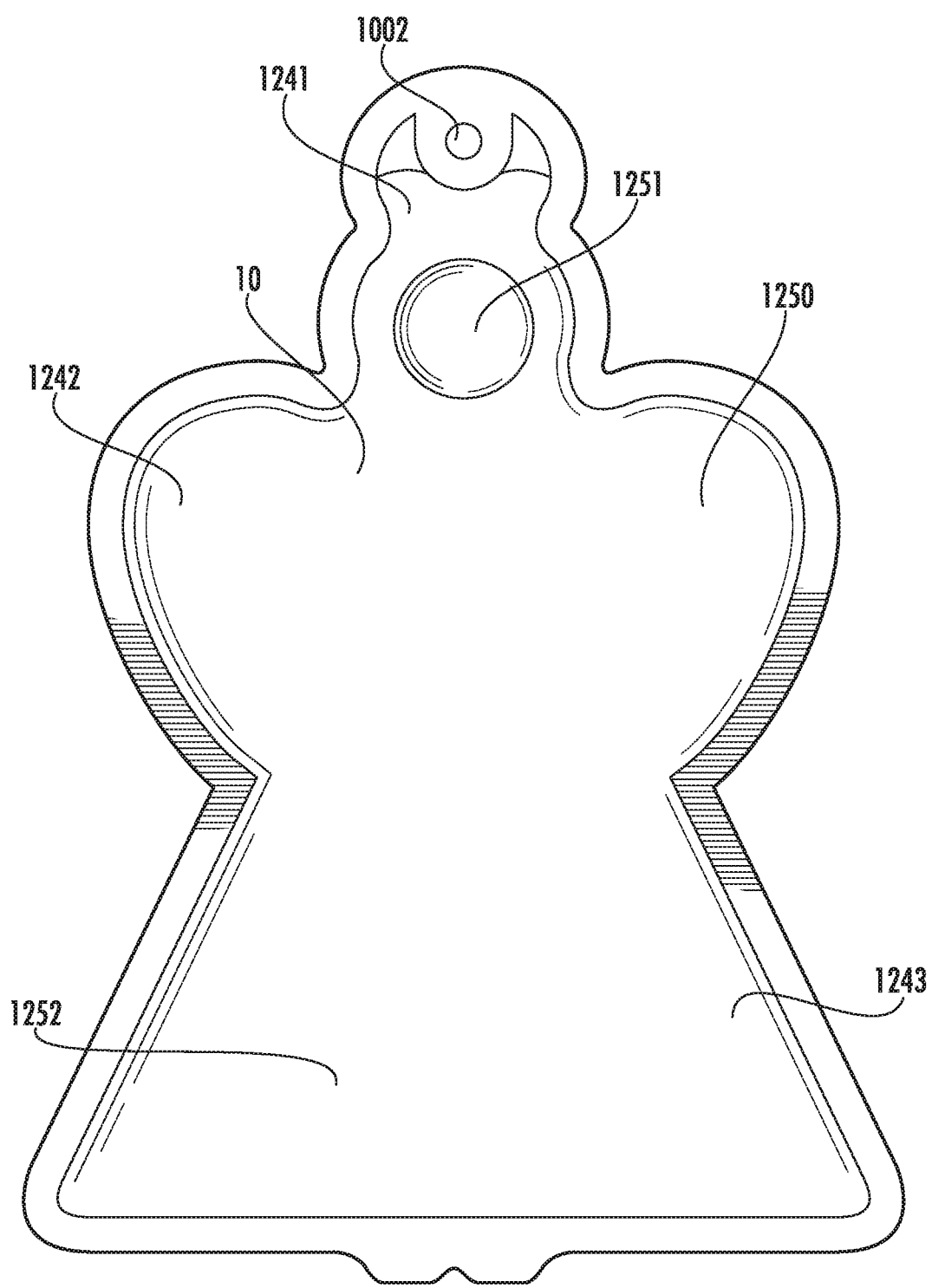
FIG. 74 is a rear view of the article of FIG. 73.

FIGS. 73 and 74 show an example of an article 10 formed in the shape of an angel (see also FIGS. 24-28, 34, 35, 37, 40). In some embodiments, the second density zone 1242 corresponds to the wings of the angel and has the highest density of the article 10. The first and third density zones 1241 and 1243 shown in FIGS. 73 and 74 have lower densities than the second density zone 1242. In some embodiments, the face/head of the angel (first density zone 1241) has a low density and the dress/body of the angel (third density zone 1243) has a moderate density that is greater than the density of the first density zone 1241 but less than the density of the second density zone 1242.

In some embodiments, the first density zone 1241 is approximately 0.6 g/cm$^3$ to 0.9 g/cm$^3$ and the second density zone 1242 is approximately 1.0 g/cm$^3$ to 1.2 g/cm$^3$. In certain embodiments, the first density zone 1241 is approximately 0.7 g/cm$^3$ to 0.75 g/cm$^3$ and the second density zone 1242 is approximately 1.05 g/cm$^3$ to 1.1 g/cm$^3$. As the density of article 10 increases, the maximum amount of fragrance (liquid, such as volatile composition 24) that can be absorbed into article 10 decreases. In some embodiments, after liquid has been absorbed, the first density zone 1241 has a percent fragrance load of approximately 50%-54% and the second density zone 1242 has a percent fragrance load of approximately 42%-46%. In certain embodiments, after liquid has been absorbed, the first density zone 1241 has a percent fragrance load of approximately 51.5%-52.5% and the second density zone 1242 has a percent fragrance load of approximately 43.5%-44.5%.

Figure 50:
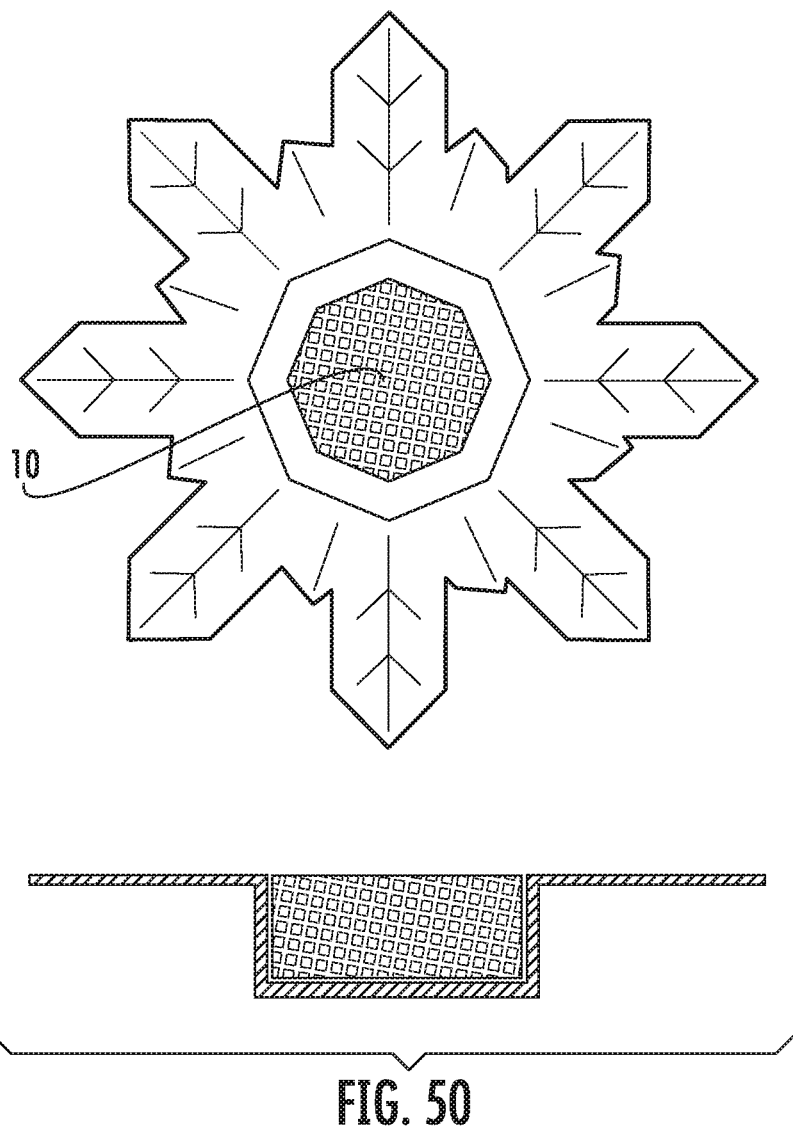
FIG. 50 includes top and side views of an article combined with a backing layer and holder, according to certain embodiments of the present invention.
Figure 51A:
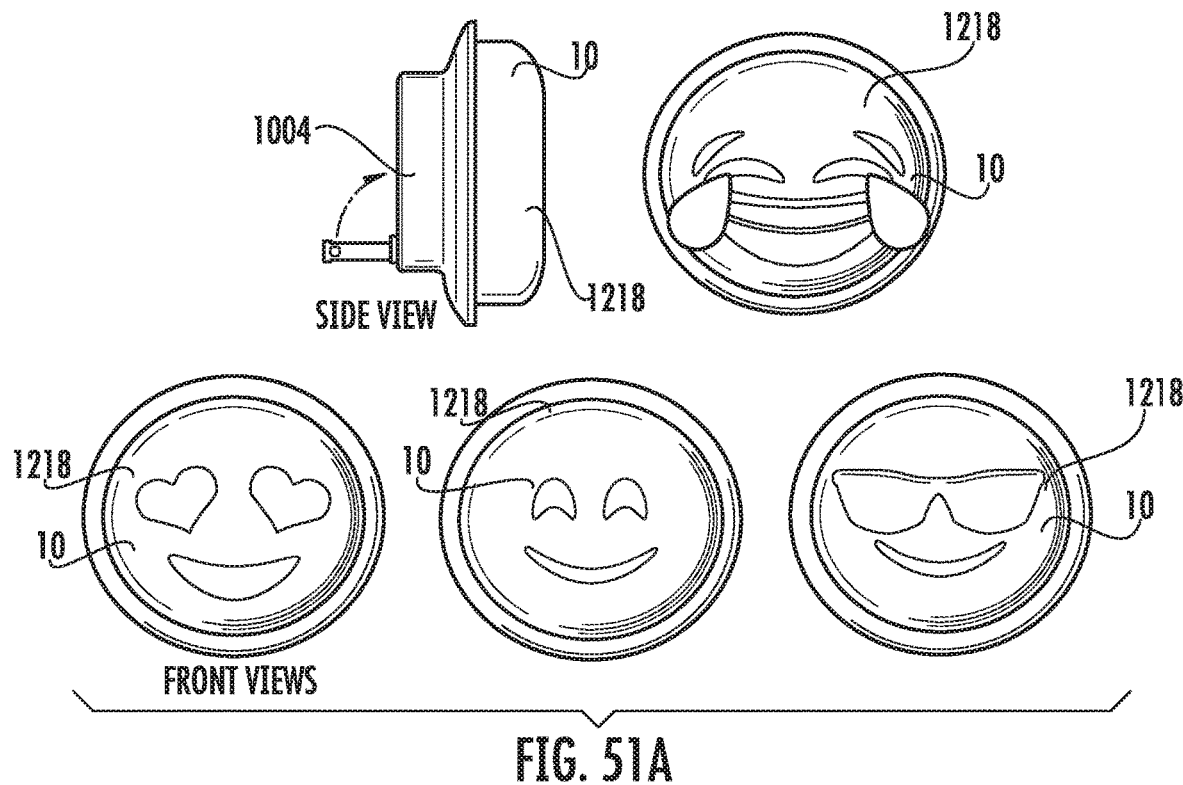
FIGS. 51A and 51B include front and side images of articles with a variety of shapes and coloration and a plug-in heating element, according to certain embodiments of the present invention.
Figure 51B:
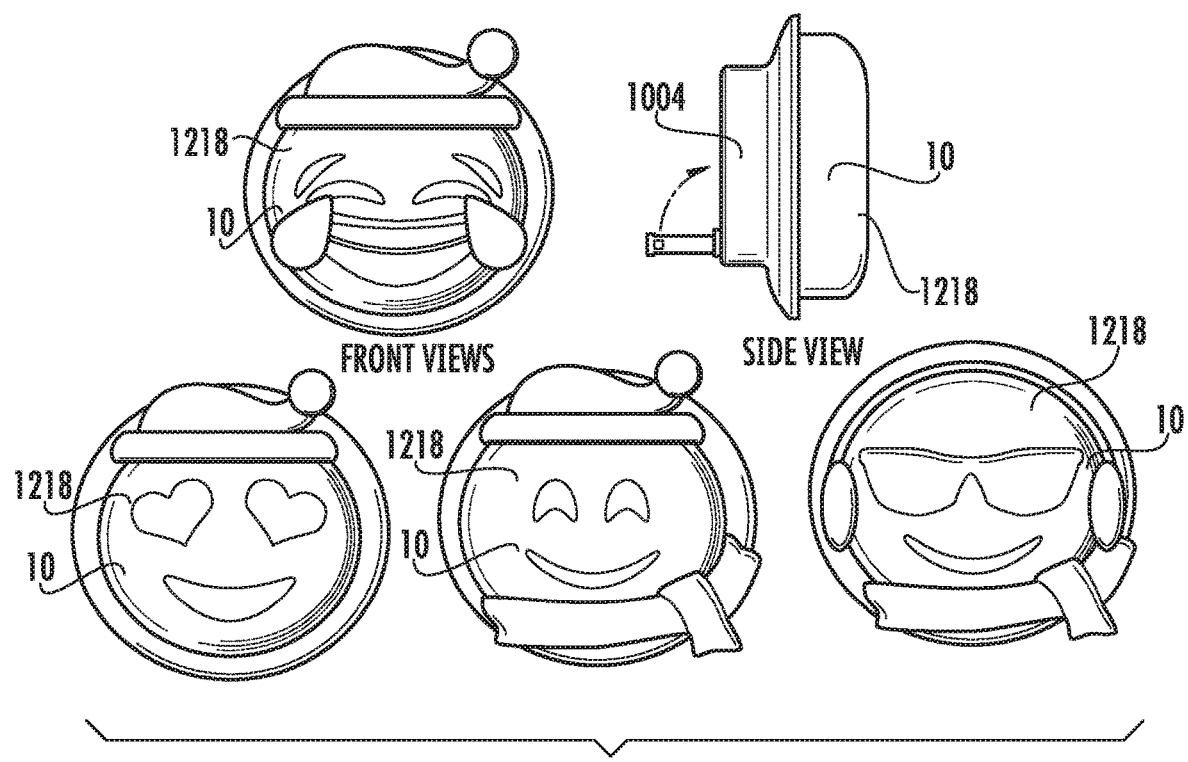
Figure 52A:
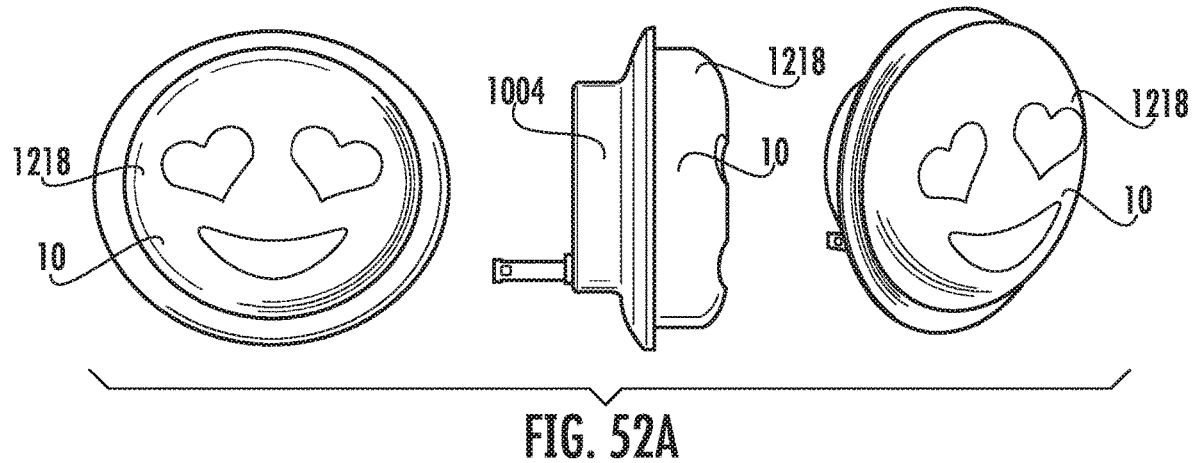
FIGS. 52A and 52B include front, side, and perspective images of articles with a variety of shapes and coloration and a plug-in heating element, according to certain embodiments of the present invention.
Figure 52B:
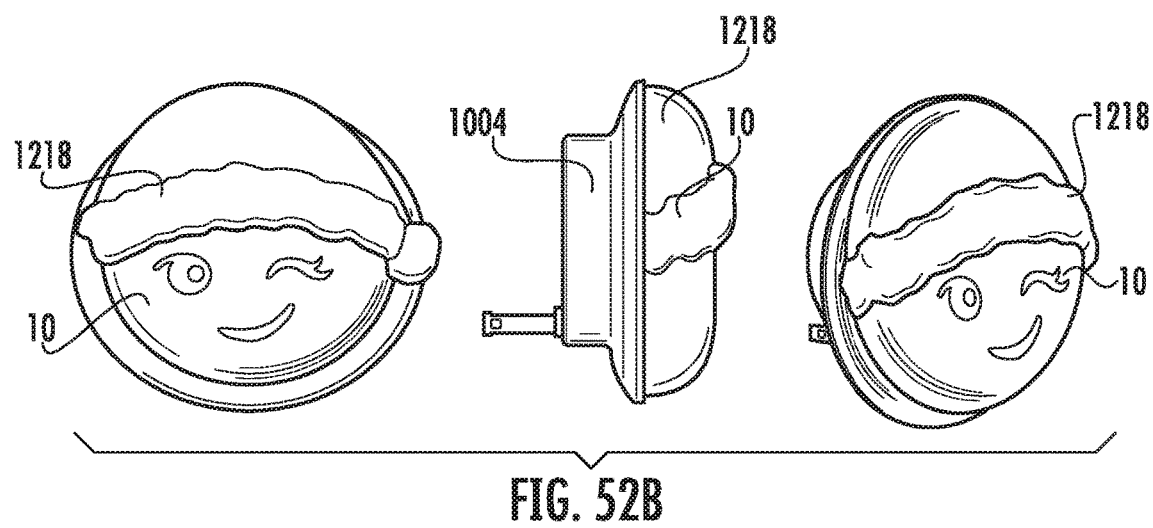
Figure 53:
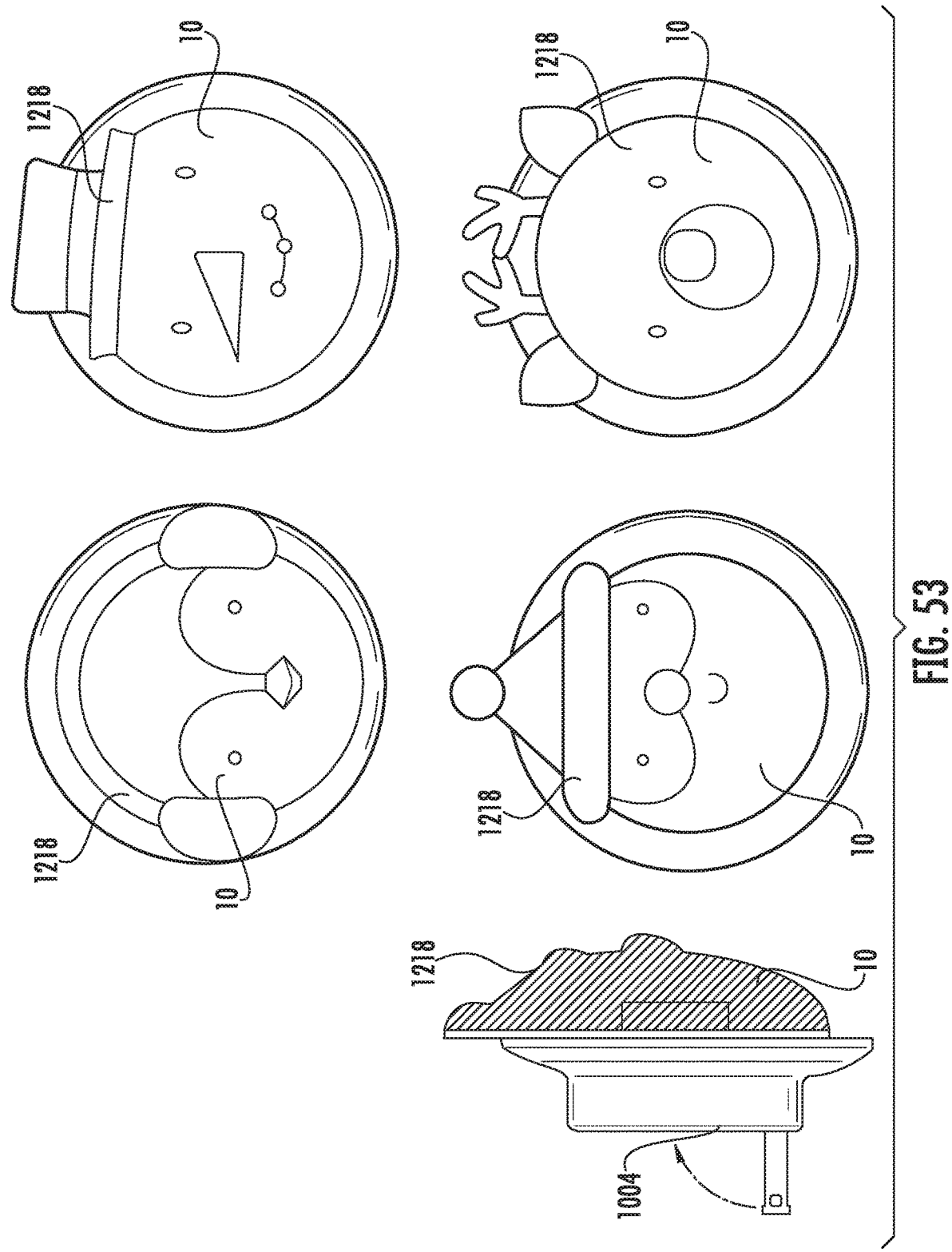
FIG. 53 includes front and side images of articles with a variety of shapes and coloration and a plug-in heating element, according to certain embodiments of the present invention.
Figure 57:
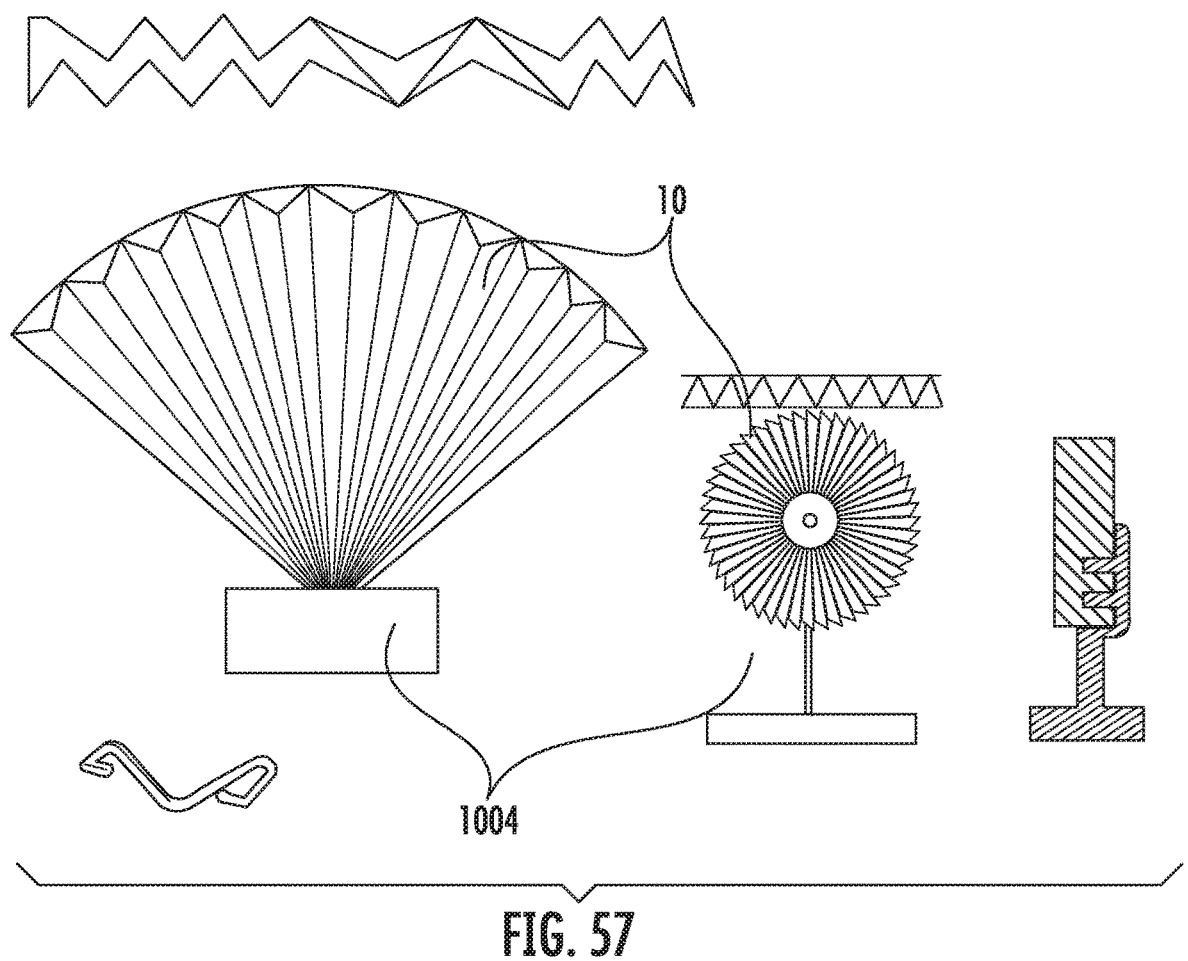
FIG. 57 includes a sketch of an article forming blades of a fan, according to certain embodiments of the present invention.
Figure 58:
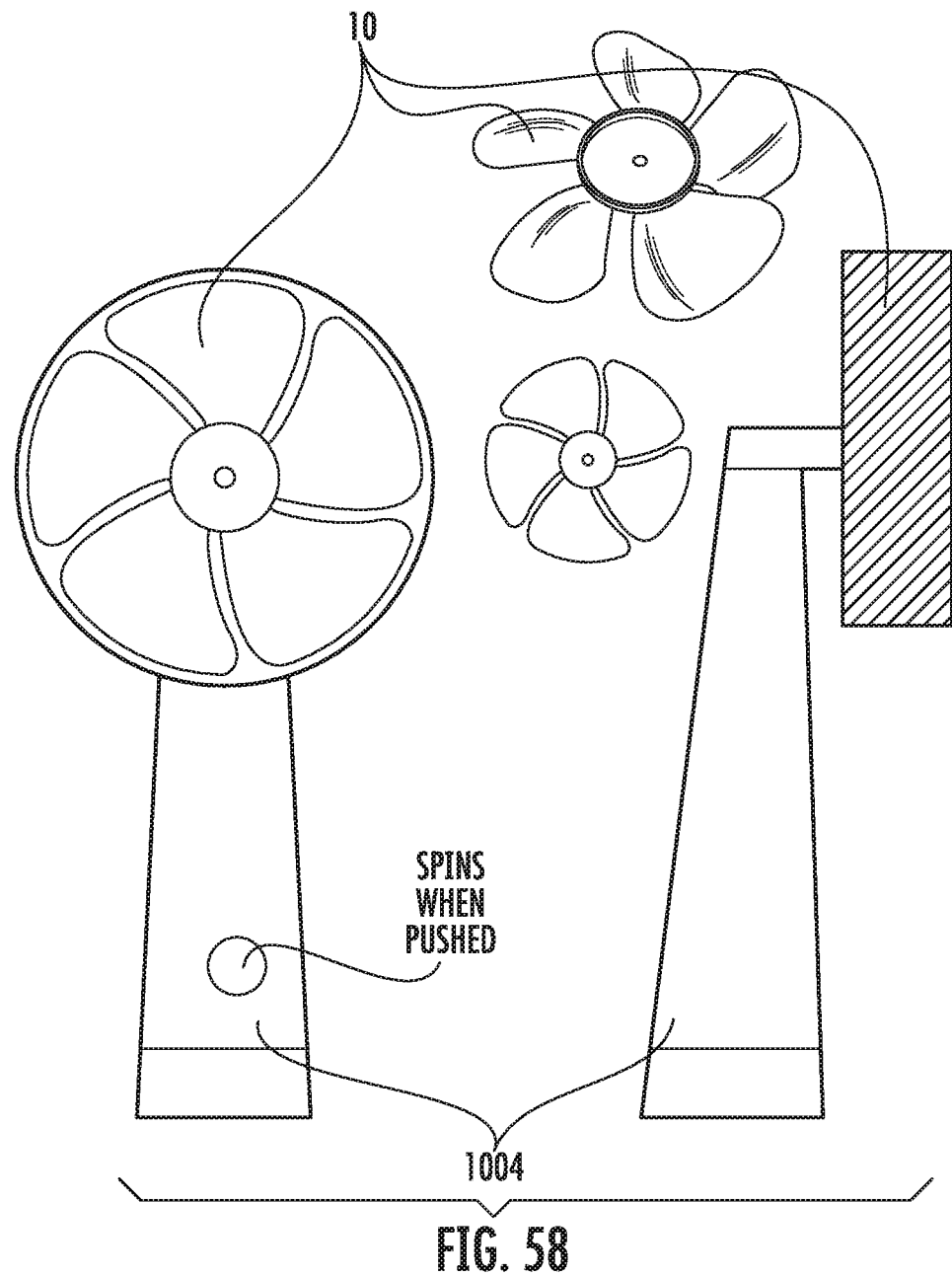
FIG. 58 includes a sketch of an article forming blades of a fan, according to certain embodiments of the present invention.
Figure 59:
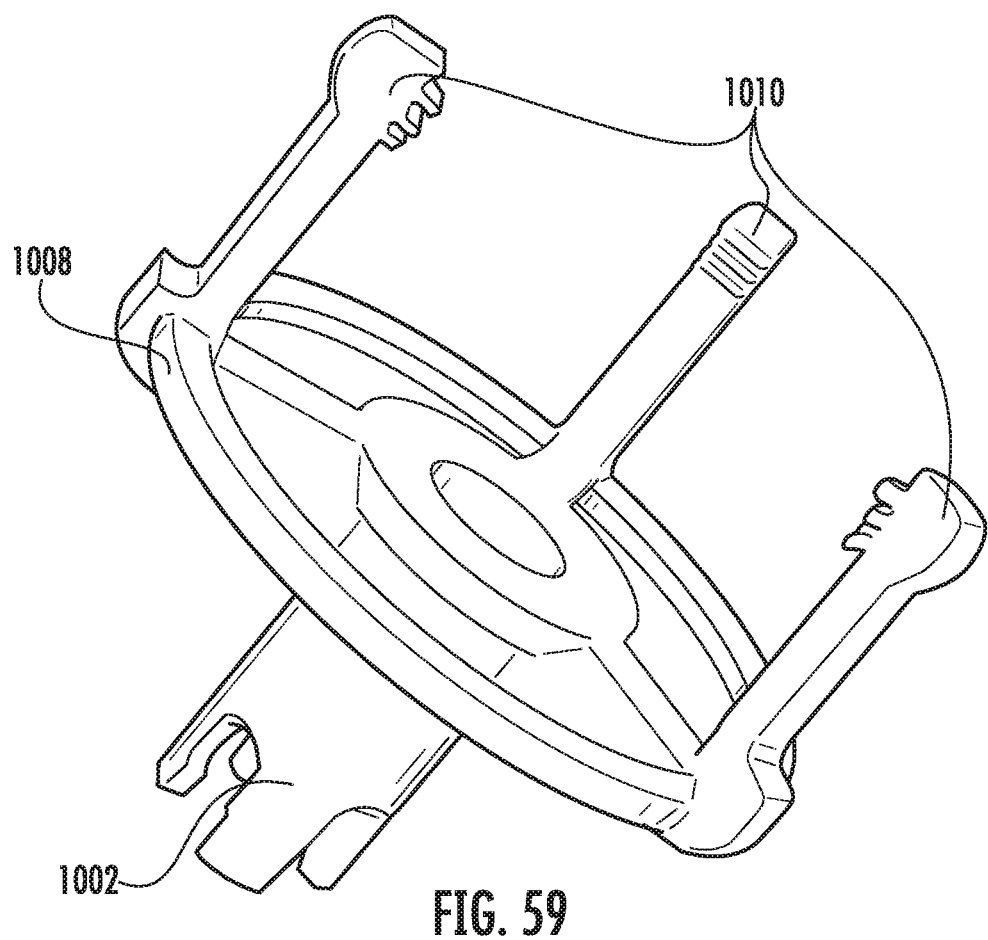
FIG. 59 is a perspective view of a support structure for an article, according to certain embodiments of the present invention.
Figure 60:
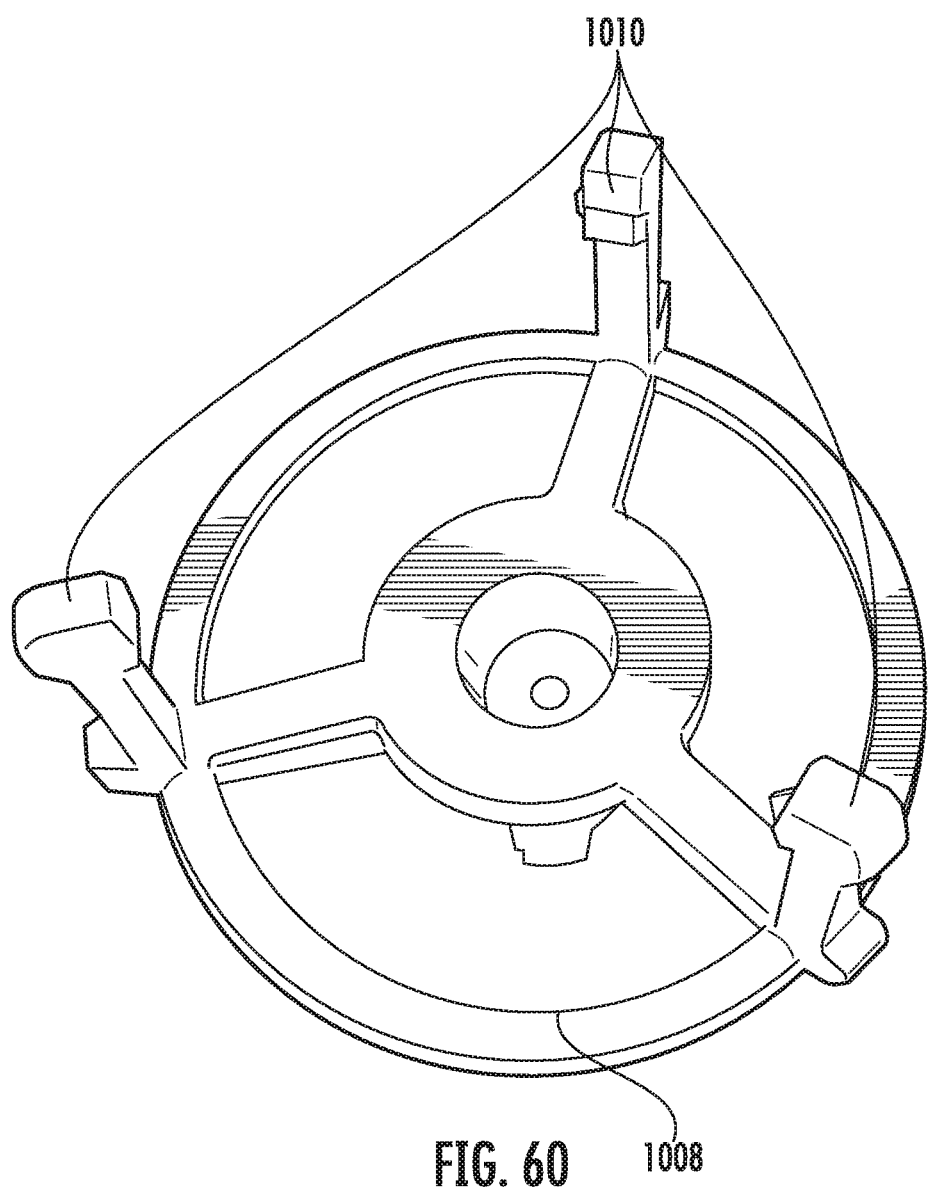
FIG. 60 is a top view of the support structure of FIG. 59.
Figure 61:
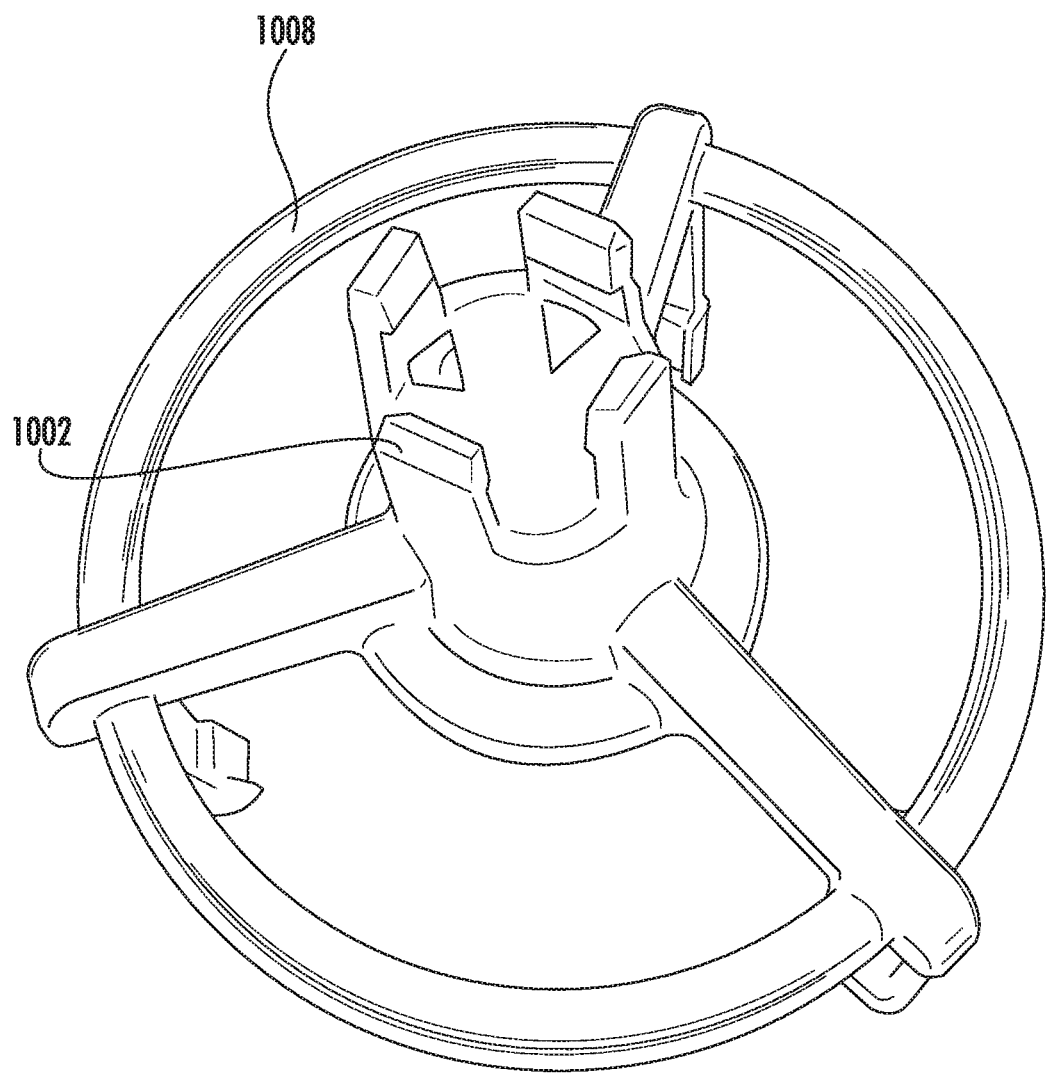
FIG. 61 is a bottom view of the support structure of FIG. 59.
Figure 62:
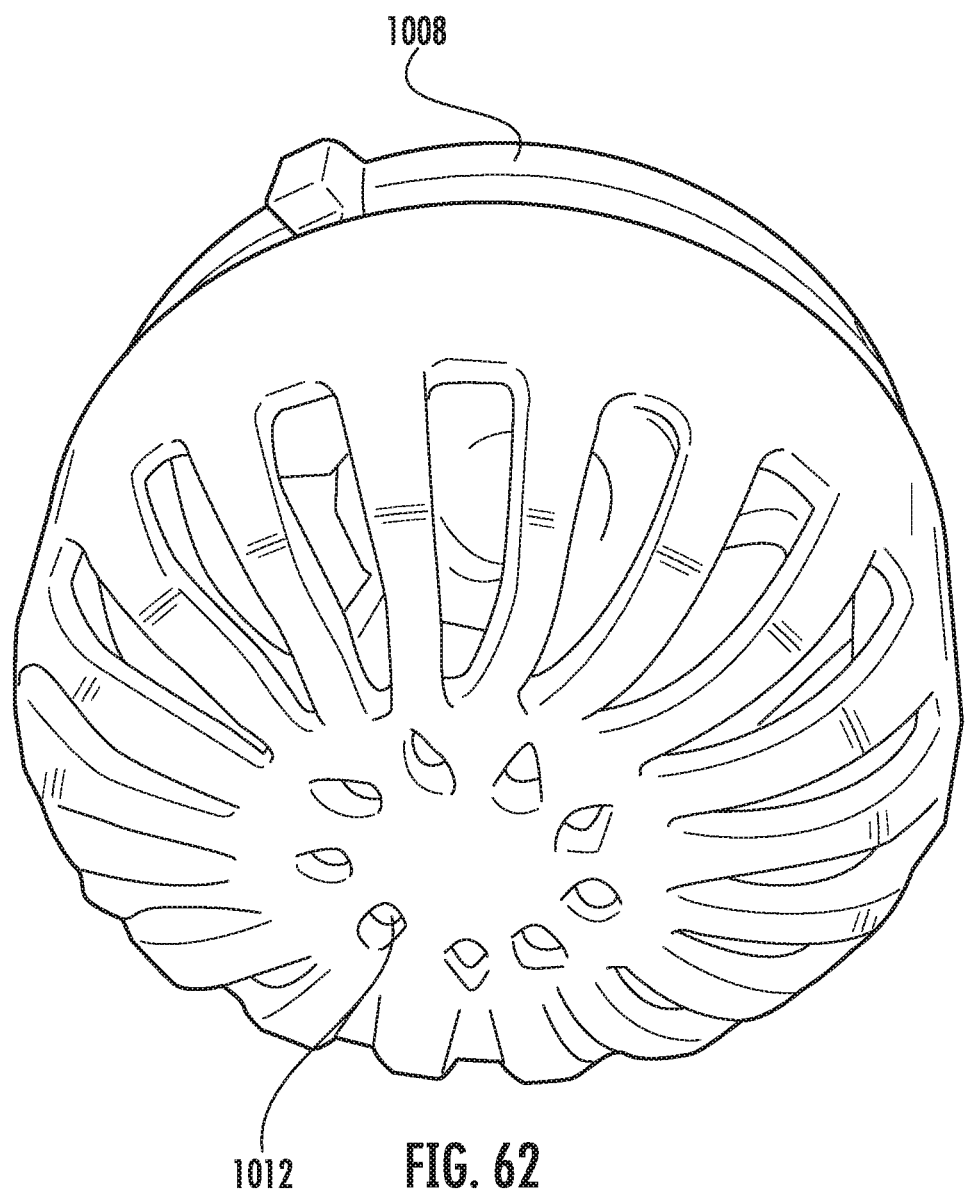
FIG. 62 is a front view of a decorative covering attached to the support structure of FIG. 59.
Figure 63:
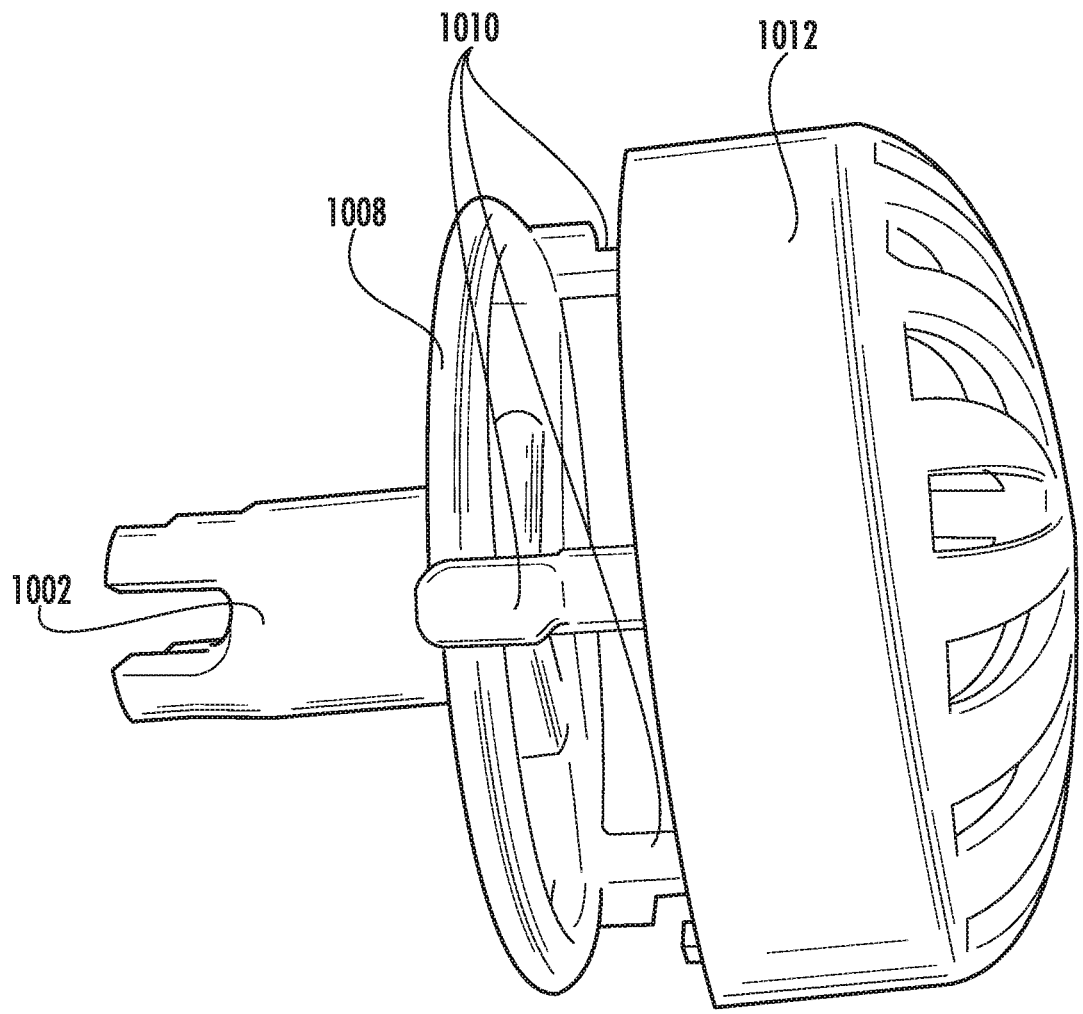
FIG. 63 is a side view of the decorative covering and support structure of FIG. 62.
Figure 64:
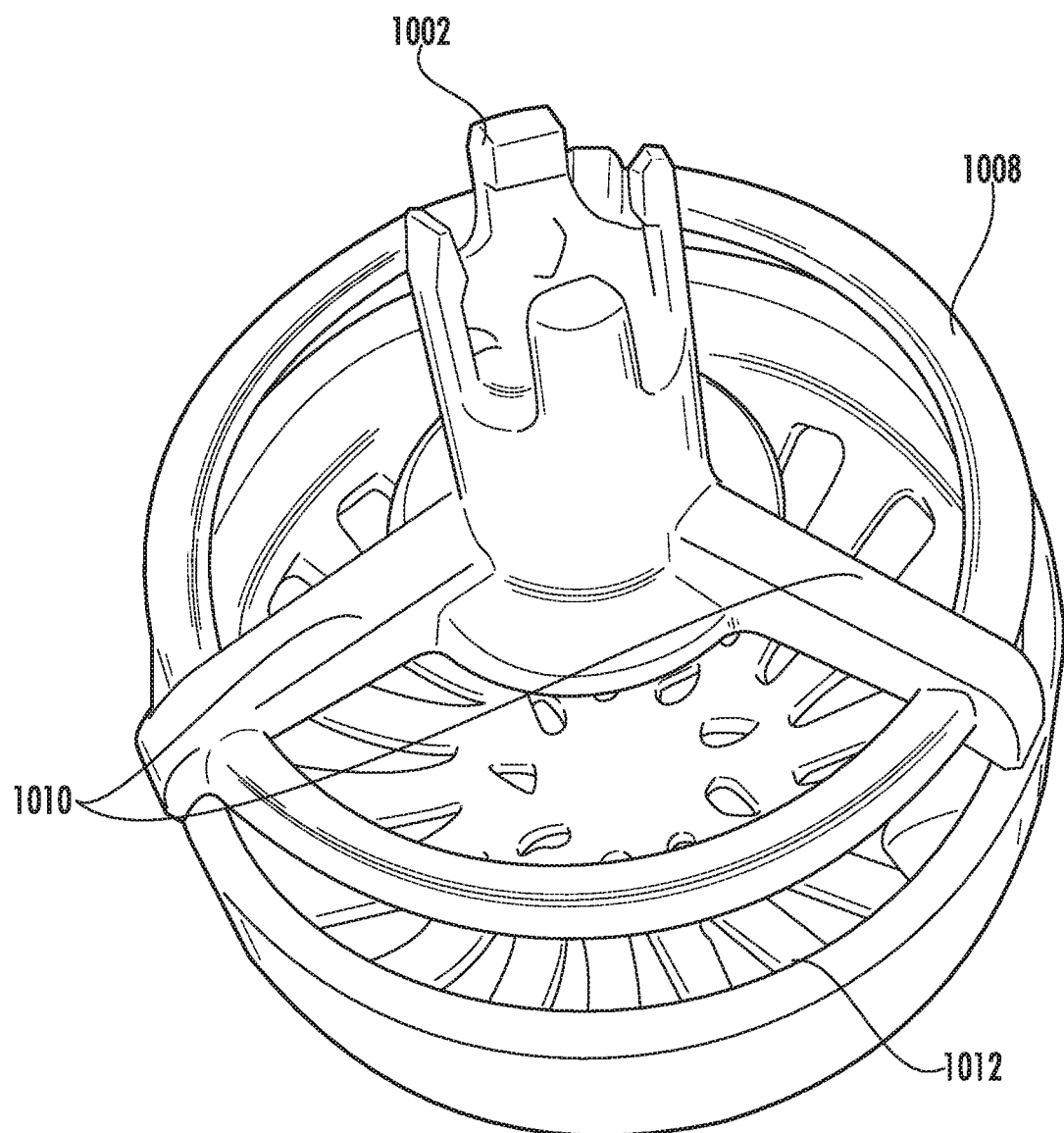
FIG. 64 is a bottom view of the decorative covering and support structure of FIG. 62.
Figure 76:
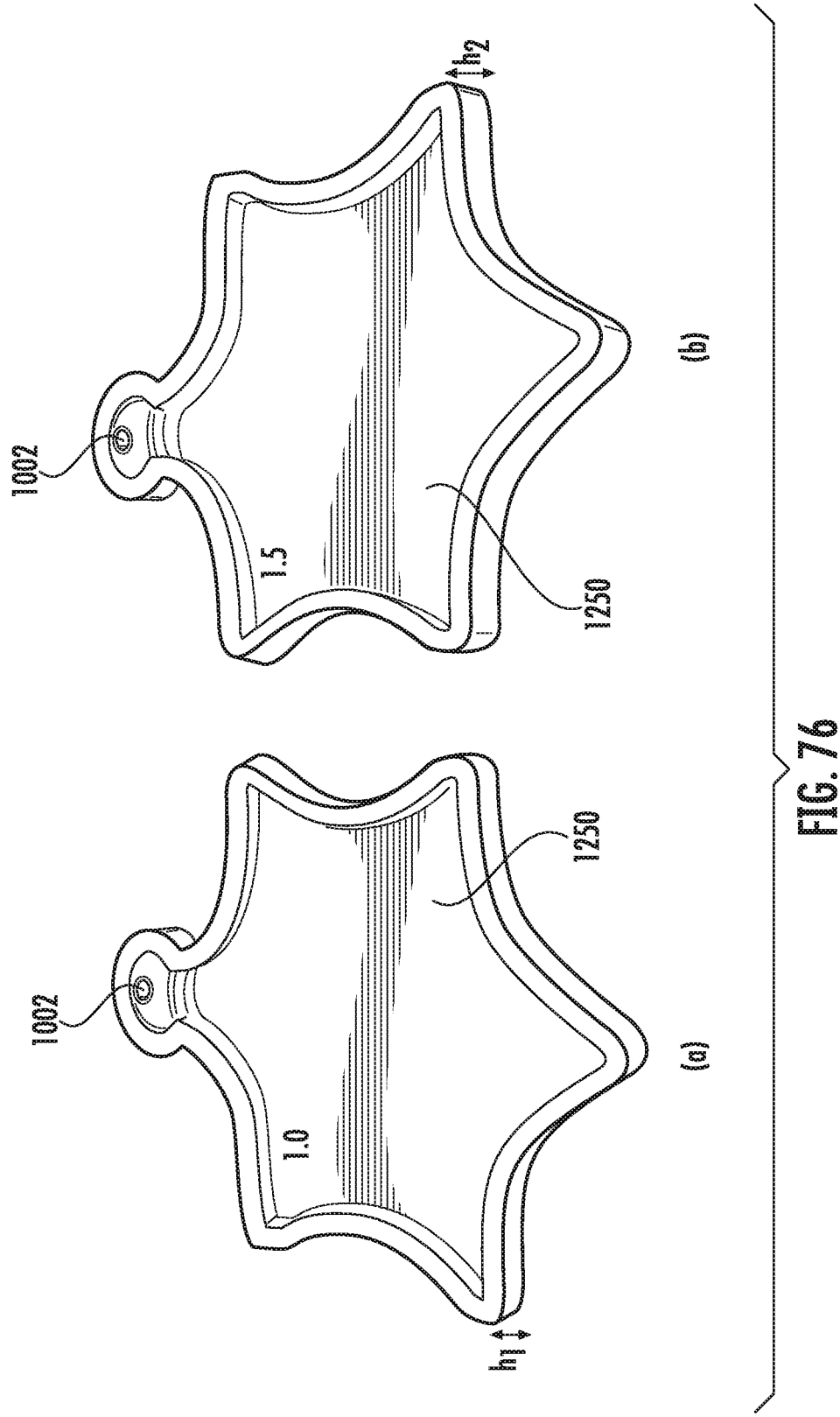
FIG. 76 is a rear view of the article of FIG. 75.

FIGS. 75 and 76 show examples of an article 10 formed in the shape of a snowflake (see also FIG. 50). These figures show two versions of the article 10, version (a) and version (b) where version (b) has a height/thickness $h_2$ that is larger than the height $h_1$ of version (a). In some embodiments, $h_2$ is approximately 50% larger than $h_1$. In some examples, $h_2$ is approximately 1.5 mm and $h_1$ is approximately 1 mm. Version (a) has a first density zone 1241 and a second density zone 1242 where the second density zone 1242 has a higher density than the first density zone 1241. Version (b) has a third density zone 1243 and a fourth density zone 1244 where the fourth density zone 1244 has a higher density than the third density zone 1243. The increased height/thickness of version (b) dictates that the third density zone 1243 has a lower density than the first density zone 1241 of version (a), which allows for better color contrast between third density zone 1243 and fourth density zone 1244 (compared to the contrast between first density zone 1241 and second density zone 1242).

The article 10 may also include a channel 1250 on the rear side (see FIGS. 74 and 76). The shape of the channel 1250 may approximately match the perimeter of the article 10 (as shown in FIGS. 74 and 76 with an offset from the perimeter on the rear side of the article 10), although this is not necessary. In some embodiments, during the manufacturing process of the article 10, a specific amount of volatile composition 24 (or a combination of volatile composition 24 and an oil soluble dye) may be poured into the channel 1250. As shown in FIG. 74, the channel 1250 may include at least one auxiliary channel 1251, 1252. The auxiliary channels 1251, 1252 may ensure liquid poured into the channel accumulates in specific regions and/or may reduce overall thickness of the article 10 in specific areas. Reducing a local thickness of the article 10 increases the compression in the local area thus increasing density of the article 10 at the desired location, which allows for greater detail surface detail to be molded at the exterior-facing surface 1218. For example, the first auxiliary channel 1251 may be located opposite of the face of the angel thus allowing facial features (e.g., mouth, eyes, etc.) to be molded into the exterior-facing surface 1218 (see FIGS. 73 and 74). Similarly, the second auxiliary channel 1252 may be located opposite of the dress of the angel thus allowing features (e.g., stripes, etc.) to be molded into the exterior-facing surface 1218 (see FIGS. 73 and 74). In some embodiments, the first auxiliary channel 1251 may have an approximately circular (2D) or partially spherical (3D) shape. In certain embodiments, the second auxiliary channel 1252 may have an approximately triangular (2D) or partially conical (3D) shape. The article 10 may also be submerged into a container of volatile composition 24 (or a combination of volatile composition 24 and an oil soluble dye). One or both of the pouring of the volatile composition 24 into the channel or submerging the article 10 into the container may be completed by a robotic device.

As described above, the density of the article 10 affects the amount of liquid fragrance that can be absorbed. In some embodiments, after the volatile composition 24 (or the combination of volatile composition 24 and the oil soluble dye) is added, the overall articles 10 shown in FIGS. 73-76 are approximately 30%-60% liquid (by weight). Some examples of the articles 10 may have 40% liquid by weight while other articles 10 may have 50% liquid by weight. In some embodiments, the article 10 has an internal reservoir capable of receiving up to 5-15 g of volatile composition 24 (or the combination of volatile composition 24 and the oil soluble dye). In some embodiments, the internal reservoir of the article 10 is capable of receiving up to 9 g of volatile composition 24 (i.e., the maximum liquid capacity). In some embodiments, the article 10 is designed to absorb approximately ⅔ of maximum liquid capacity. In some embodiments, the article 10 is designed to absorb approximately 6 g of volatile composition 24.

The channel 1250 may be designed such that the volume of the channel 1250 approximately corresponds to the maximum liquid capacity of the article 10. In some cases, the volume of the channel 1250 approximately corresponds to the desired amount of liquid to be absorbed by the article 10 during the manufacturing process, while in other embodiments, the volume of the channel 1250 is less than the desired amount of liquid to be absorbed by the article 10 during the manufacturing process based on the assumption that absorption begins immediately when liquid is poured into the channel.

B. Volatile Composition

The volatile composition 24 may include, but is not limited to fragrances, flavor compounds, odor-eliminating compounds, aromatherapy compounds, natural oils, water-based scents, odor neutralizing compounds, and outdoor products (e.g., insect repellent).

As used herein, "volatile substance" refers to any compound, mixture, or suspension of compounds that are odorous, or any compound, mixture, or suspension of compounds that cancel or neutralize odorous compounds, such as any compound or combination of compounds that would produce a positive or negative olfactory sense response in a living being that is capable of responding to olfactory compounds, or that reduces or eliminates such olfactory responses.

A volatile composition as used herein comprises one or more volatile substances, and is generally a composition that has a smell or odor, which may be volatile, which may be transported to the olfactory system of a human or animal, and is generally provided in a sufficiently high concentration so that it will interact with one or more olfactory receptors.

A fragrance may comprise an aroma or odorous compound, mixture or suspension of compounds that is capable of producing an olfactory response in a living being capable of responding to olfactory compounds, and may be referred to herein as odorant, aroma, or fragrance. A fragrance composition may include one or more than one of the fragrance characteristics, including top notes, mid notes or heart, and dry down or base notes. The volatile composition 24 may comprise other diluents or additives, such as solvents or preservatives.

Examples of volatile compositions 24 useful in the present invention include, but are not limited to esters, terpenes, cyclic terpenes, phenolics, which are also referred to as aromatics, amines and alcohols. Further examples include, but are not limited to furaneol 1-hexanol, cis-3-Hexen-1-ol, menthol, acetaldehyde, hexanal, cis-3-hexenal, furfural, fructone, hexyl acetate, ethyl methylphenylglycidate, dihydrojasmone, wine lactone, oct-1-en-3-one, 2-Acetyl-1-pyrroline, 6-acetyl-2,3,4,5-tetrahydropyridine, gamma-decalactone, gamma-nonalactone, delta-octalactone, jasmine, massoia lactone, sotolon ethanethiol, grapefruit mercaptan, methanethiol, 2-methyl-2-propanethiol, methylphosphine, dimethylphosphine, methyl formate, nerolin tetrahydrothiophene, 2,4,6-trichloroanisole, substituted pyrazines, methyl acetate, methyl butyrate, methyl butanoate, ethyl acetate, ethyl butyrate, ethyl butanoate, isoamyl acetate, pentyl butyrate, pentyl butanoate, pentyl pentanoate, isoamyl acetate, octyl acetate, myrcene, geraniol, nerol, citral, lemonal, geranial, neral, citronellal, citronellol, linalool, nerolidol, limonene, camphor, terpineol, alpha-ionone, terpineol, thujone, benzaldehyde, eugenol, cinnamaldehyde, ethyl maltol, vanillin, anisole, anethole, estragole, thymoltrimethylamine, putrescine, diaminobutane, cadaverine, pyridine, indole and skatole. Most of these are organic compounds and are readily soluble in organic solvents, such as alcohols or oils. Fragrance includes pure fragrances, such as those including essential oils, and are known to those skilled in the art. Water-based odorous compounds and other odorous compositions are also contemplated by the present invention.

Fragrance oils as olfactory-active compounds or compositions usually comprise many different perfume raw materials. Each perfume raw material used differs from another by several important properties including individual character and volatility. By bearing in mind these different properties, and others, perfume raw materials may be blended to develop a fragrance oil with an overall specific character profile. To date, characters are designed to alter and develop with time as the different perfume raw materials evaporate from the substrate and are detected by the user. For example, perfume raw materials which have a high volatility and low substantivity are commonly used to give an initial burst of characters such as light, fresh, fruity, citrus, green, or delicate floral to the fragrance oil, which are detected soon after application. Such materials are commonly referred to in the field of fragrances as "top notes." By way of a contrast, the less volatile, and more substantive, perfume raw materials are typically used to give characters such as musk, sweet, balsamic, spicy, woody or heavy floral to the fragrance oil, which may also be detected soon after application, but also last far longer. These materials are commonly referred to as "middle notes" or "base notes." Highly skilled perfumers are usually employed to carefully blend perfume raw materials so that the resultant fragrance oils have the desired overall fragrance character profile. The desired overall character is dependent both upon the type of composition in which the fragrance oil will finally be used and also the consumer preference for a fragrance.

In addition to the volatility, another important characteristic of a perfume raw material is its olfactory detection level, otherwise known as the odor detection threshold (ODT). If a perfume raw material has a low odor detection threshold, only very low levels are required in the gas phase, or air, for it to be detected by the human, sometimes as low as a few parts per billion. Conversely, if a perfume raw material has a high ODT, larger amounts or higher concentrations in the air of that material are required before it can be smelled by the user. The impact of a material is its function of its gas phase or air concentration and its ODT. Thus, volatile materials, capable of delivering large gas-phase concentrations, which also have low ODTs, are considered to be impactful. To date, when developing a fragrance oil, it has been important to balance the fragrance with both low and high volatility raw materials, as the use of too many high volatility materials may lead to a short lived, overwhelming scent. As such, the levels of high odor impact perfume raw materials within a fragrance oil have traditionally been restricted.

As used herein, the term "fragrance oil" relates to a perfume raw material, or mixture of perfume raw materials, that are used to impart an overall pleasant odor profile to a composition, preferably a cosmetic composition. As used herein, the term "perfume raw material" relates to any chemical compound which is odorous when in an un-entrapped state. For example, in the case of pro-perfumes, the perfume component is considered to be a perfume raw material, and the pro-chemistry anchor is considered to be the entrapment material. In addition, "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP," which is available from Daylight Chemical Information Systems Inc., Irvine Calif., USA. Octanol/water partition coefficients are described in more detail in U.S. Pat. No. 5,578,563.

Examples of residual "middle and base note" perfume raw materials include, but are not limited to ethyl methyl phenyl glycidate, ethyl vanillin, heliotropin, indol, methyl anthranilate, vanillin, amyl salicylate, coumarin. Further examples of residual perfume raw materials include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxylphenyl butanone, 8-cyclohexadecen-1-one, oxocyclohexadecen-2-one/habanolide, florhydral, intreleven aldehyde.

Examples of volatile "top note" perfume raw materials include, but are not limited to anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials include, but are not limited to phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, c is 1,3-oxathiane-2-methyl-4-propyl.

Other useful residual "middle and base note" perfume raw materials include, but are not limited to eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Other volatile "top note" perfume raw materials include, but are not limited to benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

In certain embodiments, the volatile composition 24 may comprise a fragrance component having a release rate ranging from 0.001 g/day to 2.0 g/day. The formulation of the fragrance may comprise any suitable combination of top, mid, and base note components.

In certain embodiments, the pulp base material 12 may be infused with more than one volatile composition 24 that is paired with a suitable zone 1206, 1208 within the pulp base material 12 to achieve a blended release rate designed to optimize the "top note" and "middle and base note" release rates.

As discussed above, the porosity (which may be controlled by fiber compactness, infusion of gas or gas-forming materials, refining, additives, or any other porosity-controlling method described above) may affect the uptake or load amount of the volatile composition 24, or may affect the rate of release of the volatile composition 24. For example, high porosity zone 1206, which has a lower fiber compactness, will provide an easier release of the volatile composition 24 because there are larger air passages between the fibers. Thus, a volatile composition 24 comprising mostly "middle and base note" components may be incorporated into the high porosity zone 1206 to provide an earlier release of the "middle and base note" components.

In contrast, low porosity zone 1208, which has a higher fiber compactness, will provide a more controlled release of the volatile composition 24 because the network of air passages through the fibers is tighter and more complex. Thus, a volatile composition 24 comprising mostly "top note" components may be incorporated into the low porosity zone 1208 to provide a slower release of the "top note" components.

In other words, the pulp base material 12 may be engineered with a plurality of zones, each zone having a uniquely designed pulp porosity that correlates to the desired release rate of the particular notes within the different volatile compositions 24.

In some embodiments, the design may be to create a simultaneous and sustained release of all notes, which may be optimized by pairing "top notes" with lower porosity zones, "middle notes" with medium porosity zones, and "base notes" with higher porosity zones.

In other embodiments, the design may be to create a staggered release of different scents over time, which may be optimized by reversing the pairing described above. In other words, the pulp base material 12 may include a pairing of "top notes" with higher porosity zones 1202, "middle notes" with medium porosity zones 1202, and "base notes" with lower porosity zones 1202.

The test results described in Example 2 demonstrate that a pulp base material 12 having a density of 0.36 g/mL generates a different release profile of a volatile composition with high and low molecular weight compounds, when compared to a pulp base material 12 having a density of 0.24 g/mL. In the fragrance industry, high molecular weight compounds are categorized as "base note" compounds, and low molecular weight compounds are categorized as "top note" volatile compounds.

Specifically, for samples containing only "base note" compound methyl cedryl ketone ("MCK") volatile composition 24, the lower density pulp base material samples released approximately 12 times more "base note" MCK than the higher density pulp base material samples.

For samples containing both "top note" compound ethyl acetate volatile composition 24 and "base note" compound methyl cedryl ketone ("MCK") volatile composition 24, the lower density pulp base material samples and the higher density pulp base material samples released the "base note" MCK at similar rates, while the lower density pulp base material samples released approximately 15 times more "top note" ethyl acetate than the higher density pulp base material samples.

Finally, the lower density pulp base material samples showed a faster release rate for all volatile compositions 24 over the higher density pulp base material samples.

Figure 79:
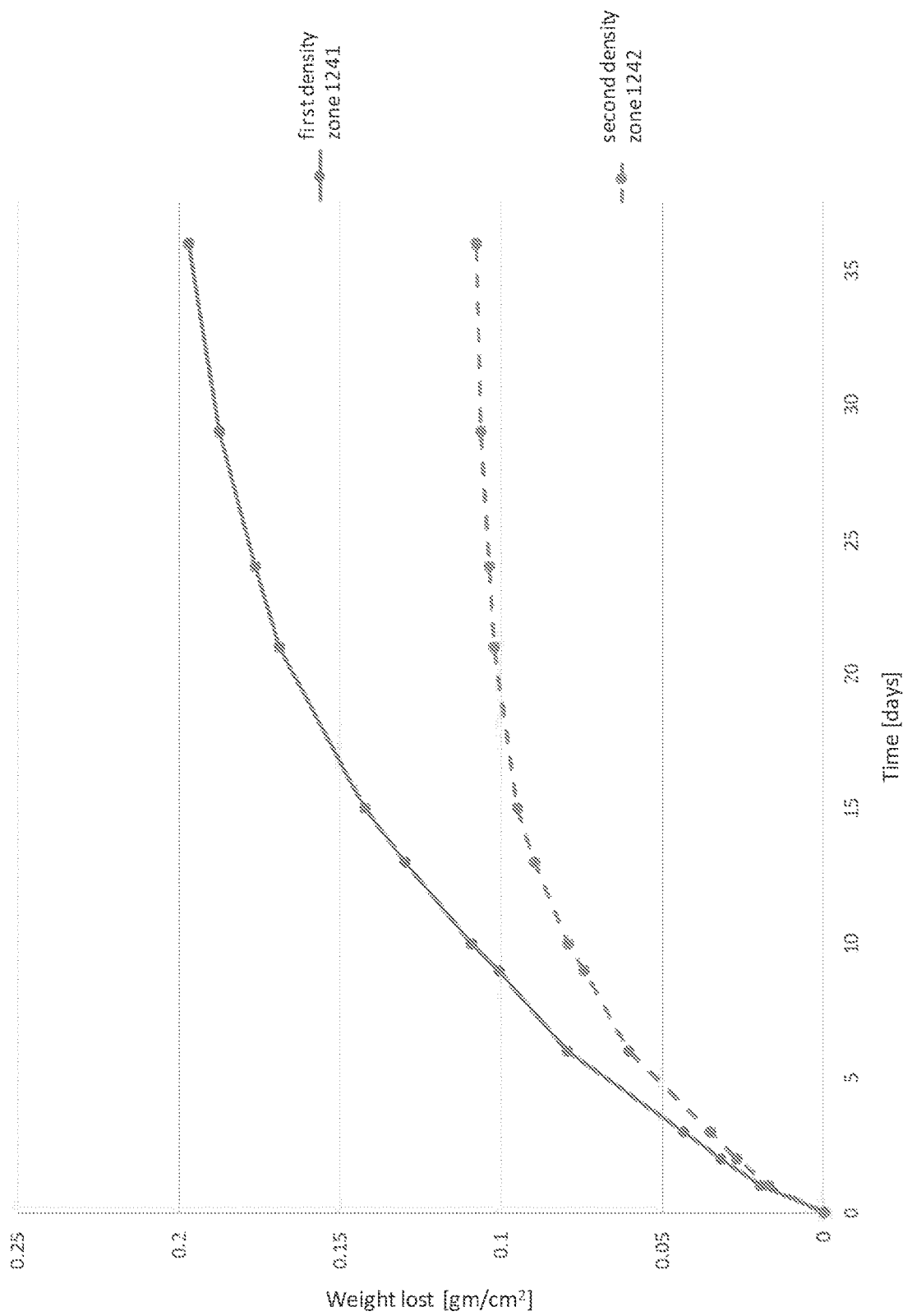
FIG. 79 is a graph showing weight loss data for two density zones according to certain embodiments of the present invention.
Figure 80:
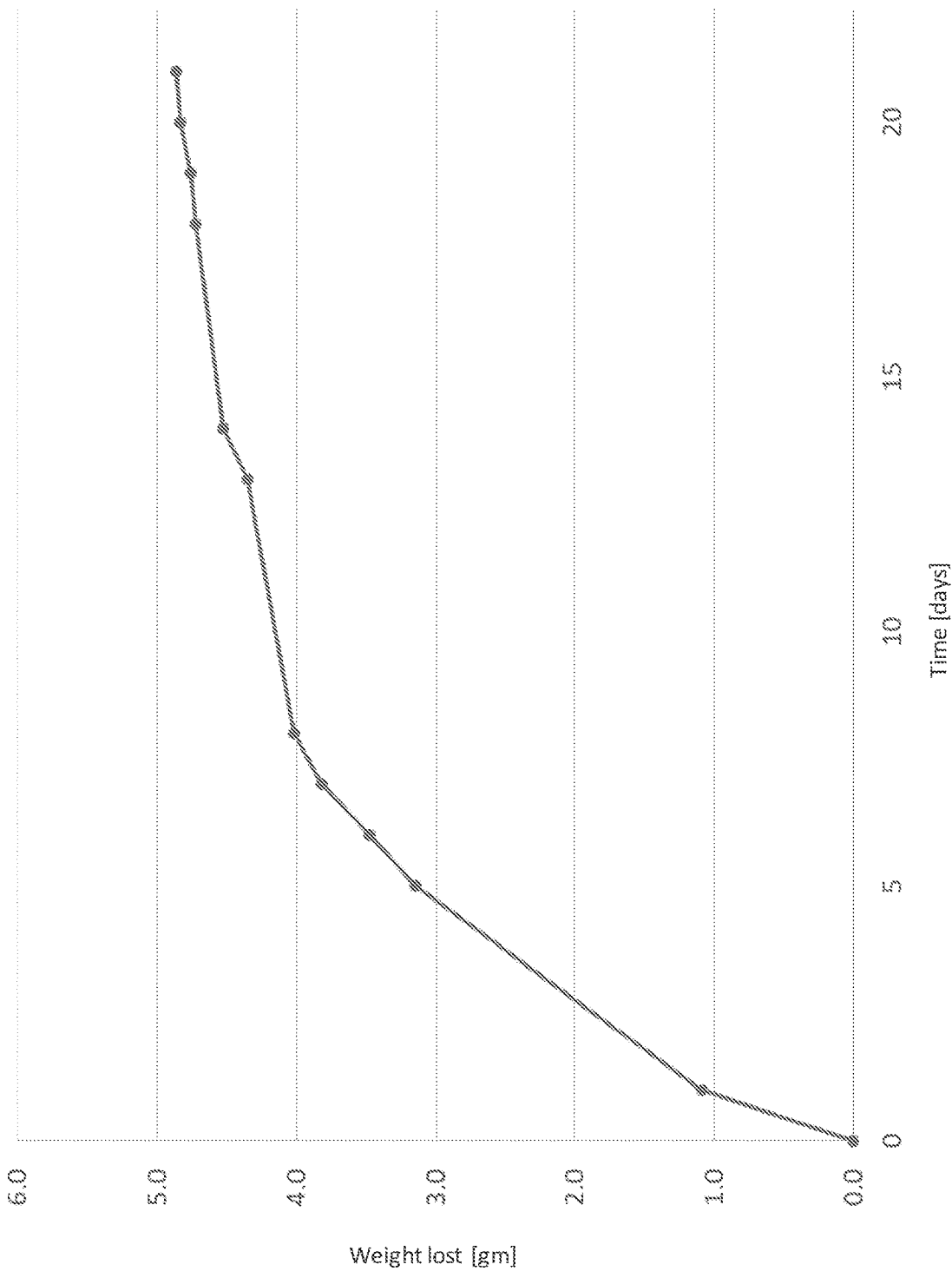
FIG. 80 is a graph showing weight loss data for an article according to certain embodiments of the present invention.

FIG. 79 shows weight loss data for first density zone 1241 and second density zone 1242. In some embodiments, the data shown in FIG. 79 is relevant to the embodiments shown in FIGS. 73 and 74. However, the data shown in FIG. 79 may be relevant to multiple embodiments. Because, as described above, first density zone 1241 has a lower density (higher porosity) and thus can absorb more liquid compared to the second density zone 1242, the first density zone 1241 exhibits a greater weight loss (per surface area). FIG. 79 also illustrates that the rate of the weight loss for second density zone 1242 reduces faster than the rate of the weight loss for first density zone 1241. FIG. 80 shows an example of the cumulative weight loss for an article 10 over a 21 day period. In some embodiments, the data shown in FIG. 80 is relevant to the embodiments shown in FIGS. 73 and 74. However, the data shown in FIG. 80 may be relevant to multiple embodiments.

EXAMPLES

Example 1. Synthesis of Pulp Matrix

Pulp material (15 g; southern hardwood; Sulfatate-H-J grade; Rayonier Performance Fibers, LLC) was added to a blender cup. A solution containing (i) colloidal silica (5 g; Snowtex®-O (silica 20% wt/wt in water); Nissan Chemical America Corporation), (ii) starch (5 g; Maltrin QD® M500 Maltodextrin NF; Grain Processing Corporation), (iii) baking powder (1 g; Clabber Girl Corporation), and (iv) water (221.5 g) was added to the blender cup. The content in the blender cup was blended to form a consistent pulp slurry, followed by removal of 100 g of excess solution. The final pulp slurry was added to a silicone mold, where the shape of the mold is a cylinder with dimensions 1.8 cm diameter, 1.3 cm height (volume: 3.31 cm$^3$). The amount of pulp slurry used to create a varying density pulp cylinder is provided in Table 1.

TABLE 1

Pulp mass and density of pulp cylinder matrix

| | Pulp slurry mass (g) | Pulp dry mass (g) | Density (g pulp/cm$^3$) |
|---|---|---|---|
| High density pulp cylinder | 10 | 1.2 | 0.36 |
| Low density pulp cylinder | 6 | 0.8 | 0.24 |

Example 2. Headspace Gas Chromatography/Mass Spectrometry (GC/MS) Valuation of Release of High and Low MW Ingredients from a Pulp Matrix The amount of release of a top note or base note volatile ingredient from the pulp matrix was evaluated using the standard method ASTM D4526-12 Standard for Determination of Volatiles in Polymers by Static Headspace Gas Chromatography. Headspace GC/MS experiments were carried out on Agilent instruments: headspace model 7697A, GC model 7850A, and MS model 5975C. The top note and base note ingredients selected are common ingredients used in all types of olfactive compositions in the fragrance industry. Ethyl acetate (CAS 141-78-6; MW 88.1 g/mol) is the top note ingredient that was tested, and methyl cedryl ketone (CAS 32388-5-9; MW 246.4 g/mol) is the base note ingredient that was tested. The base note ingredient represents the high end of the molecular weight spectrum for volatile ingredients, and the top note ingredient represents the low end of the molecular weight spectrum for volatile ingredients.

TABLE 2

Headspace GC/MS results demonstrating impact of packing density in pulp base material 12 on release profile of olfactive volatile compositions.

| Sample | Pulp matrix density (g/mL) | Compound injected (7 μL each) | GC/MS peak area (EA) | GC/MS peak area (MCK) | Amount EA detected (%) | Amount MCK detected (%) |
|---|---|---|---|---|---|---|
| EA control | NA | EA | 1191399736 | NA | 100 | NA |
| MCK control | NA | MCK | NA | 1437276114 | NA | 100 |
| 1 | 0.36 | EA | Below limit | NA | not detected | NA |
| 2 | 0.36 | MCK | NA | 21830631 | NA | 1.52 |
| 3 | 0.36 | EA/MCK | Below limit | 3915890 | not detected | 0.27 |
| 4 | 0.24 | EA | Below limit | NA | not detected | NA |
| 5 | 0.24 | MCK | NA | 270003206 | NA | 18.79 |
| 6 | 0.24 | EA/MCK | 186196145 | 4025104 | 15.63 | 0.28 |

EA = ethyl acetate;
MCK = methyl cedryl ketone;
NA = not applicable

Figure 66:
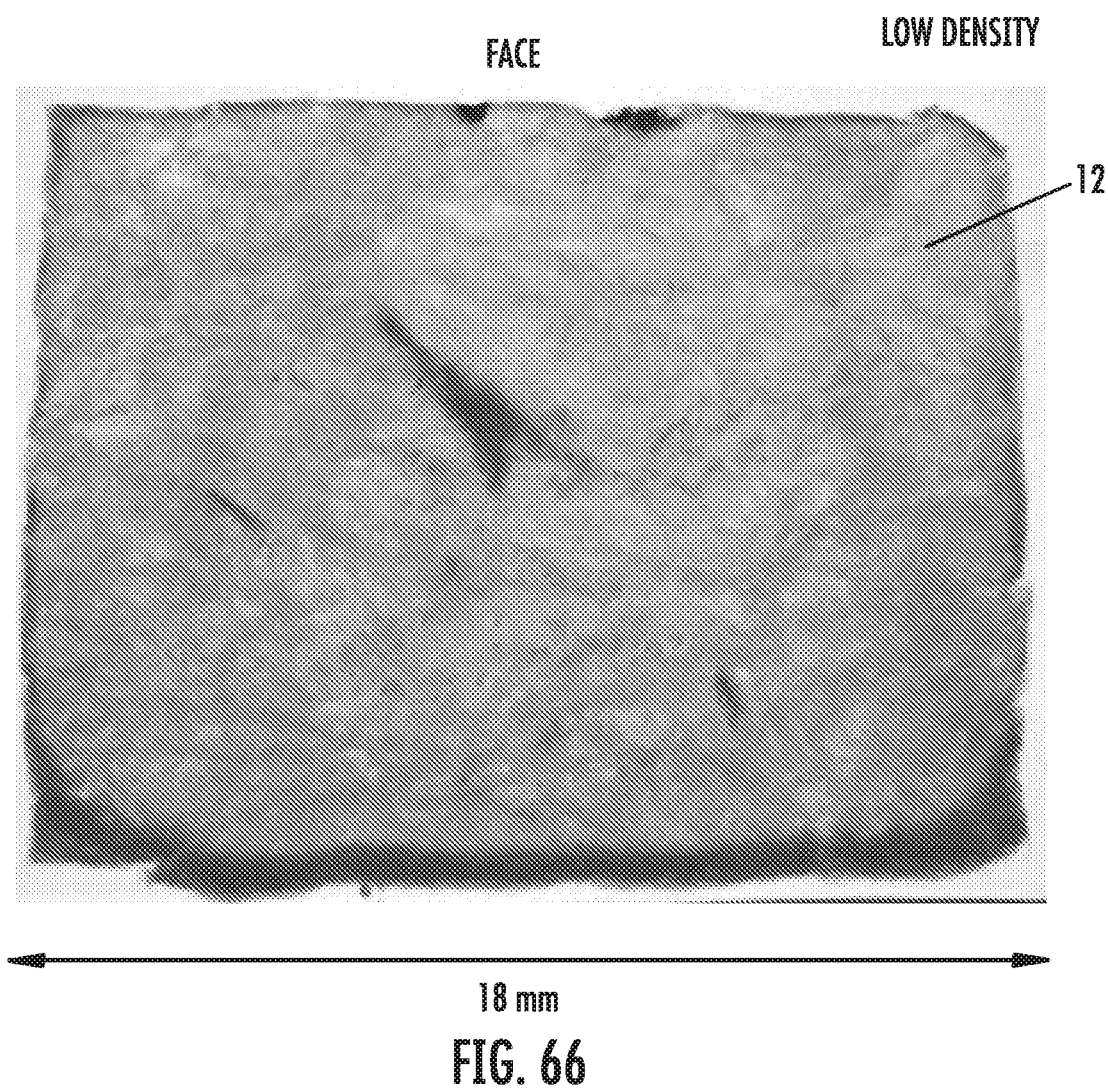
FIG. 66 is a microphotograph image of a cross-section of a sample of a three-dimensional pulp object comprising a low density pulp base material, according to certain embodiments of the present invention.
Figure 67:
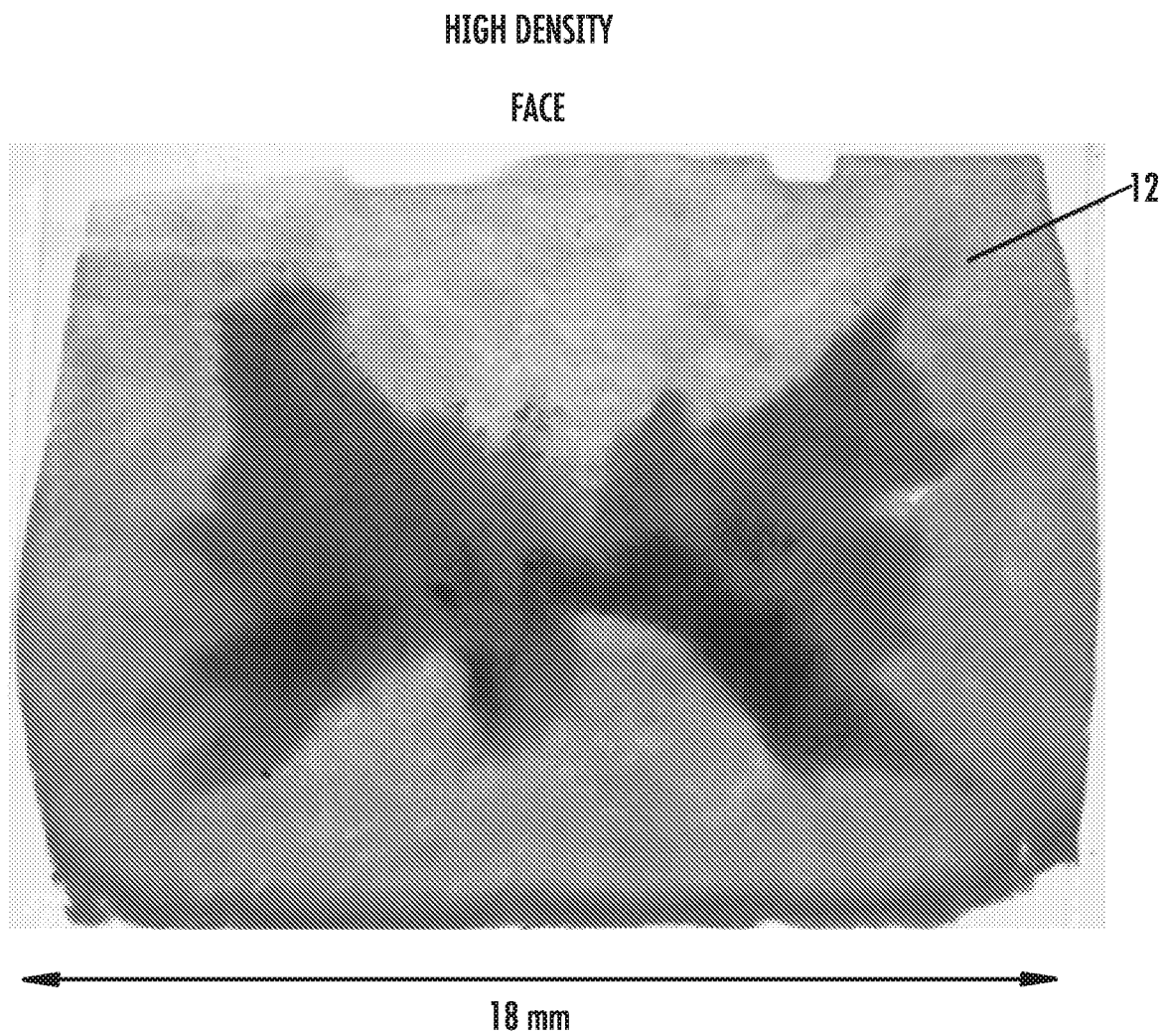
FIG. 67 is a microphotograph image of a cross-section of a sample of a three-dimensional pulp object comprising a high density pulp base material, according to certain embodiments of the present invention.
Figure 68:
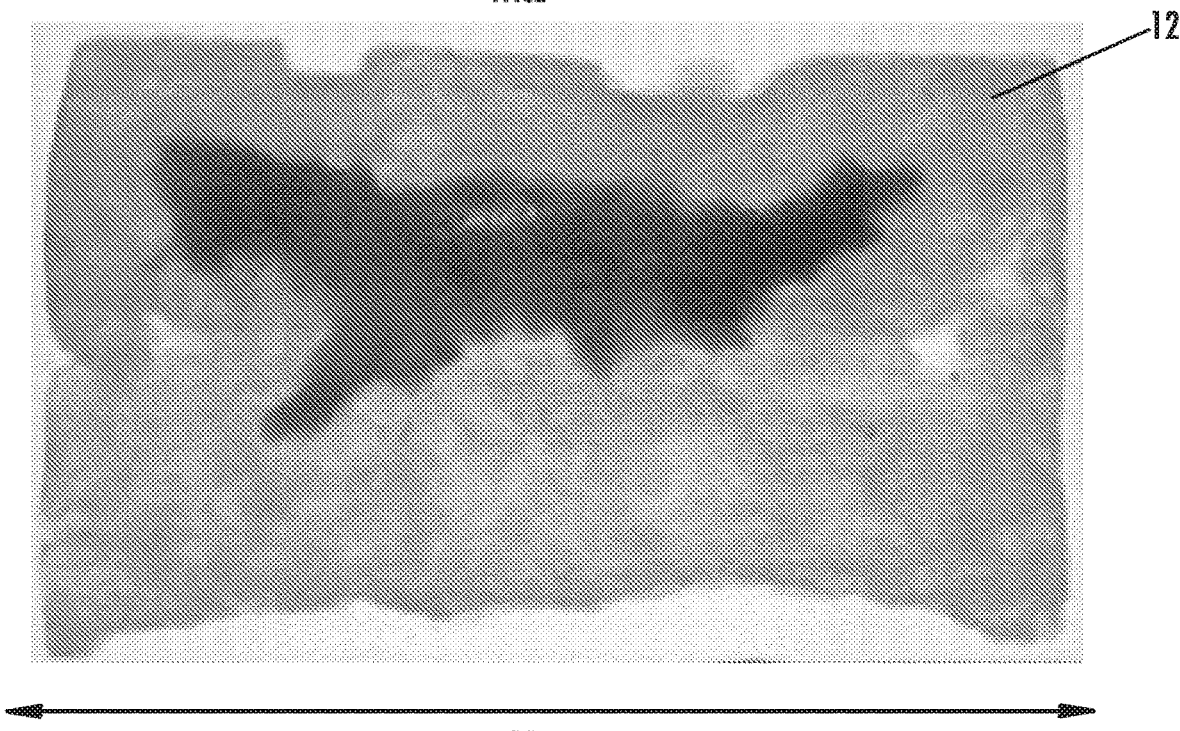
FIG. 68 is a microphotograph image of a cross-section of a sample of a three-dimensional pulp object with both high density pulp material and low density pulp material, according to certain embodiments of the present invention.
Figure 69:
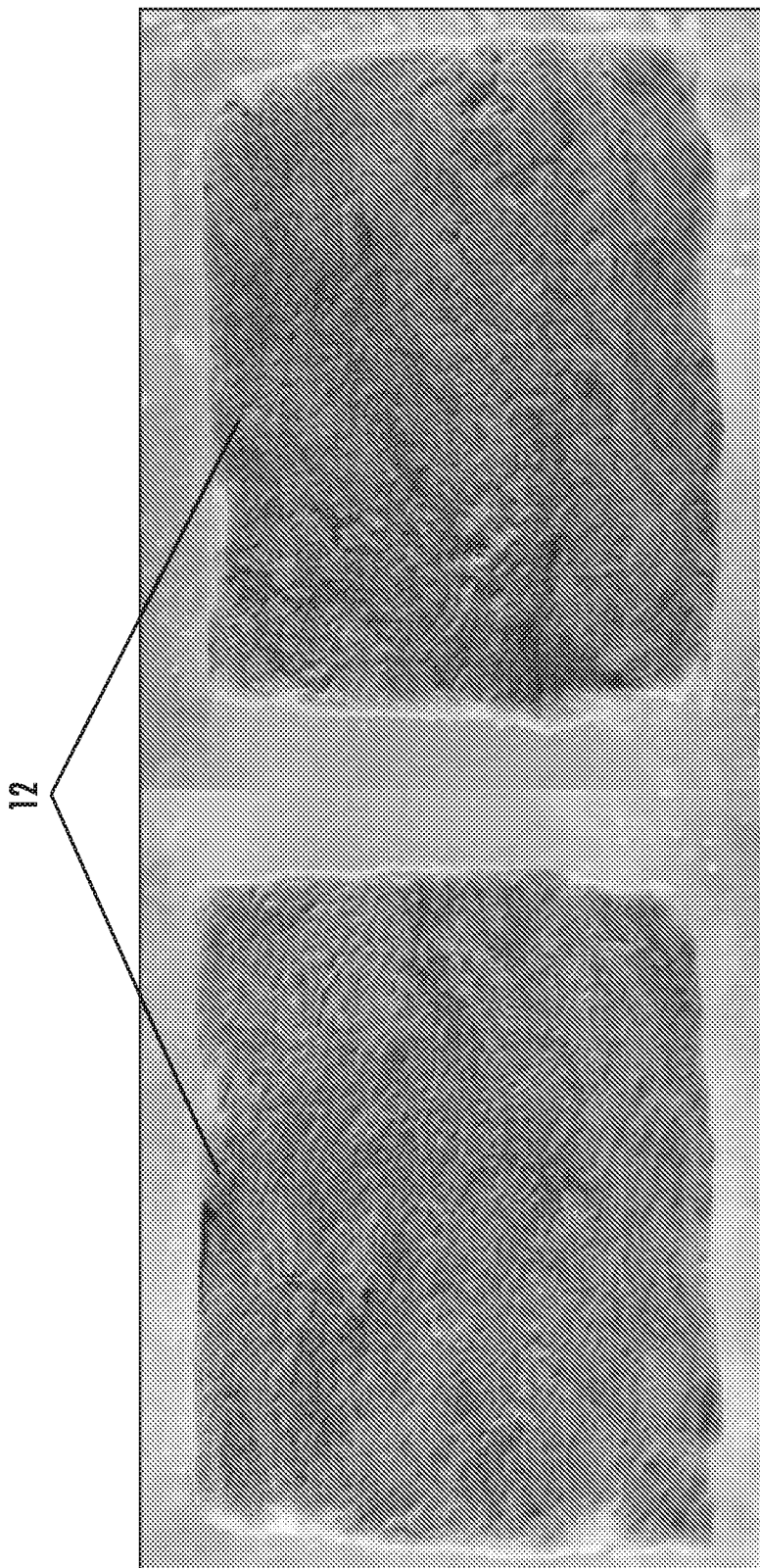
FIG. 69 is a microphotograph low-angle reflected light image of a cross-section of a sample of a three-dimensional pulp object comprising a low density pulp base material after iodine staining, according to certain embodiments of the present invention.
Figure 70:
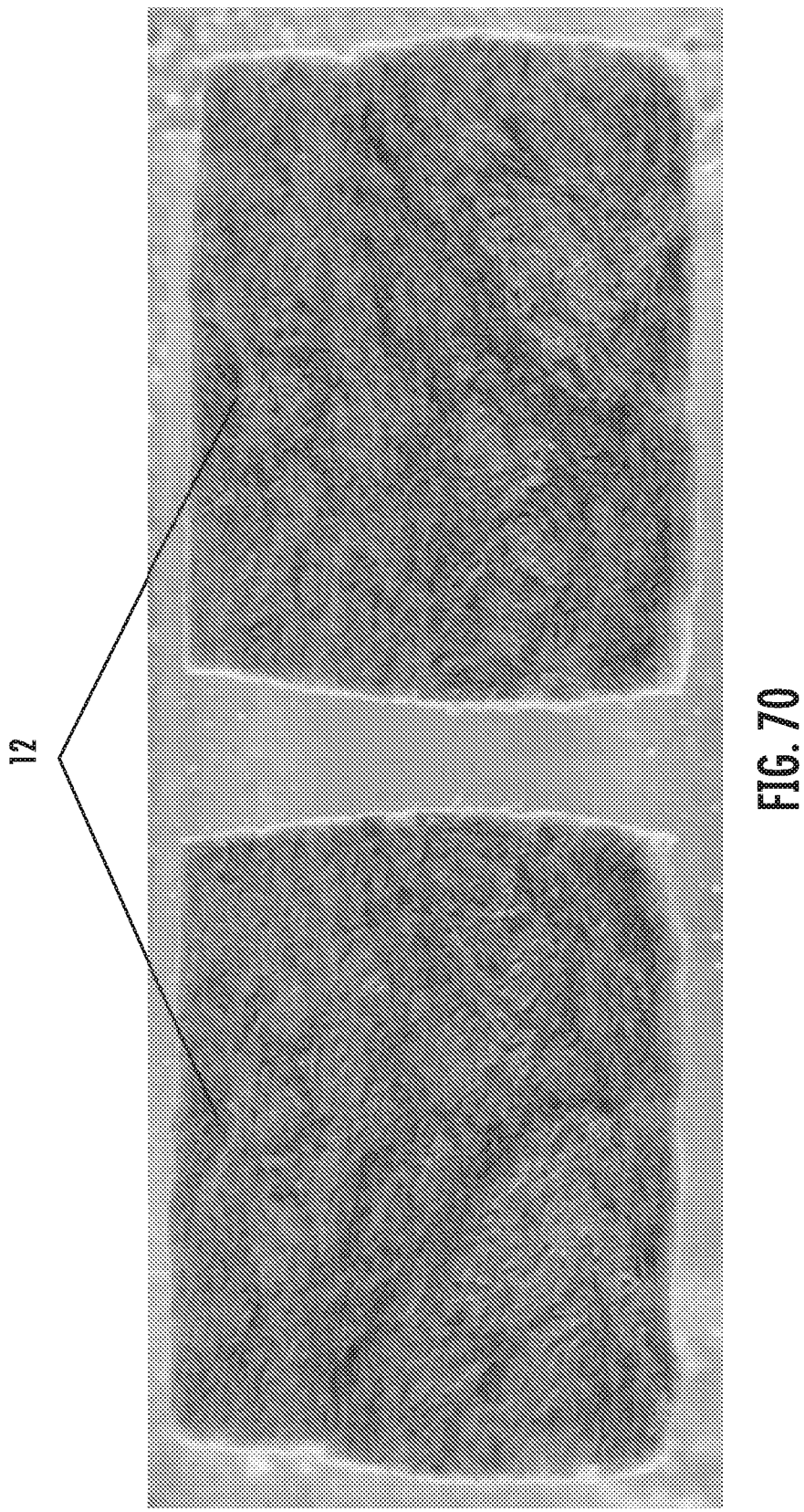
FIG. 70 is a microphotograph low-angle reflected light image of a cross-section of a sample of a three-dimensional pulp object comprising a high density pulp base material after iodine staining, according to certain embodiments of the present invention.

Example 3. Illustration of Fiber Density in Pulp Base Material 12 by Epoxy Embedding and Thin Section Imaging Samples of a three-dimensional pulp object with a high density (0.36 g/mL) and a three-dimensional pulp object with a low density (0.24 g/mL) pulp base material 12 were analyzed using Epoxy Embedding and Thin Section Imaging. Each sample was vacuum filled with Epofix cold mount epoxy resin distributed by Electron Microscopy Sciences. A thin section of each sample was cut with a saw blade and immersed in Cargill refractive index liquid (R.I.=1.572, which matches the R.I. of Epofix). Transmitted light imaging was then used to capture micrographs of the cross-sections of each sample, as may be seen in FIGS. 66, 67 and 68. The dark, spiked features at the centers of the samples indicate incomplete impregnation of the epoxy resin, which also indirectly indicates fiber density. For example, as may be seen in FIG. 67, the epoxy resin impregnation is less complete in the high density sample than in the low density sample shown in FIG. 66. Moreover, FIG. 68, which includes a sample of a three-dimensional pulp object with both high density and low density pulp base material 12, also illustrates less complete epoxy resin impregnation in the area with a higher density than in the area with a lower density. Additionally, in FIG. 67, the faint, gradual change in density from top to bottom in the high density sample, excluding the dark center, is an artifact caused by a change in thin section thickness, as the sample is wedge-shaped. However, the sample in FIG. 68, which includes both high density and low density pulp base materials 12, has a uniform thickness, and thus the faintly darker upper half is indicative of the higher density pulp base material 12 in that area.

C. Modulating Coating

As used herein, "coating" refers to any composition that may be applied using any suitable method to at least one of an outer surface of the article 10, to some or all surfaces of the pulp base material 12, and/or may be uniformly or non-uniformly distributed throughout the internal structure 20 of the base material 12 and/or the article 10. In cases of surface application, the coating may be applied so that the composition may or may not penetrate to at least some degree within the article 10 and/or the base material 12.

Modulating coating 14 may be applied to at least one outer surface 16 of the base material 12 and/or to the article 10, and may be applied before or after loading of the volatile composition 24. In certain embodiments, the modulating coating 14 may penetrate into the internal structure 20 of the base material 12 to a certain level, which may vary depending on the porosity, processing methods, or other characteristics of the base material 12.

The modulating coating 14 is designed to slow the release rate of the volatile composition 24 loaded into the internal structure 20 at higher concentration levels and accelerate the release rate of the volatile composition 24 at lower concentration levels in order to achieve a relatively steady release of volatile composition 24 over time.

To explain the way that the modulating coating 14 works to have this "hold/push" effect over a range of load levels of the volatile composition 24, it is necessary to explain the way in which the release rate of the volatile composition 24 is generated. The volatile composition 24 is loaded or absorbed into the internal structure 20 via the pores 22 until a sufficiently high load level is achieved within the internal structure 20 through various embodiments of loading methods, which are explained in detail below. The volatile composition 24 may be loaded or absorbed into the internal structure 20 before or after the modulating coating 14 is applied.

The initially high load level of the volatile composition 24 within the internal structure 20 creates an internal force that causes the volatile composition 24 to diffuse or evaporate out of the internal structure 20 as quickly as possible to a region of lower concentration. As the load level of the volatile composition 24 decreases over time, the force that causes the diffusion or evaporation diminishes until there is no longer a force remaining (i.e., an equilibrium point is reached where the volatile composition 24 no longer diffuses or evaporates out of the internal structure 20). The equilibrium point is usually higher than 0% concentration, which causes some of the volatile composition 24 to become trapped within the pores 22 of the internal structure 20.

In conventional applications, such as in U.S. Publication No. 2011/0262377, a coating may be applied to form a layer that slows or retards the rapid release of a volatile composition at higher concentration levels. These conventional coatings typically include substances that trap some of the volatile composition within the coating layer, which slows down the rate of release through the coating. However, because the coating only serves as a barrier or "speed bump" to slow down the rate of release of the volatile composition, the release will eventually stop once the concentration of volatile composition within the internal structure reaches equilibrium (i.e., a level where there is no longer a sufficient concentration to drive the volatile composition through the coating layer, thus allowing some of volatile composition to remain trapped within the coating layer and/or within the internal structure).

The modulating coating 14 comprises both a barrier substance 26 and a hygroscopic substance 28. In particular, in most embodiments, the modulating coating 14 comprises substances that do not chemically interact with the volatile composition 24 itself In these embodiments, when the modulating coating 14 is applied to the outer surface 16 of the internal structure 20, at the higher concentration levels of the volatile composition 24 within the internal structure 20, the barrier substance 26 forms a barrier or "speed bump" to slow down the rate of release of the volatile composition 24 through the modulating coating 14. At these higher initial concentration levels, as illustrated in the early stage section of FIG. 65, the hygroscopic substance 28 does not play a role in modulating the release rate of the volatile composition 24 (i.e., does not absorb any water into the modulating coating 14) because the concentration of the volatile composition 24 within the internal structure 20 is sufficiently high to force a certain amount of the volatile composition 24 to release through the modulating coating 14 at a rate that effectively blocks any water from being attracted into the modulating coating 14 by the hygroscopic substance 28.

Figure 65:
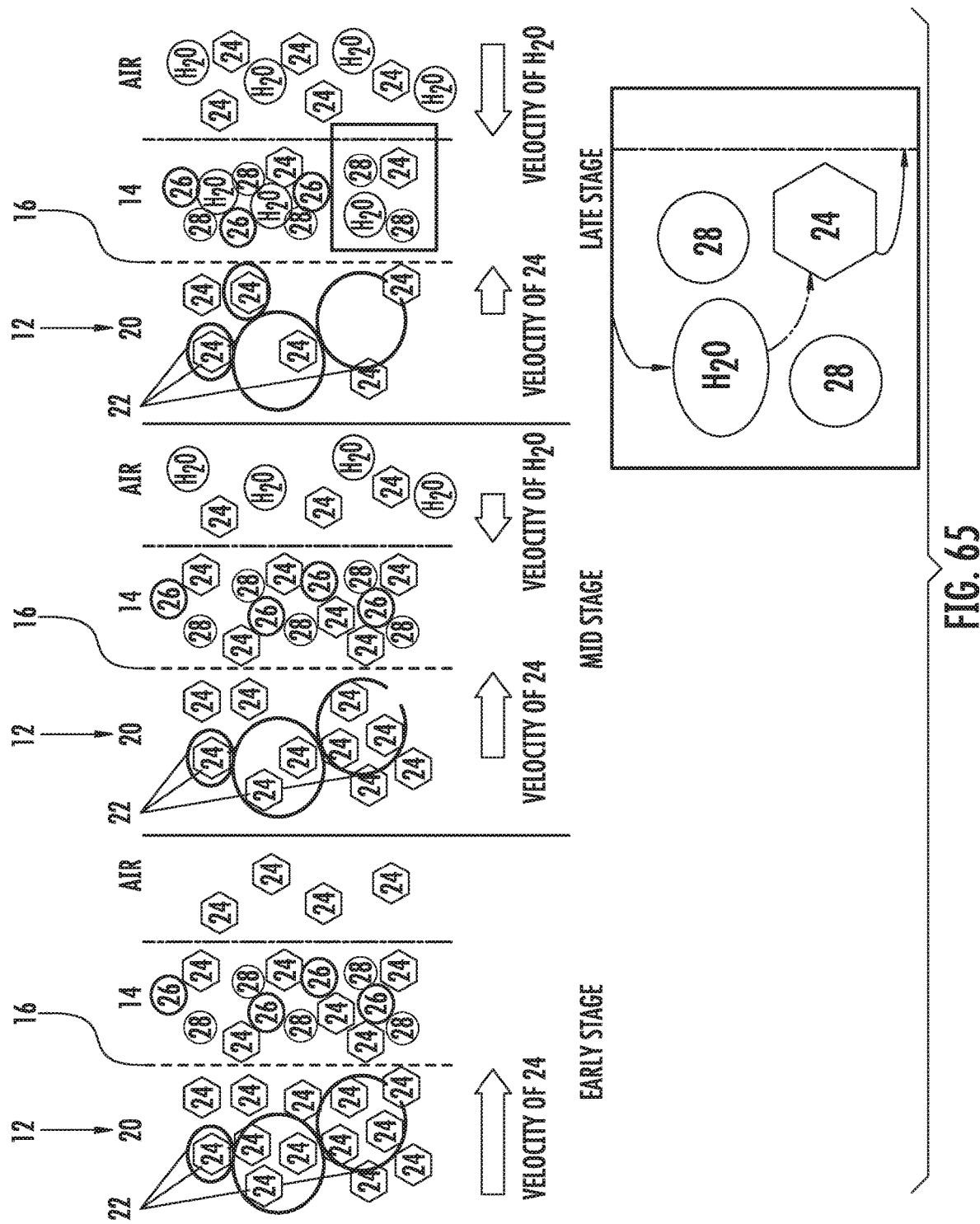
FIG. 65 is a schematic illustrating the movement of a volatile composition across an internal structure of a base material and a modulating coating over time, according to certain embodiments of the present invention.

As the concentration level of the volatile composition 24 within the internal structure 20 slowly diminishes, as illustrated in the mid stage section of FIG. 65, the concentration of the volatile composition 24 within the internal structure 20 is still sufficiently high to continue to force some of the volatile composition 24 out of the modulating coating 14 at a reduced rate of release.

One hypothesis to explain the phenomenon observed in the late stage is that because there is a lower volume of the volatile composition 24 exiting the modulating coating 14, the hygroscopic substance 28 begins to attract more water (typically in the form of water vapor) into the modulating coating 14, whereupon the water adsorbs or absorbs to the hygroscopic substance 28 and begins to displace the volatile composition 24 that is trapped by the barrier substance 26 within the modulating coating 14. This hypothesis is illustrated in the late stage section of FIG. 65, and is based on known physical properties of the hygroscopic substance 28 and the data showing higher release rates at the end of the product life cycle, as compared to the same product without the modulating coating 14. Once displaced, the volatile composition 24 is released from the modulating coating 14, thereby creating an aggregate rate of release of the volatile composition 24 that may approximate the rate of release driven by the higher load level of the volatile composition 24 alone.

As the load level of volatile composition 24 continues to drop to a level that can no longer drive the volatile composition 24 out of the modulating coating 14, the hygroscopic substance 28 continues to pull more and more water into the modulating coating 14. That water continues to displace the trapped volatile composition 24, effectively forcing the displaced volatile composition 24 to be released from the modulating coating 14. For a period of time in the late stage, the rate of release of the volatile composition 24 due to water displacement driven by the hygroscopic substance 28 may approximate the rate of release driven by the higher load level of the volatile composition 24 alone and/or may approximate the aggregate rate of release driven by both the higher load level of the volatile composition 24 and water displacement driven by the hygroscopic substance 28. As a result, where conventional coatings that contain only barrier substances 26 may have stopped releasing volatile compositions once the equilibrium point of the concentration is reached within the internal structure 20, the modulating coating 14 continues to provide a relatively constant release of the volatile composition 24.

An alternate hypothesis to explain the phenomenon observed in the late stage is that the water that is brought into the modulating coating 14 by the hygroscopic substance 28 may act to degrade the barrier substance 26, which would also allow for release of the volatile composition 24 trapped within the modulating coating 14 and within the internal structure 20 of the base material 12.

In any event, the test results demonstrate that the modulating coating 14 generates an improved release profile of the volatile composition 24 over the aromatic life cycle of the article 10, depending on the porosity of the internal structure 20 of the base material 12 and the volatility levels of the volatile composition 24. Eventually, the concentration of the volatile composition 24 within the internal structure 20 and the amount trapped by the barrier substances 26 within the modulating coating 14 will reach such a low point that the amount of volatile composition 24 released on a daily basis by the modulating coating 14 will eventually decline to zero. A series of examples supporting and explaining this process are provided in U.S. Publication No. 2016/0089468, the entire contents of which are incorporated herein by reference.

In certain embodiments, the barrier substance 26 may comprise maltodextrin (e.g. Maltrin). In other embodiments, the barrier substance 26 may include, but is not limited to other dextrins, other film-forming polysaccharides, other carbohydrates (mono-, di-, tri-, etc.), natural unmodified starch, modified starch, any starch appropriate for use in papermaking, as well as combinations of starch types, dextrin types, and combinations of starches and dextrins. In certain embodiments, the barrier substance 26 may include, but not is limited to additives such as insolubilizers, lubricants, dispersants, defoamers, crosslinkers, binders, surfactants, leveling agents, wetting agents, surface additives, rheology modifiers, non-stick agents, and other coating additives.

In certain embodiments, the hygroscopic substance 28 may comprise silica (e.g. silica nanoparticles). In other embodiments, the hygroscopic substance 28 may include, but is not limited to other hygroscopic reagents, activated charcoal, calcium sulfate, calcium chloride, molecular sieves, or other suitable water absorbing materials.

The weight ratio of the barrier substance 26 to the hygroscopic substance 28 may range from 99:1 to 1:99, and all ranges therein between. In certain embodiments, weight ratio of the barrier substance 26 to the hygroscopic substance 28 may further range from 25:75 to 75:25. In yet other embodiments, the weight ratio of the barrier substance 26 to the hygroscopic substance 28 may be approximately 50:50.

In certain embodiments, the particle size of the hygroscopic substance 28 is determined in part by the amount of surface area needed to attract enough water to counteract the drop in release rate due to a reduction in the load level of the volatile composition 24. The hygroscopic substance 28 is also configured so that it will attract water vapor, rather than liquid water. As a result, the diameter of the particle size of the hygroscopic substance 28 may range from 0.001 μm-1 μm, and all ranges therein between, and may further range from 1 nm-100 nm, which will attract the appropriate amount of water vapor molecules, as well as provide a more even coating.

In certain embodiments, the hygroscopic substance 28 may have a surface charge range that ensures interaction with the barrier substances 26. For example, in the case of silica, the surface charge ranges from −10 mV to −4000 mV, as measured by Zeta potential, which is a highly anionic point charge. When the silica is mixed with the maltodextrin before coating, the maltodextrin may group around the silica particles, which may further assist with the barrier formation within the modulating coating 14.

In certain embodiments, the modulating coating 14 may provide a more consistent release rate of the volatile compound 24. The consistency (variance) may be measured by the following formula.

$$\text{Variance}_{(Weight\text{-}loss\ ratio)} = \text{First day weight-loss value} / \text{Last day weight-loss value}$$

A benefit of the modulating coating 14 is to reduce the variance within a ratio range of 1 to 20 over a life cycle of the article, which in certain embodiments may be 30 days, but could be longer or shorter as needed or desired.

In certain embodiments, the modulating coating 14 may be used in combination with the porosity zones 1202 described above. For example, the modulating coating 14 may be applied to the external surfaces of the pulp base material 12 or may only be applied to the external surfaces of the low porosity zone 1208 to further enhance the regulating effect of the low porosity/high density design of that zone for top note volatile components 24.

An additional benefit of the modulating coating 14 is the structural reinforcement that the modulating coating 14 provides to the pulp base material 12, particularly for the high porosity zones 1206. In some embodiments, the modulating coating 14 may only be applied to the external surfaces of the high porosity zone 1206 to provide additional stability to those high porosity zones 1206, even if the coating may also temper the release rate of base note volatile compositions 24 from the high porosity zones 1206.

D. Additional Treatment of the Base Material and/or Article

The base material 12 may be converted into the article 10, which may occur before or after the modulating coating 14 and/or the volatile composition 24 are applied.

In further embodiments, the article 10 may comprise a three-dimensional structure with varying shapes and sizes including but not limited to a cylindrical disk, cylinder, tree, wreath, globe, orb, pine cone, star, bell, stocking, bag, gift box, snowman, penguin, reindeer, santa claus, heart, angel, basket, flower, butterfly, leaf, face, bird, fish, mammal, reptile, pyramid, cone, snowflake, other polygonal shape, fan blade or a portion thereof. The article 10 may have one or more flat surfaces, concave surfaces, convex surfaces, surfaces that are smooth, and/or surfaces that contain complex geometry (e.g., peaks and valleys), or any other suitable surface configuration.

In certain embodiments, the article 10 may comprise a spiral wound paper. The spiral winding process allows for the paper to be the same or different for each layer formed by winding the paper one complete revolution around the axis of the structural component. For example, the article 10 may comprise a rod shape, formed by winding the pulp base material 12 around a vertical axis, so that a rod having a length longer than its diameter is formed. Each layer formed by the complete revolution of the paper matrix around the axis may be referred to as a ply. For example, a 10 ply rod may have from one to ten different characteristics for each ply of the rod. Characteristics may include but are not limited to absorbance, tensile strength density, pH, porosity, and polarity of the base material 12, and the type of paper or internal structure 20.

The modulating coating 14 may be applied to the pulp base material 12 before or after application of the volatile composition 24.

The modulating coating 14 may be applied to pulp base material 12 after it has been removed from the mold 1204 and/or after it has been formed into the article 10.

For example, the modulating coating 14 may be applied to the pulp base material 12 and/or the article 10 via a dip method where the three-dimensional article 10 is placed within a volume of modulating coating 14 for a specified amount of time, then removed and allowed to dry. The dip method may also be used with two-dimensional versions of the article 10. The add-on level may range from 0.1% to 10% by weight.

In other embodiments, the modulating coating 14 may be applied to the pulp base material 12 and/or the article 10 via an infusion method with the add-on infusion ranging from 1% to 20% by weight, and, in certain embodiments, may further range from 10% to 20% by weight.

In yet other embodiments, the modulating coating 14 may be applied to pulp base material 12 and/or the article 10 via spray treatment.

The volatile composition 24 may be applied to the base material 12 before or after application of the modulating coating 14, as described above. For example, the volatile composition 24 may be applied by placing the base material 12 and/or the article 10 in intimate contact with the volatile composition 24 for a period of time. The volatile composition 24 may be in any physical state, such as liquid, solid, gel, or gas. For convenience, a liquid volatile composition 24 is described, but this is not intended to be limiting. The interaction time may depend on the concentration or type of volatile composition 24 being applied to the base material 12 and/or the article 10, and/or how strong or intense of a volatile composition 24 release is desired, and/or the type of base material 12. The saturation time (interaction time) may range from less than one minute to a several hours, to several days. The base material 12 and/or the article 10 may be pre-treated prior to exposure to the volatile composition 24. For example, the base material 12 and/or the article 10 may be placed in a drying oven to remove any residual moisture. Further method steps comprise pressure treating and/or vacuum treating the base material 12 and/or the article 10. After treatment, the base material 12 and/or the article 10 may be dried, for example by rubbing or patting dry, and/or by other methods known for drying a surface, and/or may be left to air dry. Drying steps may be used before or after other steps described herein.

In some embodiments, a method for applying the volatile composition 24 to the base material 12 and/or to the article 10 comprises combining the volatile composition 24 and the base material 12 and/or the article 10 in a container and applying a pressure above atmospheric pressure on the volatile composition 24 and base material 12 and/or the article 10. Pressure may be applied in a range from about 1 psi to about 40 psi, from about 5 psi to about 30 psi, or from about 10 psi to about 20 psi, at about 5 psi, at about 10 psi, at about 15 psi, at about 20 psi, at about 25 psi, at about 30 psi, at about 35 psi, at about 40 psi, and/or at pressures therein between. The pressure may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or the article 10 to achieve a desired load of the volatile composition 24 to the base material 12 and/or the article 10 or release of the volatile composition 24 from the base material 12 and/or the article 10. Appropriate pressures and times for a particular embodiment can be determined by one skilled in the art based on the identities and characteristics of the particular volatile composition 24 and base material 12 and/or article 10.

In certain embodiments, a method for applying the volatile composition 24 comprises combining the volatile composition 24 and base material 12 and/or the article 10 in a container and applying a vacuum below atmospheric pressure to the volatile composition 24 and the base material 12 and/or the article 10. Vacuum may be applied in a range from 0.001 mm Hg to about 700 mm Hg, or from about 5 Kpa to about 35 kPa, from about 10 Kpa to about 25 kPa, from about 20 Kpa to about 30 kPa, from about 15 Kpa to about 25 kPa, from about 25 Kpa to about 30 kPa, at about 5 kPa, at about 6 kPa, at about 7 kPa, at about 8 kPa, at about 9 kPa, at about 10 kPa, at about 15 kPa, at about 16 kPa, at about 17 kPa, at about 18 kPa, at about 19 kPa, at about 20 kPa, at about 22 kPa, at about 24 kPa, at about 26 kPa, at about 28 kPa, at about 30 kPa, and vacuums therein between. The vacuum may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or the article 10 to achieve a desired load of the volatile composition 24 to the base material 12 and/or the article 10 or release of the volatile composition 24 from the base material 12 and/or the article 10.

In yet other embodiments, the method may comprise pressure and vacuum steps. The volatile composition 24 and the base material 12 and/or the article 10 may be combined and undergo vacuum treatment and pressure treatment, in no particular order. For example, the volatile composition 24 and the base material 12 and/or the article 10 may be combined in a container in an air-tight apparatus and a vacuum of 20 mm Hg to 80 mm Hg may be applied for about 1 minute to 10 hours. Pressure treatment of 1 psi to 40 psi may be applied for about 1 minute to about 10 hours and the time and amount of vacuum or pressure treatment may vary and depend upon the amount of volatile composition 24 to be loaded in the base material 12 and/or the article 10, the type of base material 12 used, the intended use of the article 10, and other characteristics of the article 10.

In certain embodiments, the base material 12 and/or the article 10 may be pre-treated with colorants, followed by treatment with the modulating coating 14. Colorants may include natural and synthetic dyes, water-resistant dyes, oil-resistant dyes, oil soluble dyes, and combinations of water- and oil-resistant dyes. Colorants may be selected based on the composition of the base material 12, and is well within the skill of those in the art. Suitable water-resistant colorants include oil soluble colorants and wax soluble colorants. Examples of oil soluble colorants include Pylakrome Dark Green and Pylakrome Red (Pylam Products Company, Tempe Ariz.). Suitable oil-resistant colorants include water soluble colorants. Examples of water soluble colorants include FD&C Blue No. 1 and Carmine (Sensient, St. Louis, Mo.). A Lake type dye may also be used. Examples of Lake dyes are Cartasol Blue KRL-NA LIQ and Cartasol Yellow KGL LIQ (Clariant Corporation, Charlotte, N.C.). Pigments may also be used in coloring the base material 12 and may be added during or after the manufacture of the base material 12. Such coloring or dying methods are known to those skilled in the art, and any suitable dyes, pigments, or colorants are contemplated by the present invention. Colorants may be used to affect the overall surface charge of the silica or other hygroscopic substance 28 to enhance the interaction with the coating.

In certain embodiments, ink or paint may be applied to the surface of the article 10 to provide complex designs, such as those shown in FIGS. 21, 28, 30A-30B, 33A-33B, 37-39, 51-55. Such techniques are similar to those used to apply ink or paint to ceramic materials. The ink or paint may be applied in combination with dyes and/or in lieu of the dye process.

E. Solvent-Free Fragrance Dispenser

According to certain embodiments, the article 10 is formed of all-natural, biodegradable, recyclable, compostable and sustainably sourced materials, such as wood pulp. These materials are combined with all-natural biodegradable, recyclable, compostable performance boosters, such as silica, starch, and baking soda. The product is then treated with fragrance, such as 100% pure fragrance in the form of all-natural essential oils and/or other responsibly selected and harvested fragrance materials.

Specifically, the article 10 does not include a chemical solvent. Chemical solvents minimize the amount of fragrance that can be used (by as much as 85%) and compromise duration. Furthermore, chemical solvents have a chemical overtone that is difficult to entirely overcome with perfume. Use of chemical solvents means that it is impossible to completely eliminate carcinogens, respiratory sensitizers, asthmagens, phthalates and persistent bio-accumulative toxins, which lead to a compromised health and wellness profile.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and That which is claimed is:

1. An article comprising
   a pulp base material comprising:
      fibers, wherein pores are formed between the fibers; and
      at least one surface having complex geometry comprising peaks and flatter regions;
   a volatile composition comprising at least one top note component having a first volatility and at least one base note component having a second volatility;
   wherein the first volatility is higher than the second volatility;
   wherein the volatile composition at least partially fills the pores of the pulp base material;
   wherein a release rate of the at least one top note component is modulated by the pulp base material; and
   wherein a release rate of the at least one base note component is enhanced by the pulp base material.

2. The article of claim 1, wherein the pulp base material comprises:
   at least one low porosity zone having a first porosity; and
   at least one high porosity zone having a second porosity; and
   wherein the first porosity is lower than the second porosity.

3. The article of claim 2, wherein the at least one top note component is added to the at least one low porosity zone, and the at least one base note component is added to the at least one high porosity zone.

4. The article of claim 2, wherein the at least one low porosity zone and the at least one high porosity zone are formed by use of a mold having different drainage surfaces.

5. The article of claim 2, wherein the at least one low porosity zone and the at least one high porosity zone are formed by use of a divider within a mold.

6. The article of claim 2, wherein the at least one low porosity zone and the at least one high porosity zone are formed by application of different pressures to portions of a mold.

7. The article of claim 2, wherein the at least one low porosity zone and the at least one high porosity zone are formed by application of different pulp concentrations to portions of a mold.

8. The article of claim 2, wherein the at least one low porosity zone and the at least one high porosity zone are formed by application of different amounts of gas or gas-forming materials to portions of the pulp base material.

9. The article of claim 1, wherein the peaks enhance the release rate of the volatile composition.

10. The article of claim 1, wherein the peaks provide three-dimensional emission of the volatile composition.

11. The article of claim 1, wherein the article comprises an attachment element.

12. The article of claim 1, further comprising a backing layer added to the article, wherein the backing layer is formed of a metallic material.

13. The article of claim 1, further comprising an opening through the article for placement of a light source.

14. The article of claim 1, wherein the pulp base material comprises a first porosity and openings in which other materials having at least a second porosity are added to the pulp base material.

15. The article of claim 2, wherein a modulating coating is applied to the pulp base material.

16. The article of claim 15, wherein the modulating coating is only applied to the at least one low porosity zone.

17. The article of claim 15, wherein the modulating coating is only applied to the at least one high porosity zone.

18. The article of claim 1, wherein the article is combined with at least one energy source, wherein the at least one energy source includes at least one of a warmer bowl, a plate, or a fan.

19. The article of claim 2, wherein:
   the volatile composition is mixed with a dye before at least partially filling the pores of the pulp base material such that the at least one low porosity zone has a different visual appearance compared to the at least one high porosity zone; and
   the at least one low porosity zone has a darker color based on a color of the dye while the at least one high porosity zone has a color similar to the pulp base material without the dye.

20. An article comprising
   a pulp base material comprising:
      fibers, wherein pores are formed between the fibers;
      at least one surface having complex geometry, wherein the complex geometry comprises peaks and flatter regions;
   a second material disposed within the pulp base material; and
   a volatile composition comprising at least one top note component having a first volatility and at least one base note component having a second volatility;
   wherein the first volatility is higher than the second volatility;
   wherein the volatile composition at least partially fills the pores of the pulp base material;
   wherein a release rate of the at least one top note component is modulated by the pulp base material; and
   wherein a release rate of the at least one base note component is modulated by the pulp base material.

21. The article of claim 20, wherein the second material comprises a biological plant-derived material.

22. The article of claim 20, wherein the second material comprises a scented rod of spiral wound paper.

23. The article of claim 20, wherein the second material is disposed within at least one opening of the pulp base material.

24. The article of claim 20, wherein the second material comprises second fibers having a different density compared to the fibers of the pulp base material.

25. The article of claim 20, wherein the second material comprises second fibers, wherein the second fibers are from a different source compared to the fibers of the pulp base material.

* * * * *